(12) United States Patent
Yao et al.

(10) Patent No.: US 10,800,765 B2
(45) Date of Patent: Oct. 13, 2020

(54) INDOLE DERIVATIVE USED AS CRTH2 INHIBITOR

(71) Applicants: CHIA TAI TIANQING PHARMACEUTICAL GROUP CO., LTD., Lianyungang (CN); MEDSHINE DISCOVERY INC., Nanjing (CN)

(72) Inventors: Yuanshan Yao, Shanghai (CN); Bin Chen, Shanghai (CN); Yuan Chen, Shanghai (CN); Ao Li, Shanghai (CN); Ran Xu, Shanghai (CN); Zhensheng Huang, Shanghai (CN); Dongdong Tian, Shanghai (CN); Hongwei Li, Shanghai (CN); Chengshuai Yang, Shanghai (CN); Jian Li, Shanghai (CN); Shuhui Chen, Shanghai (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 0 days.

(21) Appl. No.: 16/318,523

(22) PCT Filed: Jul. 21, 2017

(86) PCT No.: PCT/CN2017/093860
§ 371 (c)(1),
(2) Date: Jan. 17, 2019

(87) PCT Pub. No.: WO2018/014869
PCT Pub. Date: Jan. 25, 2018

(65) Prior Publication Data
US 2019/0248770 A1    Aug. 15, 2019

(30) Foreign Application Priority Data
Jul. 21, 2016   (CN) .......................... 2016 1 0581831

(51) Int. Cl.
| | |
|---|---|
| *C07D 409/04* | (2006.01) |
| *C07D 409/06* | (2006.01) |
| *C07D 409/14* | (2006.01) |
| *C07D 417/06* | (2006.01) |
| *C07D 417/10* | (2006.01) |
| *C07D 495/04* | (2006.01) |
| *A61K 31/405* | (2006.01) |
| *A61P 43/00* | (2006.01) |
| *A61P 11/06* | (2006.01) |
| *A61P 37/08* | (2006.01) |
| *A61K 31/4365* | (2006.01) |
| *A61K 31/4439* | (2006.01) |

(52) U.S. Cl.
CPC .......... *C07D 409/04* (2013.01); *A61K 31/405* (2013.01); *A61K 31/4365* (2013.01); *A61K 31/4439* (2013.01); *A61P 11/06* (2018.01); *A61P 37/08* (2018.01); *A61P 43/00* (2018.01); *C07D 409/06* (2013.01); *C07D 409/14* (2013.01); *C07D 417/06* (2013.01); *C07D 417/10* (2013.01); *C07D 495/04* (2013.01)

(58) Field of Classification Search
CPC .. C07D 417/06; C07D 417/10; C07D 409/04; C07D 409/06; C07D 409/10; A61K 31/405; A61P 43/00
USPC .................. 548/206, 214; 514/372
See application file for complete search history.

(56) References Cited

U.S. PATENT DOCUMENTS 7,981,912 B2 *  7/2011  Bennani ............... C07D 209/46
                                                              514/372

FOREIGN PATENT DOCUMENTS

| CN | 101087784 A | 12/2007 |
|---|---|---|
| CN | 104114169 A | 10/2017 |
| WO | 2006/034419 A2 | 3/2006 |

OTHER PUBLICATIONS

Kupczyk et ak., Drugs (2017) 77:1281-1294.*
International Search Report in PCT/CN2017/093860, dated Oct. 23, 2017.
Tumey et al., "3-Indolyl Sultams as Selective CRTh2 Antagonists," Bioorganic & Medicinal Chemistry Letters, vol. 20, No. 11, Apr. 14, 2010, pp. 3287-3290.
Extended European Search Report in EP17830503.3 dated Nov. 28, 2019, 13 pages.
Burlingham, et al. "An intuitive look at the relationship of Ki and IC50: a more general use for the Dixon plot." Journal of chemical education 80, No. 2 (2003): 214.

* cited by examiner

*Primary Examiner* — Venkataraman Balasubramanian
(74) *Attorney, Agent, or Firm* — Kilpatrick Townsend & Stockton LLP

(57) ABSTRACT

The present application discloses an indole as represented by formula (I) used as a CRTH2 inhibitor, and a pharmaceutically acceptable salt or tautomer of the indole, and an application of same in treating a disease related to a CRTH2 receptor.

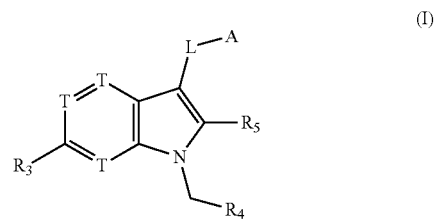

(I)

15 Claims, No Drawings

INDOLE DERIVATIVE USED AS CRTH2 INHIBITOR

CROSS-REFERENCES TO RELATED APPLICATIONS

The present application is a U.S. National Phase of PCT/CN2017/093860, International Filing Date Jul. 21, 2017, which claims the benefit of Chinese Patent Application No. 201610581831.1 filed at the China National Intellectual Property Administration on Jul. 21, 2016, the disclosures of which are incorporated in their entirety herein by reference.

TECHNICAL FIELD

The present application relates to an indole compound as a CRTH2 inhibitor and use thereof in the treatment of a disease associated with a CRTH2 receptor.

BACKGROUND

CRTH2 (DP2 or GPR44) is a G protein-coupled receptor. After combined with prostaglandin (PGD2), it is involved in the activation and chemotaxis of Th2 lymphocytes, eosinophils and basophils, inhibits the apoptosis of Th2 lymphocytes, and stimulates the production of IL4, IL5 and IL13. These interleukins are involved in important biological responses, including eosinophil recruitment and survival, mucus secretion, airway hyperresponsiveness, and immunoglobulin E (IgE) production.

Ramatroban is a TP (thromboxane-type prostanoid) receptor antagonist, triggering extremely strong vascular and bronchial smooth muscle contraction, and platelet activation. Ramatroban is a weak CRTh2 receptor antagonist. Ramatroban has been approved in Japan for treating allergic rhinitis.

WO2005044260 has reported Compound OC459; and WO2005123731 has reported Compound QAW-039.

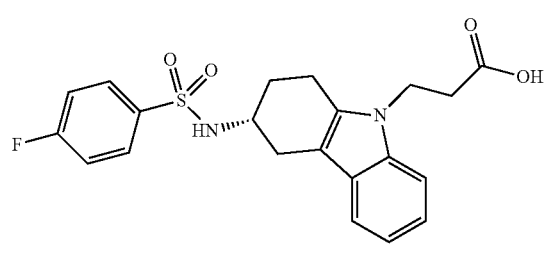

Ramatroban

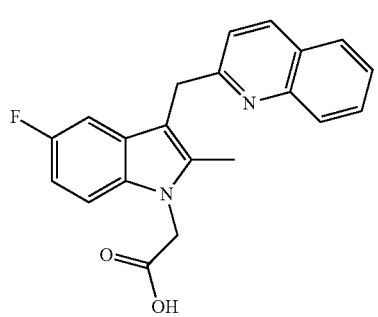

OC459

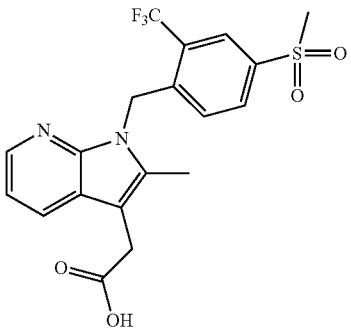

QAW-039

SUMMARY OF THE INVENTION

In one aspect, the present application provides a compound represented by formula (I), or a pharmaceutically acceptable salt, tautomer, or solvate thereof,

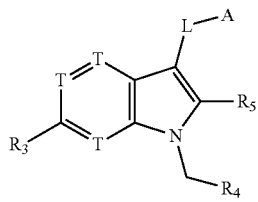

(I)

wherein
A is

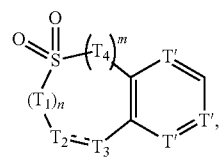

which is optionally substituted with one or more $R_1$;
each T' is independently selected from the group consisting of N, CH, and C;
$T_1$, $T_2$, $T_3$, and $T_4$ are each independently selected from the group consisting of N, —NH—, —CH$_2$—, CH, and C;
m is selected from the group consisting of 0 and 1;
n is selected from the group consisting of 0, 1, and 2;
each $R_1$ is independently selected from the group consisting of F, Cl, Br, I, and —OH; or is independently selected from the following groups: —NH$_2$, $C_{1-3}$ alkyl, $C_{1-3}$ alkyl-S(=O)$_2$—, $C_{3-6}$ cycloalkyl, phenyl, and 5- to 6-membered heteroaryl, which are optionally substituted with 1, 2, or 3 R;
each T is independently selected from the group consisting of N and C($R_3$);
each $R_3$ is independently selected from the group consisting of H, F, Cl, Br, I, OH, and NO$_2$; or is independently selected from the following groups: NH$_2$, $C_{1-3}$ alkyl, $C_{1-3}$ alkylamido, and $C_{3-6}$ cycloalkylamido, which are optionally substituted with 1, 2, or 3 R;
$R_4$ is selected from the group consisting of tetrazolyl, —COOH, and —C(O)—O—$C_{1-3}$ alkyl;
$R_5$ is selected from the group consisting of H, $C_{1-3}$ alkyl, and phenyl;

L is selected from the group consisting of a single bond and methylene optionally substituted with R;

each R is independently selected from the group consisting of F, Cl, Br, I, —CN, —OH, and —COOH; or is independently selected from the following groups: —NH$_2$, C$_1$0.6 alkyl, C$_{3-6}$ cycloalkyl, 3- to 6-membered heterocycloalkyl, phenyl, and 5- to 6-membered heteroaryl, which are optionally substituted with 1, 2, or 3 R'; and each R' is independently selected from the group consisting of F, Cl, Br, I, —OH, —CN, —NH$_2$, —COOH, Me, Et, —CF$_3$, —CHF$_2$, —CH$_2$F, —NHCH$_3$, and —N(CH$_3$)$_2$.

In another aspect, the present application provides a pharmaceutical composition, comprising a compound represented by formula (I) of the present application, or a pharmaceutically acceptable salt thereof, or a tautomer thereof, or a solvate thereof, and a pharmaceutically acceptable adjuvant.

In another aspect, the present application provides a method for treating a disease mediated by a CRTH2 receptor in a mammal, comprising administering to a mammal, preferably a human, in need thereof a therapeutically effective amount of a compound represented by formula (I), or a pharmaceutically acceptable salt thereof, or a tautomer thereof, or a solvate thereof, or a pharmaceutical composition thereof.

In still another aspect, the present application relates to use of a compound represented by formula (I), or a pharmaceutically acceptable salt thereof, or a tautomer thereof, or a solvate thereof, or a pharmaceutical composition thereof in the preparation of a medicament for preventing or treating a disease mediated by a CRTH2 receptor.

In yet another aspect, the present application relates to a compound represented by formula (I), or a pharmaceutically acceptable salt thereof, or a tautomer thereof, or a solvate thereof, or a pharmaceutical composition thereof for use in preventing or treating a disease mediated by a CRTH2 receptor.

DETAILED DESCRIPTION OF THE INVENTION

In the following description, certain specific details are included to provide a thorough understanding of various disclosed embodiments. However, those skilled in the relevant art will recognize that the embodiments may be practiced without one or more of these specific details, but with other methods, components, materials, and the like.

Unless the context requires otherwise, throughout the specification and the claims thereafter, the word "comprise" and English variations thereof, such as "comprises" and "comprising", should be construed in an open and inclusive sense, that is, as "including, but not limited to".

Reference throughout this specification to "one embodiment", or "an embodiment", or "another embodiment", or "some embodiments" means that a particular referent element, structure, or characteristic described in connection with the embodiment is included in at least one embodiment. Accordingly, the phase "in one embodiment", or "in an embodiment", or "in another embodiment", or "in some embodiments" that appears in various places throughout this specification are not necessarily all referring to the same embodiment. In addition, the particular elements, structures, or characteristics may be combined in any suitable manner in one or more embodiments.

It should be noted that, as used in this specification and the appended claims, the singular forms "a", "an" and "the" include plural referents unless the context clearly dictates otherwise. Accordingly, for example, reference to a reaction in which "a catalyst" is involved includes a single catalyst, or two or more catalysts. It should also be noted that the term "or" is generally used in its sense including "and/or", unless the context clearly dictates otherwise.

The present application provides a compound represented by formula (I), or a pharmaceutically acceptable salt, tautomer, or solvate thereof,

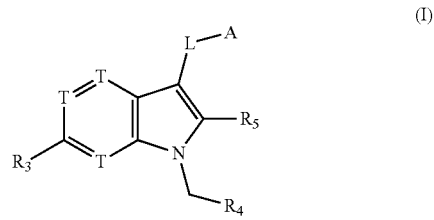

(I)

wherein
A is

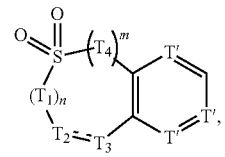

which is optionally substituted with one or more R$_1$;

each T' is independently selected from the group consisting of N, CH, and C;

T$_1$, T$_2$, T$_3$, and T$_4$ are each independently selected from the group consisting of N, —NH—, —CH$_2$—, CH, and C;

m is selected from the group consisting of 0 and 1;

n is selected from the group consisting of 0, 1, and 2;

each R$_1$ is independently selected from the group consisting of F, Cl, Br, I, and —OH; or is independently selected from the following groups: —NH$_2$, C$_{1-3}$ alkyl, C$_{1-3}$ alkyl-S(=O)$_2$—, C$_{3-6}$ cycloalkyl, phenyl, and 5- to 6-membered heteroaryl, which are optionally substituted with 1, 2, or 3 R;

each T is independently selected from the group consisting of N and C(R$_3$);

each R$_3$ is independently selected from the group consisting of H, F, Cl, Br, I, —OH, and —NO$_2$; or is independently selected from the following groups: —NH$_2$, C$_{1-3}$ alkyl, C$_{1-3}$ alkylamido, and C$_{3-6}$ cycloalkylamido, which are optionally substituted with 1, 2, or 3 R;

R$_4$ is selected from the group consisting of tetrazolyl, —COOH, and —C(O)—O—C$_{1-3}$ alkyl;

R$_5$ is selected from the group consisting of H, C$_{1-3}$ alkyl, and phenyl;

L is selected from the group consisting of a single bond and methylene optionally substituted with R;

each R is independently selected from the group consisting of F, Cl, Br, I, —CN, —OH, and —COOH; or is independently selected from the following groups: —NH$_2$, C$_{1-6}$ alkyl, C$_{3-6}$ cycloalkyl, 3- to 6-membered heterocloalkyl, phenyl, and 5- to 6-membered heteroaryl, which are optionally substituted with 1, 2, or 3 R'; and each R' is independently selected from the group consisting of F, Cl, Br, I, —OH, —CN, —NH$_2$, —COOH, Me, Et, —CF$_3$, —CHF$_2$, —CH$_2$F, —NHCH$_3$, and —N(CH$_3$)$_2$.

In some embodiments of the present application, each R is independently selected from the group consisting of F, Cl, Br, I, —CN, —OH, and —COOH; or is independently selected from the group consisting of —NH₂ and C₁₋₄ alkyl, which are optionally substituted with 1, 2, or 3 R'.

In some embodiments of the present application, each R is independently selected from the group consisting of F, Cl, Br, I, —CN, —OH, —NH₂, —COOH, Me, Et, —CF₃, —CHF₂, —CH₂F, —NHCH₃, —N(CH₃)₂,

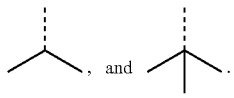, and .

In some embodiments of the present application, L may be attached to any position of A other than the —S(=O)₂— moiety that satisfies the valence requirement.

In some embodiments of the present application, each R₁ is independently selected from the group consisting of F, Cl, Br, I, and —OH; or is independently selected from the following groups: —NH₂, C₁₋₃ alkyl, C₁₋₃ alkyl-S(=O)₂—, C₃₋₆ cycloalkyl, phenyl, pyridinyl, pyrimidinyl, pyrazolyl, imidazolyl, thiazolyl, oxazolyl, and isoxazolyl, which are optionally substituted with 1, 2, or 3 R.

In some embodiments of the present application, each R₁ is independently selected from the group consisting of F, Cl, Br, I, and —OH; or is independently selected from the following groups: Me, NH₂,

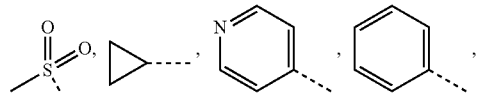

, and , which are optionally substituted with 1, 2, or 3 R.

In some embodiments of the present application, each R₁ is independently selected from the group consisting of F, Cl, Br, I, —OH, —NH₂, Me, —CF₃,

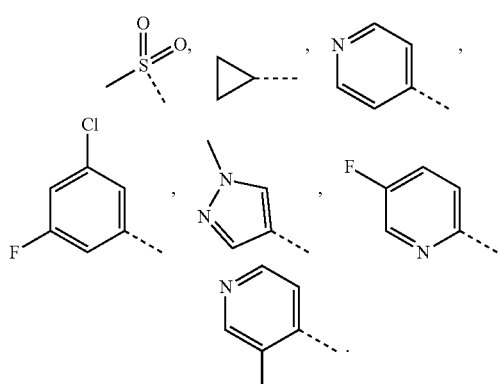

In some embodiments of the present application, each R₁ is independently selected from the group consisting of F, Cl, Me, —CF₃,

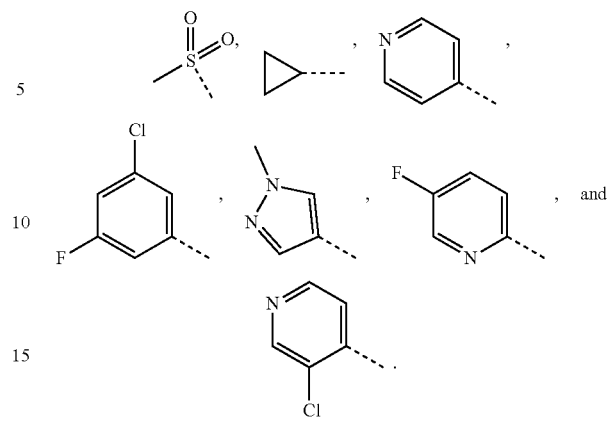

In some embodiments of the present application, A is selected from the group consisting of

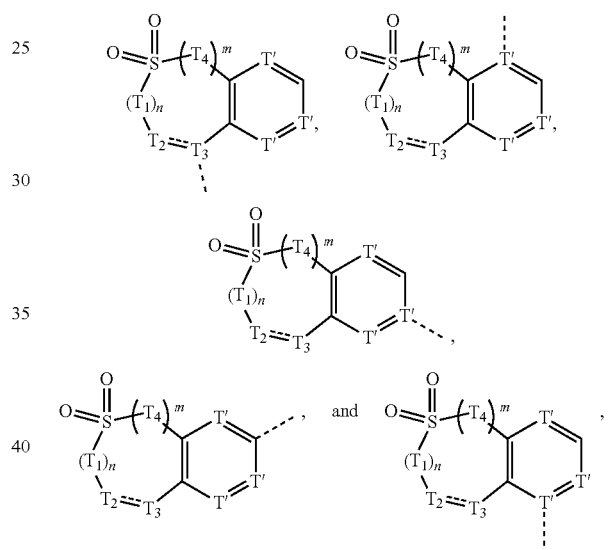

which are optionally substituted with one or more R₁.

In some embodiments of the present application, A is selected from the group consisting of

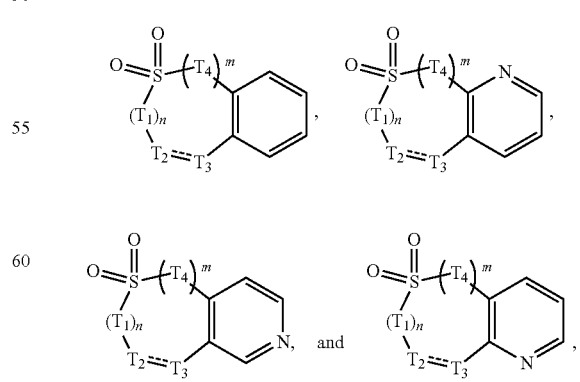

which are optionally substituted with one or more R₁.

In some embodiments of the present application, A is selected from the group consisting of

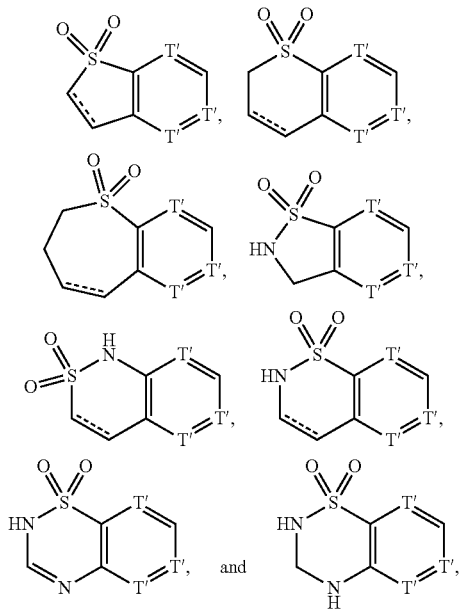

which are optionally substituted with one or more $R_1$.

In some embodiments of the present application, A is selected from the group consisting of

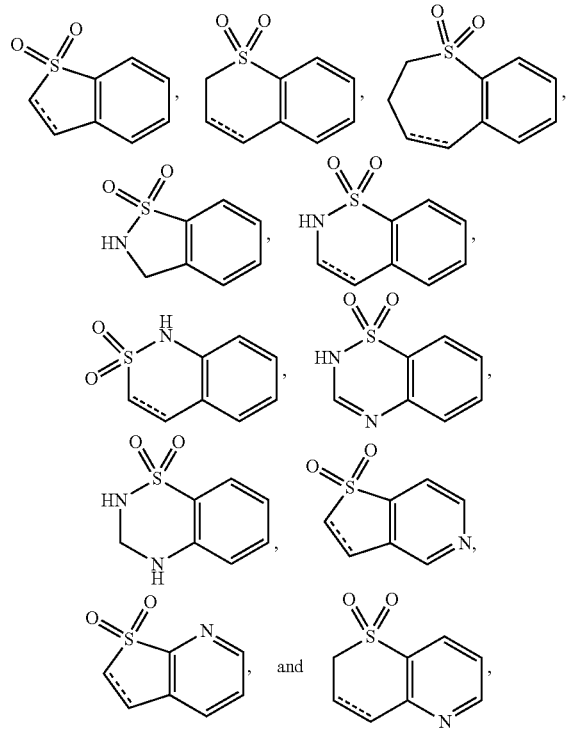

which are optionally substituted with one or more $R_1$.

In some embodiments of the present application, A is selected from the group consisting of

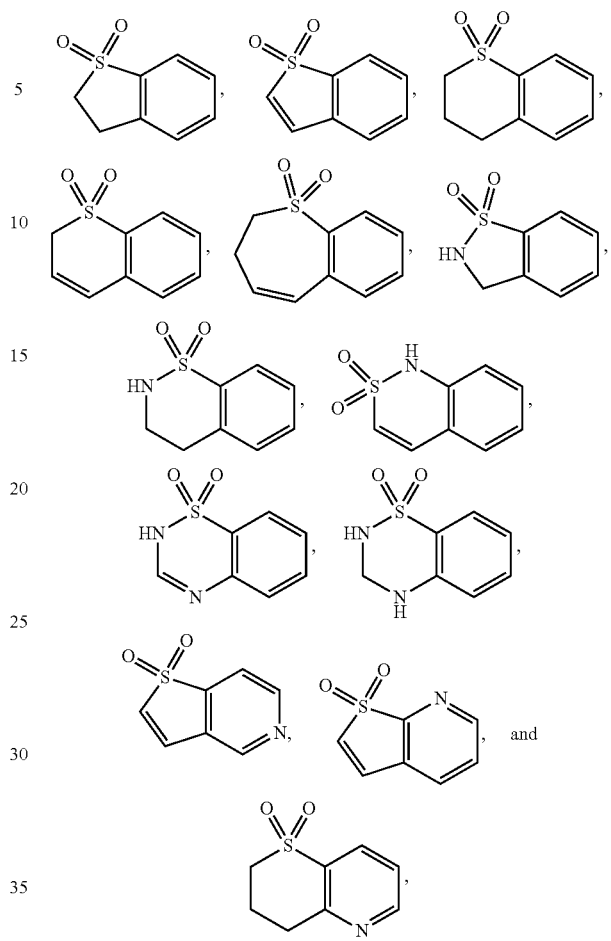

which are optionally substituted with one or more $R_1$.

In some embodiments of the present application, A is selected from the group consisting of

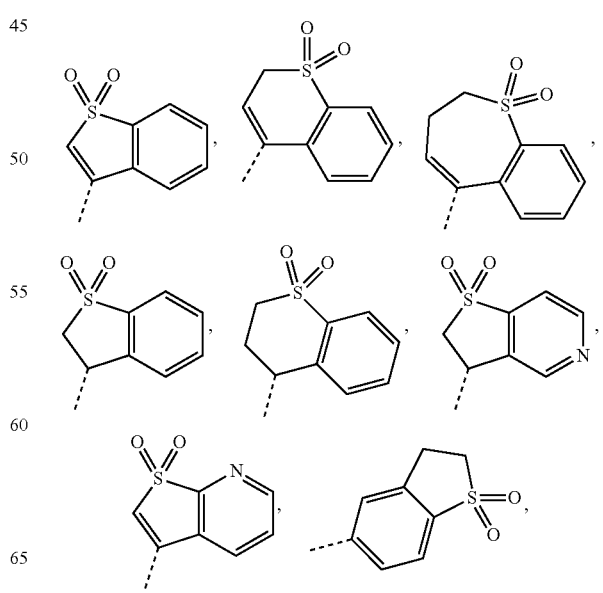

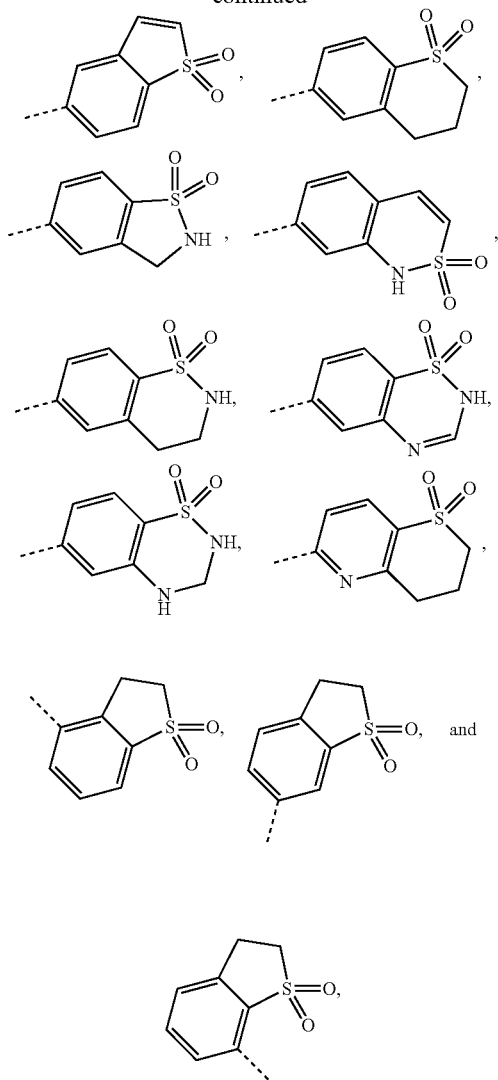

which are optionally substituted with one or more $R_1$.

In some embodiments of the present application, each $R_3$ is independently selected from the group consisting of H, F, Cl, Br, I, —OH, and —NO$_2$; or is independently selected from the following groups: —NH$_2$, Me, Et, formamido, and cyclopropylcarboxamido, which are optionally substituted with 1, 2, or 3 R.

In some embodiments of the present application, each $R_3$ is independently selected from the group consisting of H, F, Cl, Br, I, —OH, —NO$_2$, —NH$_2$, Me, —CF$_3$, formamido, and cyclopropylcarboxamido.

In some embodiments of the present application, each $R_3$ is independently selected from the group consisting of H, F, Cl, Br, Me, —CF$_3$, —NO$_2$, formamido, and cyclopropylcarboxamido.

In some embodiments of the present application, L is selected from the group consisting of a single bond, —CH$_2$—, and —CH(CH$_3$)—.

In some embodiments of the present application, the compound represented by formula (I) is a compound represented by formula (II),

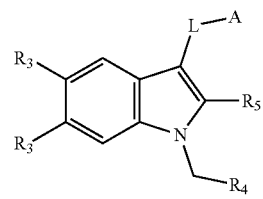

(II)

wherein $R_3$, $R_4$, $R_5$, L and A are defined as in formula (I), and L may be attached to any position of A other than the —S(=O)$_2$— moiety that satisfies the valence requirement.

In some embodiments of the present application, the compound represented by formula (I) is a compound represented by formula (III),

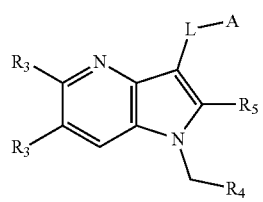

(III)

wherein $R_3$, $R_4$, $R_5$, L and A are defined as in formula (I), and L may be attached to any position of A other than the —S(=O)$_2$— moiety that satisfies the valence requirement.

In some embodiments of the present application, the compound represented by formula (I) is a compound represented by formula (IV),

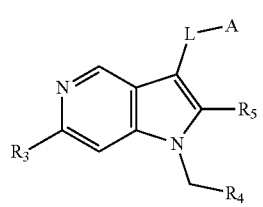

(IV)

wherein $R_3$, $R_4$, $R_5$, L and A are defined as in formula (I), and L may be attached to any position of A other than the —S(=O)$_2$— moiety that satisfies the valence requirement.

In some embodiments of the present application, the compound represented by formula (I) is a compound represented by formula (V),

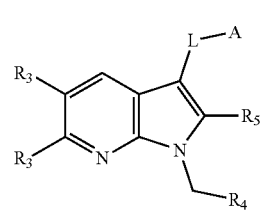

(V)

wherein $R_3$, $R_4$, $R_5$, L and A are defined as in formula (I), and L may be attached to any position of A other than the —S(=O)$_2$— moiety that satisfies the valence requirement.

In some embodiments of the present application, the compound represented by formula (I) is a compound represented by formula (VI),

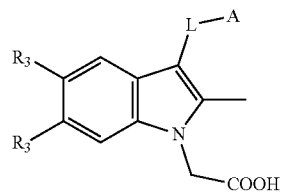

(VI)

wherein $R_3$, L and A are defined as in formula (I), and L may be attached to any position of A other than the —S(=O)$_2$— moiety that satisfies the valence requirement.

In some embodiments of the present application, the compound represented by formula (I) may be selected from the group consisting of:

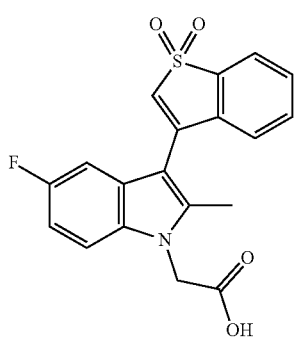

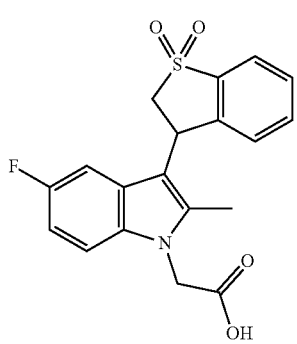

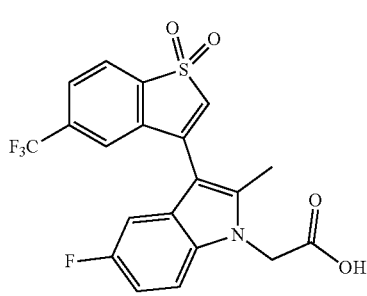

-continued

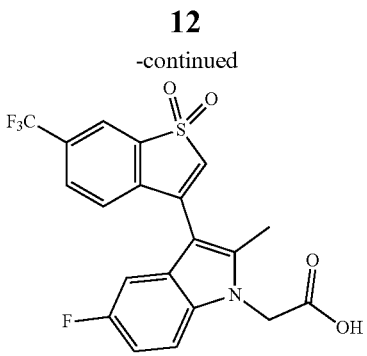

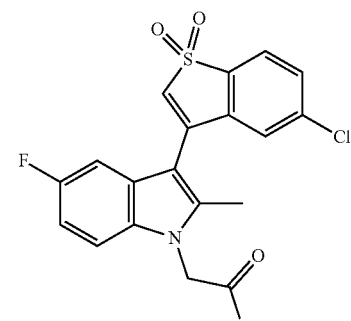

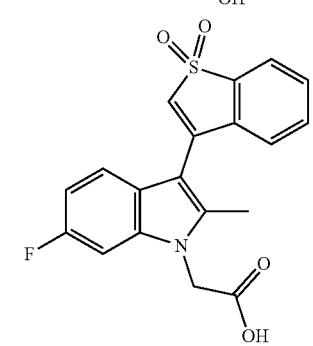

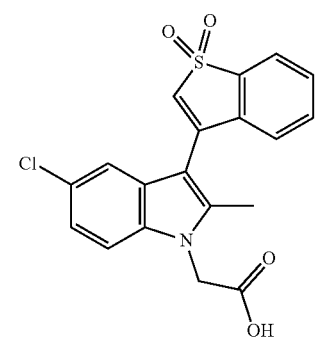

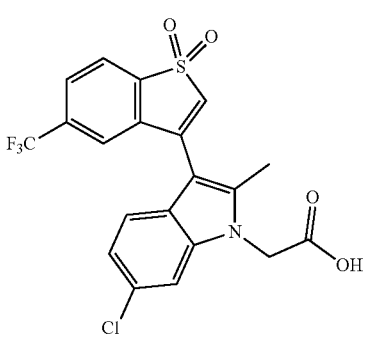

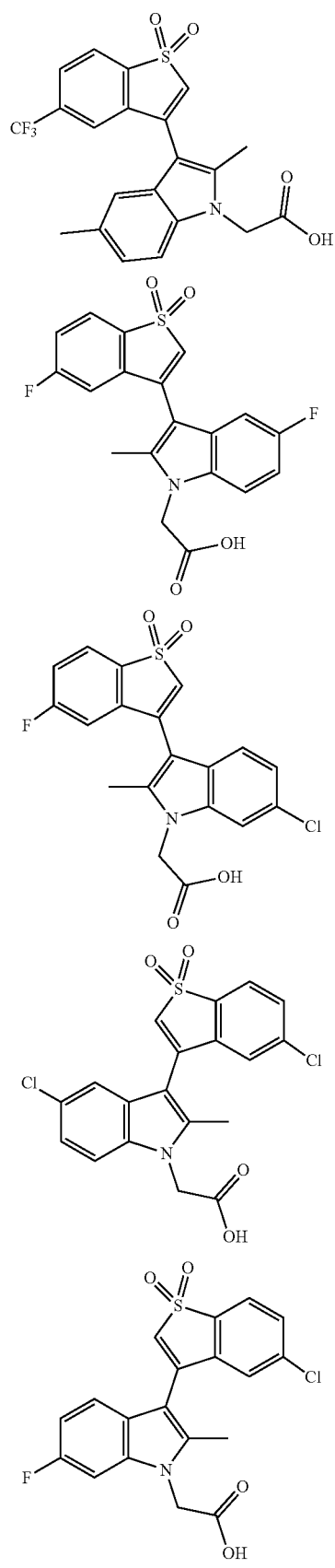
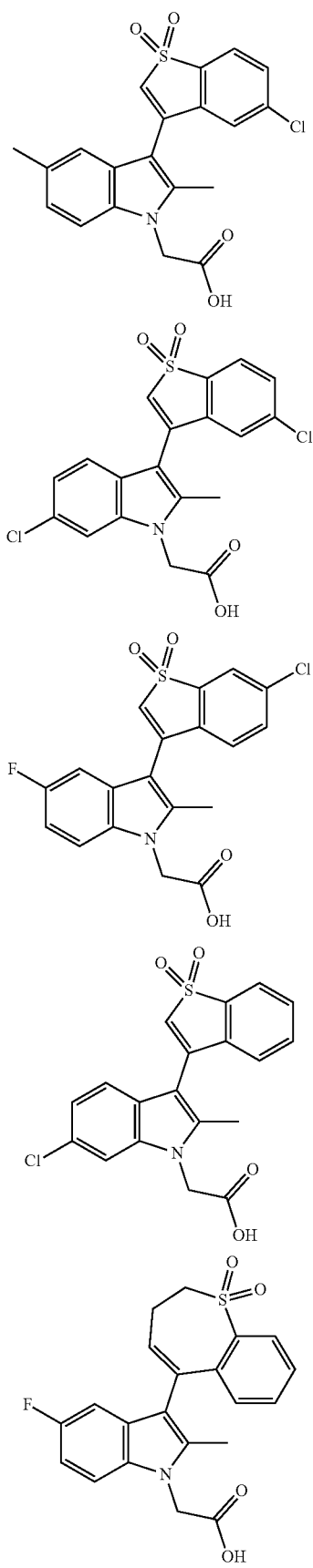

-continued
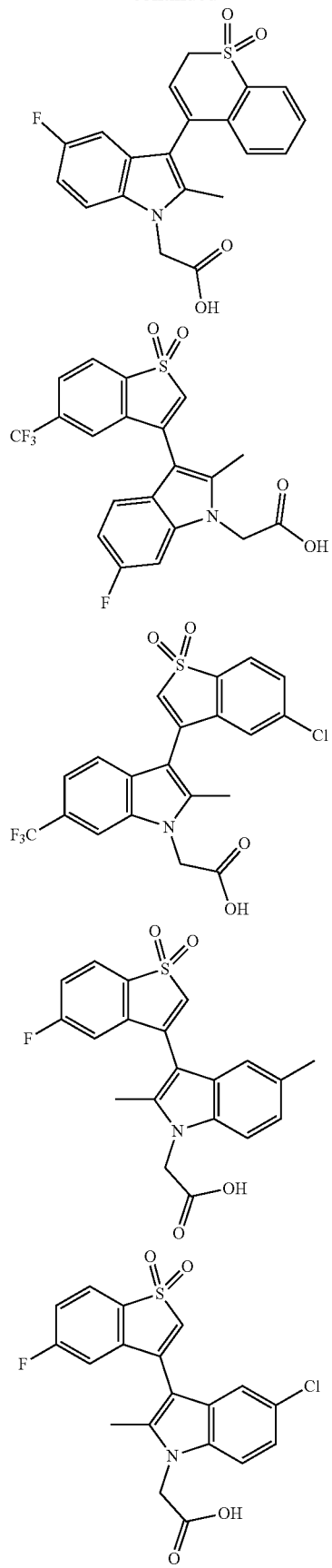
-continued
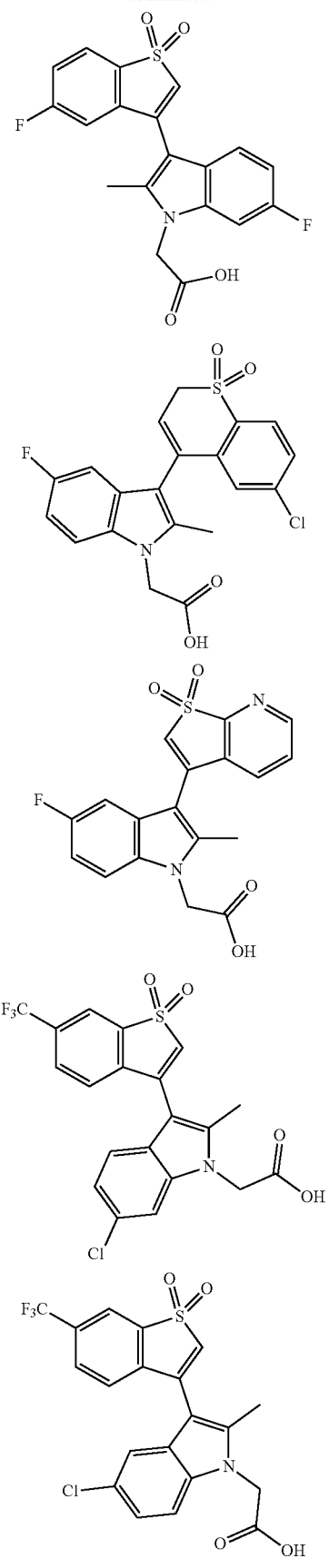

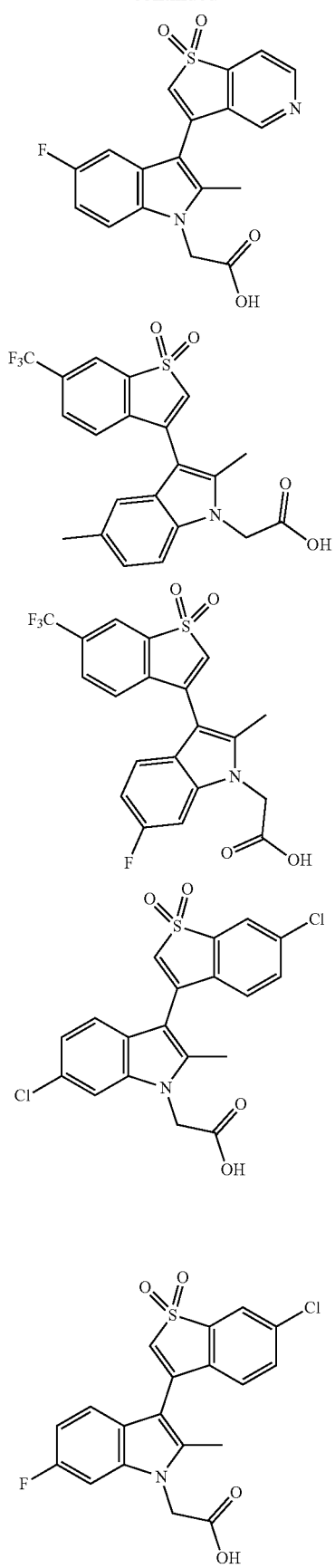
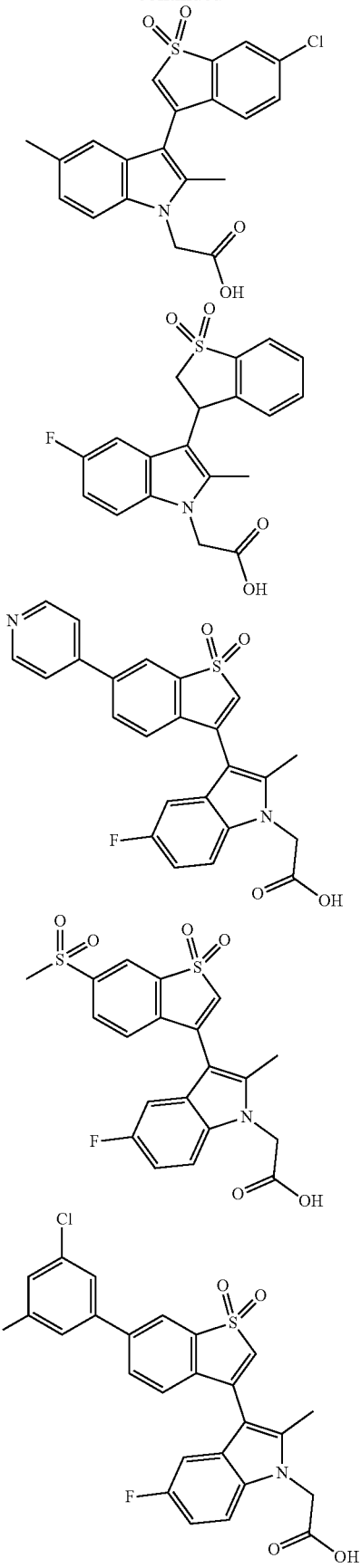

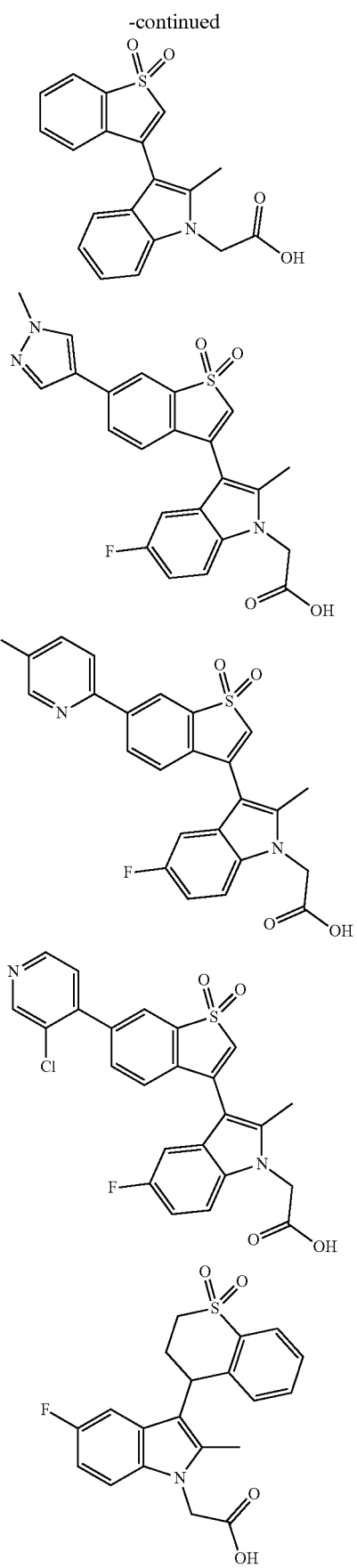
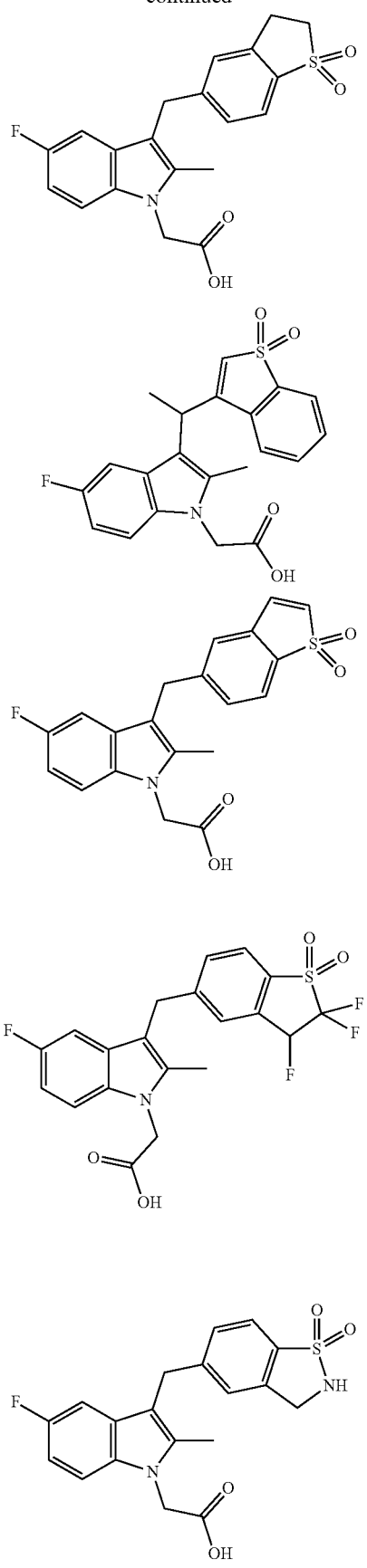

-continued
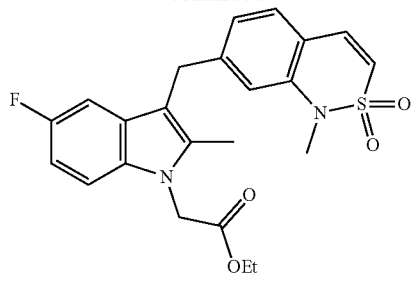
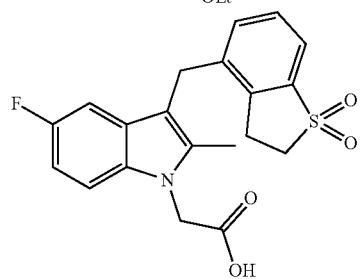
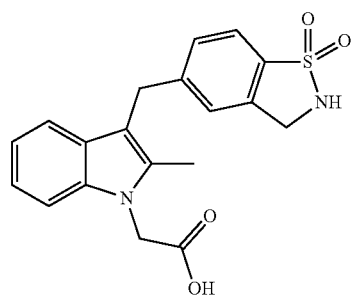
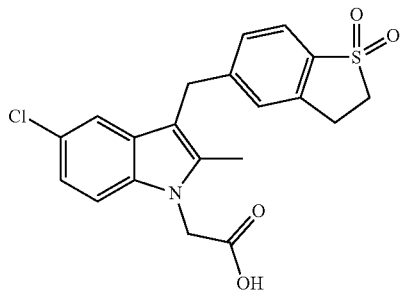
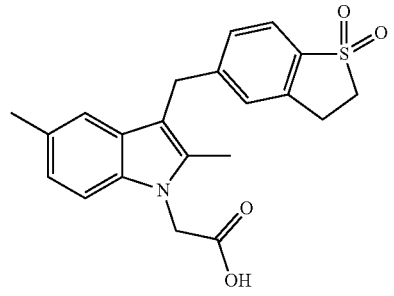
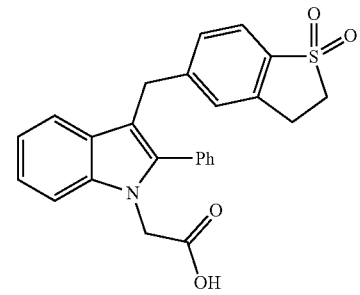
-continued
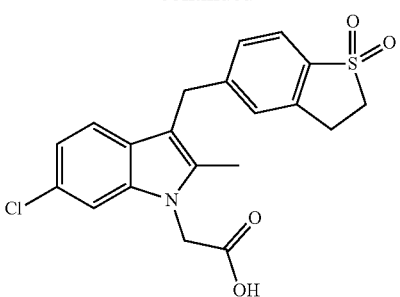
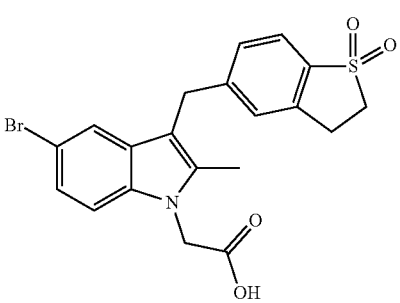
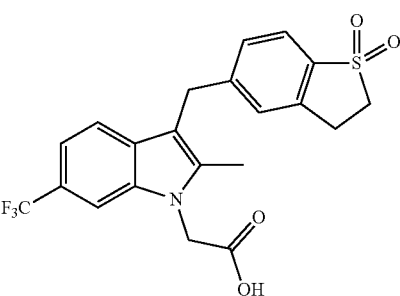
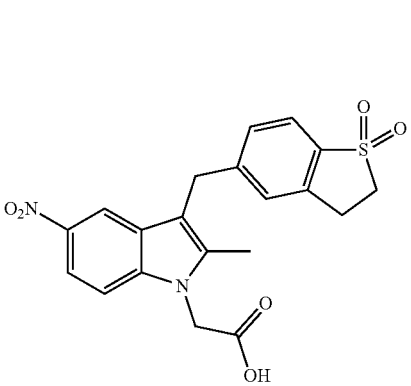
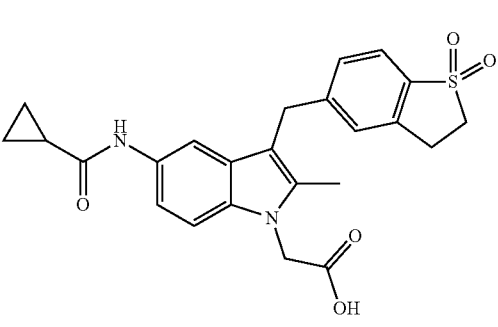

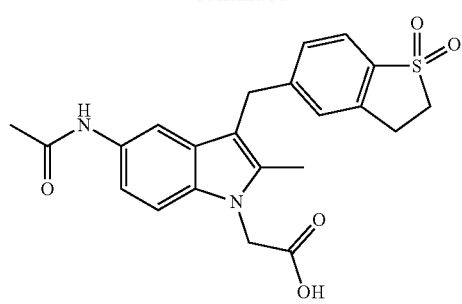
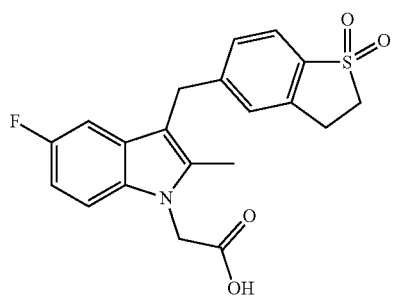
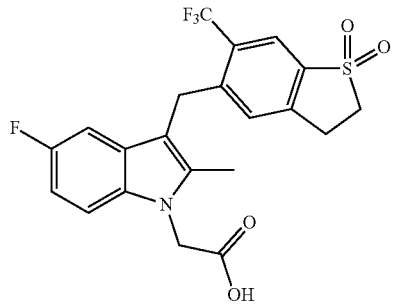
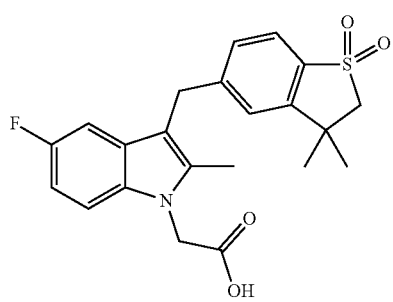
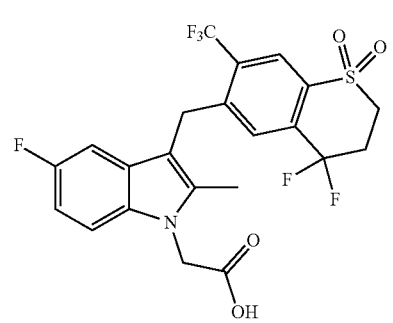
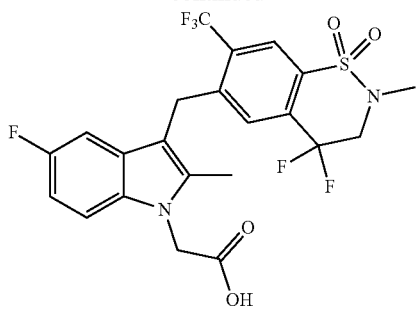
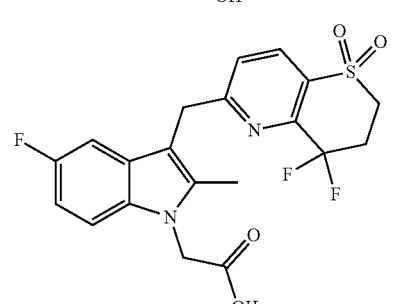
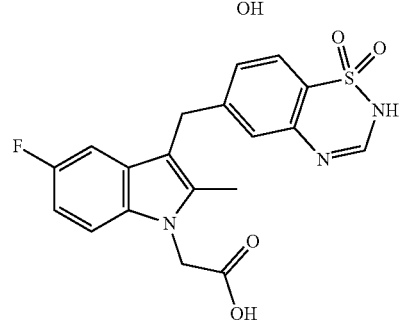
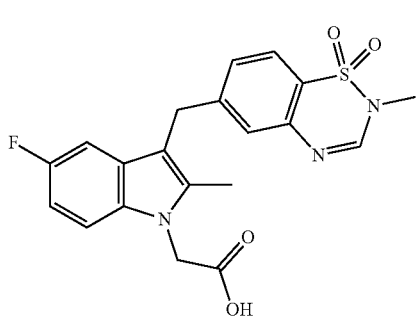
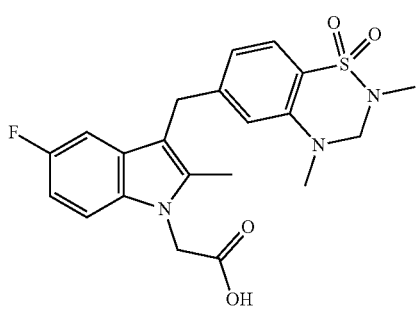

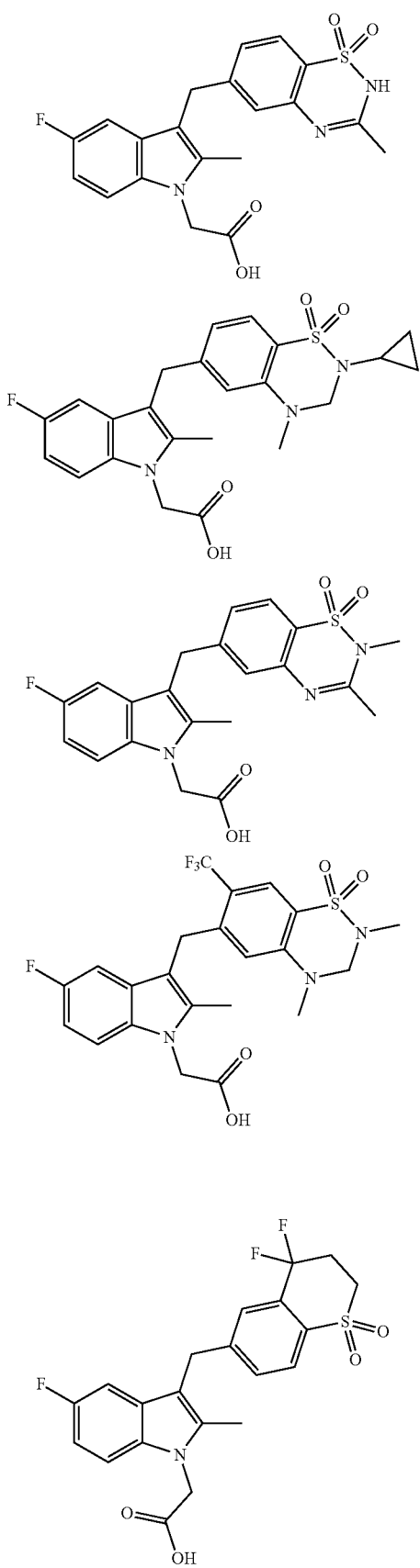
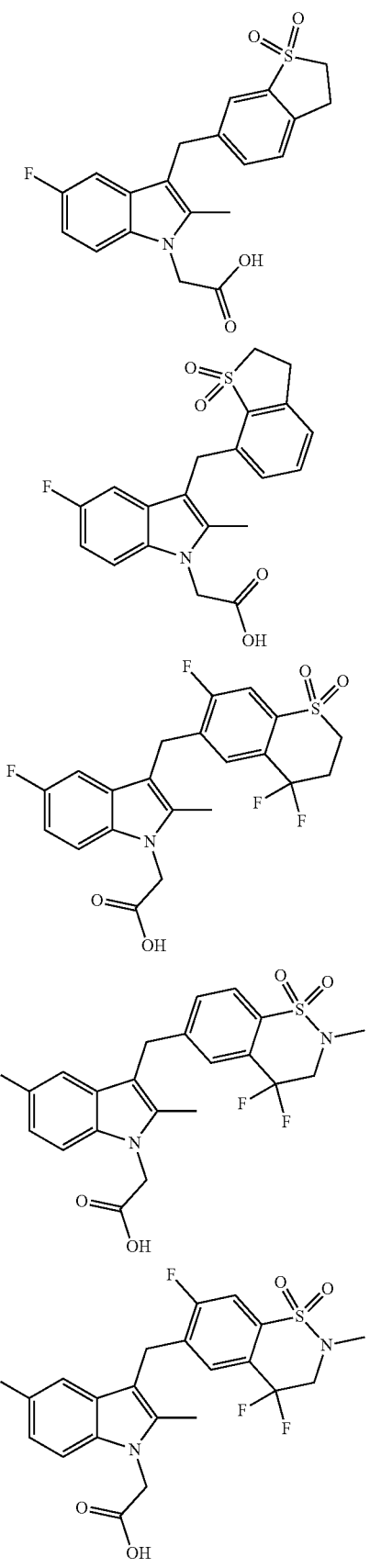

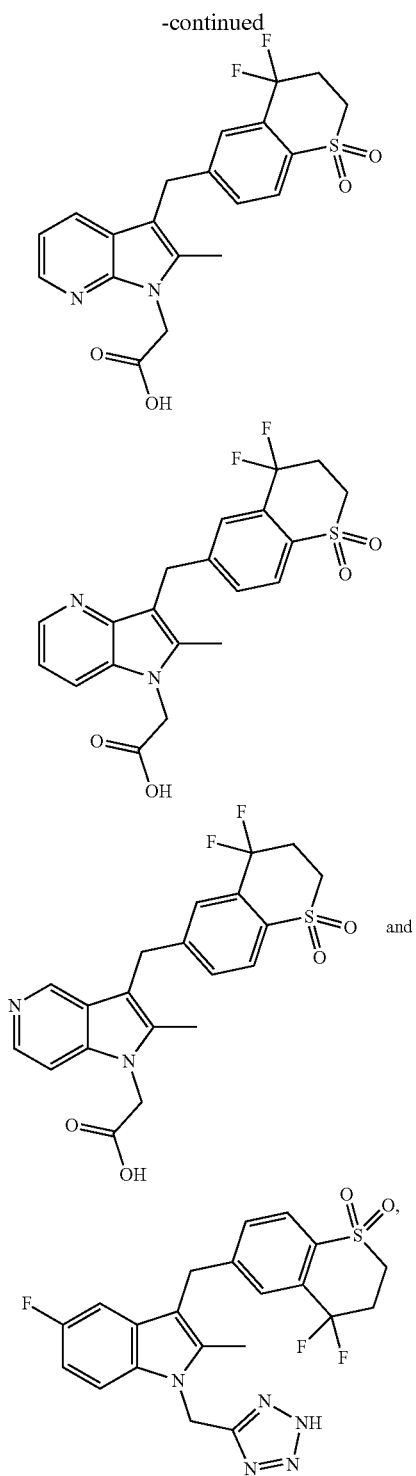

or a pharmaceutically acceptable salt thereof, or a tautomer thereof, or a solvate thereof.

In another aspect, the present application provides a pharmaceutical composition, comprising a compound represented by formula (I) of the present application, or a pharmaceutically acceptable salt thereof, or a tautomer thereof, or a solvate thereof. In some embodiments, the pharmaceutical composition of the present application further comprises a pharmaceutically acceptable adjuvant.

In another aspect, the present application provides a method for treating a disease mediated by a CRTH2 receptor in a mammal, comprising administering to a mammal, preferably a human, in need thereof a therapeutically effective amount of a compound represented by formula (I), or a pharmaceutically acceptable salt thereof, or a tautomer thereof, or a solvate thereof, or a pharmaceutical composition thereof.

In still another aspect, the present application relates to use of a compound represented by formula (I), or a pharmaceutically acceptable salt thereof, or a tautomer thereof, or a solvate thereof, or a pharmaceutical composition thereof in the preparation of a medicament for preventing or treating a disease mediated by a CRTH2 receptor.

In yet another aspect, the present application relates to a compound represented by formula (I), or a pharmaceutically acceptable salt thereof, or a tautomer thereof, or a solvate thereof, or a pharmaceutical composition thereof for use in preventing or treating a disease mediated by a CRTH2 receptor.

In some embodiments of the present application, the disease associated with a CRTH2 receptor is preferably an allergic disease, e.g., asthma and allergic rhinitis.

Definitions and Description; Unless otherwise indicated, the following terms and phrases as used herein are intended to have the following meanings. A particular term or phrase without a particular definition should not be regarded as being indefinite or unclear, but should be understood in its ordinary sense. When a tradename is used herein, it is intended to refer to the corresponding commodity or its active ingredient.

The term "pharmaceutically acceptable" means those compounds, materials, compositions and/or dosage forms, within the scope of reliable medical judgment, are suitable for use in contact with the tissues of humans and animals without excessive toxicity, irritation, allergic reactions or other problems or complications, while being commensurate with a reasonable benefit/risk ratio.

The term "pharmaceutically acceptable salt" refers to the salt of the compound of the present application, which is prepared from the compound with specific substituents discovered by the present application and a relatively non-toxic acid or base. When the compound of the present application contains a relatively acidic functional group, a base addition salt can be obtained by contacting the compound with a sufficient amount of a base. The pharmaceutically acceptable base addition salt includes the salt of sodium, potassium, calcium, ammonium, organic ammonium or magnesium or the like. When the compound of the present application contains a relatively alkaline functional group, an acid addition salt can be obtained by contacting the compound with a sufficient amount of an acid. Examples of the pharmaceutically acceptable acid addition salt include an inorganic acid salt, wherein the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid, etc.; and an organic acid salt, wherein the organic acid includes such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluene sulfonic acid, citric acid, tartaric acid, methylsulfonic acid and the like; and also includes a salt of an amino acid (e.g. arginine), and a salt of an organic acid such as glucuronic acid and the like (see Berge et al., "Pharmaceutical Salts", *Journal of Pharmaceutical Science* 66: 1-19

(1977)). Some specific compounds of the present application contain alkaline and acidic functional groups so as to be able to be converted to any base addition salts or acid addition salts.

Preferably, the parent form of a compound is regenerated by contacting a salt with a base or an acid in a conventional manner and then separating the parent compound. The differences between a parent form of a compound and the various salt forms thereof lie in some physical properties. For example, the solubilities in a polar solvent are different.

The "pharmaceutically acceptable salt" as used herein belongs to the derivatives of the compound of the present application, wherein the parent compound is modified by being salified with an acid or base. Examples of the pharmaceutically acceptable salt include but not limited to: an inorganic or organic acid salt of a base (such as amine), an alkali metal or organic salt of an acid (such as carboxylic acid), and so on. The pharmaceutically acceptable salt includes common non-toxic salts or quaternary ammonium salts of the parent compound, such as a salt formed by a non-toxic inorganic or organic acid. The common non-toxic salts include but not limited to those salts derived from inorganic acids and organic acids, wherein the inorganic acids or organic acids are selected from 2-acetoxybenzoic acid, 2-isethionic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptonic acid, gluconic acid, glutamic acid, glycolic acid, hydrobromic acid, hydrochloric acid, hydriodate, hydroxynaphthoic acid, isethionic acid, lactic acid, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonic acid, propionic acid, salicylic acid, stearic acid, subacetic acid, succinic acid, aminosulfonic acid, sulfanilic acid, sulphuric acid, tannic acid, tartaric acid and p-toluene sulfonic acid.

The pharmaceutically acceptable salt of the present application can be synthesized with a parent compound containing an acidic or alkaline group by a conventional chemical method. Generally, the preparation method of the salt comprises: reacting these compounds in the forms of free acids or bases with a stoichiometric amount of proper bases or acids in water or an organic solvent or a water-organic solvent mixture. In general, a non-aqueous media such as ether, ethyl acetate, ethanol, isopropanol or acetonitrile is preferable.

Some compounds of the present application may exist in non-solvate or solvate forms, including hydrate forms. In general, the solvate form is similar to the non-solvate form, both of which are included within the scope of the present application.

The compound of the present application may exist in the form of a specific geometric or stereoisomeric isomer. The present application envisages all of these compounds, including tautomers, cis- and trans-isomers, (−)- and (+)-enantiomers, (R)- and (S)-enantiomers, diastereomers, (D)-isomers, (L)-isomers, as well as racemic mixtures and other mixtures, such as enantiomer- or diastereoisomer-enriched mixtures, all of these isomers and mixtures are included within the scope of the present application. Other asymmetric carbon atoms may exist in substituents such as alkyl. All of these isomers and their mixtures are included within the scope of the present application.

Optically active (R)- and (S)-isomers and (D)- and (L)-isomers can be prepared by asymmetric synthesis or chiral reagents or other conventional techniques. An enantiomer of a compound of the present application can be prepared by asymmetric synthesis or the derivatization action with chiral auxiliaries, in which the resulting diastereomer mixtures are isolated, and the auxiliary groups are cleaved to provide the desired pure enantiomer. Alternatively, when a molecule contains an alkaline functional group (such as amino) or an acidic functional group (such as carboxyl), the molecule is reacted with an appropriate optical active acid or base to form a diastereomer salt, the diastereomer is resoluted by well-known conventional methods in the art, and then pure enantiomers can be obtained. In addition, the separation of enantiomers and diastereomers is usually realized by chromatography, which employs a chiral stationary phase, and optionally is combined with the chemical derivatization method (e.g. a carbamate is generated from an amine).

The compound of the present application may comprise unnatural proportion of atomic isotopes at one or more atoms that constitute the compound. For example, the compound can be labeled by a radioactive isotope, such as tritium ($^3H$), iodine-125($^{125}I$) or C-14($^{14}C$). All the variants composed by isotopes of the compound disclosed in the present application, whether radioactive or not, are included within the scope of the present application.

The term "a pharmaceutically acceptable carrier" refers to any formulation or carrier medium which is capable of delivering an effective amount of the active substance disclosed in the present application, does not interfere with the biological activity of the active substance, and has no toxic side-effects on a host or patient. Representative carriers include water, oil and minerals, cream base, lotion matrix, ointment matrix, etc. These matrixes include suspensions, suspending agent, viscosity increasers, transdermal enhancers, etc. Other information about the carrier can refer to *Remington: The Science and Practice of Pharmacy*, 21st Ed., Lippincott, Williams & Wilkins (2005), the content of which is incorporated herein by reference.

The term "adjuvant" usually refers to a carrier, diluent and/or medium required for the preparation of an effective pharmaceutical composition.

For a drug or pharmacological active agent, the term "effective amount" or "therapeutically effective amount" refers to a sufficient amount of a drug or formulation that can achieve desired effects but is non-toxic. The determination of an effective amount varies from person to person, depending on the age and general condition of a subject, and also depending on the specific active substance. An appropriate effective amount in individual cases can be determined by the person skilled in the art according to conventional tests.

The term "active ingredient", "therapeutic agent", "active substance" or "active agent" refers to a chemical entity, which can effectively treat a target disorder, disease or condition.

"Optional" or "optionally" means that the subsequently described event or circumstance may but does not have to occur, and that the description includes instances where the event or circumstance occurs and instances where it does not. The term "substituted" refers to one or more hydrogen atoms on a specific atom are substituted by a substituent, including deuterium and variants of hydrogen, as long as the valence state of the specific atom is normal and the compound obtained after substitution is stable. The term "optionally substituted" means that it may be substituted or not be substituted, and unless otherwise specified, the type and number of substituents can be arbitrary under the premise that it can be achieved in chemistry.

When any variable (e.g. R) occurs more than one time in the composition or structure of a compound, the definition in each occurrence is independent. Therefore, for example, if a group is substituted by 0-2 R, the group may optionally be substituted by at most two R, and R in each case has an independent option. In addition, the combination of substituents and/or their variants is allowed only if such a combination will lead to a stable compound.

When the number of a linking group is 0, e.g., —(CR$_9$R$_9$)$_0$—, it means that the linking group is a single bond.

When one of the variables is a single bond, it means that the two groups connected thereto are directly connected to each other. For example, when L in A-L-Z represents a single bond, it means that the structure is actually A-Z.

When a substituent is absent, it means that the substituent is not present. For example, when X in A-X is absent, it means that the structure is actually A. When the bonds of a substituent are cross-connected to two atoms on a ring, the substituent can be bonded with any atom on the ring. When the atom, through which an enumerated substituent is connected to a compound that is included in the general formula of a chemical structure but is not specifically mentioned, is not designated, the substituent can be bonded with any atom thereof. The combination of substituents and/or their variants is allowed only if such a combination will lead to a stable compound. For example, a structural unit

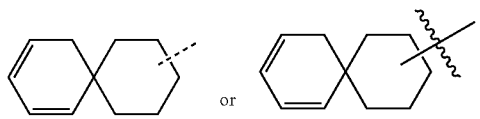

means that it may be substituted at any position on cyclohexyl or cyclohexadiene.

Unless otherwise specified, the term "hetero" represents a heteroatom or a heteroatom group (i.e. a group containing a heteroatom), including atoms except for carbon (C) and hydrogen (H) and groups containing these heteroatoms, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and optionally substituted —C(=O)N(H)—, —N(H)—, —C(=NH)—, —S(=O)$_2$N(H)— or —S(=O)N(H)—.

Unless otherwise specified, the term "ring" includes a single ring, a linked ring, a spiro ring, a fused ring or a bridged ring. The number of the atoms in the ring is usually defined as the number of the members forming the ring, for example, "5- to 7-membered ring" refers to a ring formed by 5 to 7 atoms. Unless otherwise specified, the ring optionally contains 1-3 heteroatoms. Therefore, "5- to 7-membered ring" includes, for example, phenyl, pyridinyl and piperidinyl; on the other hand, the term "5- to 7-membered heterocyclyl" includes pyridyl and piperidinyl, but does not include phenyl. The term "ring" also includes a ring system containing at least one ring, wherein each "ring" independently meets the above definition.

Unless otherwise specified, the term "heterocycle" or "heterocyclyl" refers to a stable monocyclic, bicyclic or tricyclic ring containing a heteroatom or a heteroatom group, they may be saturated, partially unsaturated or unsaturated (aromatic), and they contain carbon atoms and 1, 2, 3 or 4 heteroatoms which are independently selected from the group consisting of N, O and S, wherein any of the above-mentioned heterocycle may be fused to a benzene ring to form a bicyclic ring. Nitrogen atoms and sulfur atoms may be optionally oxidized (i.e., NO and S(O)$_p$, p is 1 or 2). The nitrogen atoms may be substituted or unsubstituted (i.e. N or NR, wherein R is H or other substituents that have been defined herein). The heterocycle may be attached to the side group of any heteroatoms or carbon atoms to form a stable structure. If the formed compound is stable, the heterocycle described herein may be substituted on its carbon or nitrogen atoms. The nitrogen atoms in the heterocycle are optionally quaternized. A preferred embodiment is, when the total number of S and O atoms in the heterocycle is more than 1, these heteroatoms are not adjacent to each other. Another preferred embodiment is the total number of S and O atoms in the heterocycle is not more than 1. As used herein, the term "aromatic heterocyclic group" or "heteroaryl" refers to a stable 5-, 6-, 7-membered monocyclic or bicyclic or 7-, 8-, 9- or 10-membered bicyclic aromatic heterocyclyl, which contains carbon atoms and 1, 2, 3 or 4 heteroatoms which are independently selected from the group consisting of N, O and S. The nitrogen atoms may be substituted or unsubstituted (i.e. N or NR, wherein R is H or other substituents that have been defined herein). Nitrogen atoms and sulfur atoms may be optionally oxidized (i.e., NO and S(O)$_p$, p is 1 or 2). It is worth noting that, the total number of S and O atoms in the aromatic heterocycle is not more than 1. Bridged rings are also included in the definition of the heterocycle. When one or more atoms (i.e. C, O, N, or S) are connected to two nonadjacent carbon atoms or nitrogen atoms, a bridged ring is formed. It is worth noting that, a bridge always converts a monocyclic ring into a tricyclic ring. In the bridged ring, the substituent in the ring may also locate on the bridge.

Examples of heterocyclyl include but not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl, decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isobenzofuranyl, isoindolyl, isoindolinyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidyl, phenanthridinyl, phenanthrolinyl, phenazinyl, phenothiazinyl, benzoxanthinyl, phenoxazinyl, phthalazinyl, piperazinyl, piperidyl, piperidonyl, 4-piperidonyl, piperonyl, pteridyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrrolidinyl, pyrrolinyl, 2H-pyrrolyl, pyrrolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienoxazolyl, thienothiazolyl, thienoimidazolyl, thienyl, triazinyl, 1,2,3-triazolyl, 1,2,4-triazolyl, 1,2,5-triazolyl, 1,3,4-triazolyl and xanthenyl. Fused-ring and spiro-ring compounds are also included.

Unless otherwise specified, the term "hydrocarbyl" or its specific terms (such as alkyl, alkenyl, alkynyl, aryl and so on) themself or as a part of another substituent represent a linear, branched or cyclic hydrocarbon group or a combination thereof, which may be completely saturated (such as alkyl), or mono- or poly-unsaturated (such as alkenyl, alkynyl and aryl), may be monosubstituted or multisubstituted, may be monovalent (e.g., methyl), divalent (e.g., methylene) or multivalent (e.g., methine), may include bivalent or multivalent atomic groups, and have a specified number of carbon atoms (for example, $C_1$-$C_{12}$ represents 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$, and $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes but not limited to aliphatic hydrocarbyl and aromatic hydrocarbyl. The aliphatic hydrocarbyl includes linear and cyclic aliphatic hydrocarbyl, and specifically includes but not limited to alkyl, alkenyl and alkynyl. The aromatic hydrocarbyl includes but not limited to 6- to 12-membered aromatic hydrocarbyl, such as phenyl, naphthyl and the like. In some embodiments, the term "hydrocarbyl" represents a linear or branched atomic group or a combination thereof, which may be completely saturated, or mono- or poly-unsaturated, and may include divalent and polyvalent groups. Examples of saturated hydrocarbon groups include but not limited to homologues or isomers of methyl, ethyl, n-propyl, iso-propyl, n-butyl, tert-butyl, iso-butyl, sec-butyl, cyclohexyl, (cyclohexyl)methyl, cyclopropyl methyl, and n-amyl, n-hexyl, n-heptyl, n-octyl and the like. Unsaturated hydrocarbyl has one or more double bonds or triple bonds, and its examples include but not limited to vinyl, 2-propenyl, butenyl, crotyl, 2-isopentenyl, 2-butadienyl, 2,4-pentadienyl, 3-(1,4-pentadienyl), acetenyl, 1-propinyl and 3-propinyl, 3-butynyl, and the like.

Unless otherwise specified, the term "heterohydrocarbyl" or its specific terms (such as heteroalkyl, heteroalkenyl, heteroalkynyl, heteroaryl and the like) themself or combining with another term represents a stable linear, branched or cyclic hydrocarbon group or a combination thereof, which consists of a certain number of carbon atoms and at least one heteroatom. In some embodiments, the term "heteroalkyl" itself or combining with another term represents a stable linear, or branched hydrocarbon group or a combination thereof, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atoms are optionally quaternized. Heteroatoms or heteroatom groups may be located in any internal positions of the heterohydrocarbyl, including the position where the hydrocarbyl is attached to the rest part of the molecule. However, the terms "alkoxy", "alkylamino" and "alkylthio" (or thioalkoxy) belong to customary expressions, and refer to those alkyl groups which are attached to the rest of a molecular via an oxygen atom, an amino group or a sulfur atom, respectively. Examples include but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. At most two heteroatoms may be adjacent, such as —$CH_2$—NH—$OCH_3$.

Unless otherwise specified, the terms "cyclohydrocarbyl", "heterocyclohydrocarbyl" or specific terms thereof (such as aryl, heteroaryl, cycloalkyl, heterocycloalkyl, cycloalkenyl, heterocycloalkenyl, cycloalkynyl, heterocycloalkynyl and the like) themself or combining with other terms respectively represent a cyclic "hydrocarbyl" or "heterohydrocarbyl". In addition, in terms of heterohydrocarbyl or heterocyclohydrocarbyl (such as heteroalkyl and heterocycloalkyl), heteroatoms may occupy the position where the heterocyclic ring is attached to the rest part of the molecule. Examples of cyclohydrocarbyl include but not limited to cyclopentyl, cyclohexyl, 1-cyclohexenyl, 3-cyclohexenyl, cycloheptyl, etc. Non-limited examples of heterocyclohydrocarbyl include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophen-2-yl, tetrahydrothiophen-3-yl, 1-piperazinyl and 2-piperazinyl.

Unless otherwise specified, the term "alkyl" refers to a straight or branched saturated hydrocarbyl, which may be monosubstituted (e.g., —$CH_2F$) or multisubstituted (e.g., —$CF_3$), and may be monovalent (e.g., methyl), divalent (e.g., methylene) or multivalent (e.g., methine). Examples of alkyl include methyl (Me), ethyl (Et), propyl (e.g., n-propyl and isopropyl), butyl (e.g., n-butyl, isobutyl, s-butyl, and t-butyl), pentyl (e.g., n-pentyl, isopentyl, and neopentyl), and the like.

Unless otherwise specified, cycloalkyl includes any stable monocyclic or polycyclic hydrocarbyl, in which any carbon atom is saturated. Cycloalkyl may be monosubstituted or multisubstituted, and may be monovalent, divalent or multivalent. Examples of cycloalkyl include, but are not limited to, cyclopropyl, norbornanyl, [2.2.2]dicyclooctane, [4.4.0]dicyclodecane, and the like.

Unless otherwise specified, the term "aryl" represents a polyunsaturated aromatic hydrocarbon substituent, which may be monosubstituted or multisubstituted, and may be monovalent, divalent or multivalent. It may be monocyclic or polycyclic (for example, 1-3 rings; wherein at least one ring is aromatic). They are fused together or connected covalently.

The term "heteroaryl" refers to an aryl containing 1 to 4 heteroatoms. In an exemplary embodiment, the heteroatom is selected from the group consisting of B, N, O, and S, in which the nitrogen and sulfur atoms are optionally oxidized, and the nitrogen atoms are optionally quaternized. The heteroaryl may be connected to the rest part of the molecule via a heteroatom. Non-limited examples of aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl.

The compound of the present application can be prepared through many synthetic methods which are well-known to the person skilled in the art, including the following specific embodiments, embodiments obtained by combining the specific embodiments with other chemical synthetic methods and the equivalent alternative methods which are well-known to the person skilled in the art. The preferred embodiments include but not limited to the examples of the present application.

The solvents used in the present application are commercially available. The following abbreviations are used in the present application: aq represents water; HATU represents O-(7-azabenzotriazol-1-yl)-N,N,N'N'-tetramethyluronium hexafluorophosphate; EDC represents N-(3-dimethylaminopropyl)-N'-ethyl carbodiimide hydrochloride; m-CPBA represents 3-chloroperbenzoic acid; eq represents equivalent, equal-quantitative; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; CBz represents benzyloxycarbonyl, which is an amino protecting group; BOC represents tert-butoxycarbonyl, which is an amino protecting group; HOAc represents acetic acid; NaCNBH$_3$ represents sodium cyanoborohydride; r.t. represents room temperature; O/N represents overnight; THF represents tetrahydrofuran; Boc$_2$O represents di-tert-butyl dicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFSI represents N-fluoro-N-(phenylsulfonyl)benzenesulfonamide; NCS represents 1-chloropyrrolidine-2,5-dione; n-Bu$_4$NF represents tetrabutylammonium fluoride; iPrOH represents 2-propanol; mp represents melting point; and LDA represents lithium diisopropylamide.

The compounds are named artificially or named by ChemDraw® software, and vendor directory names are used for the commercially available compounds.

EXAMPLES

The present application is illustrated in detail hereinafter in conjunction with the examples, which are not intended to limit the present application in any way. The present application has been described in detail herein, and the specific examples thereof are also disclosed. It will be apparent for those skilled in the art to make various changes and improvements of the examples of present application without departing from the spirit and scope of the present application.

Example 1

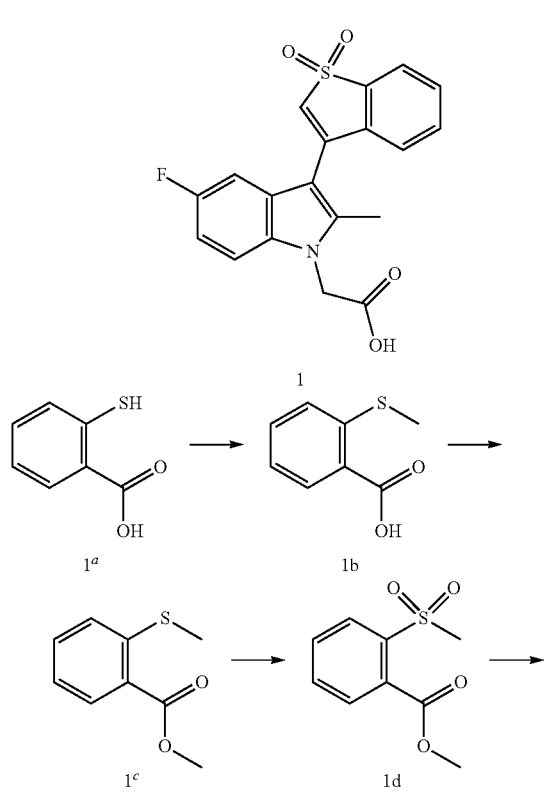

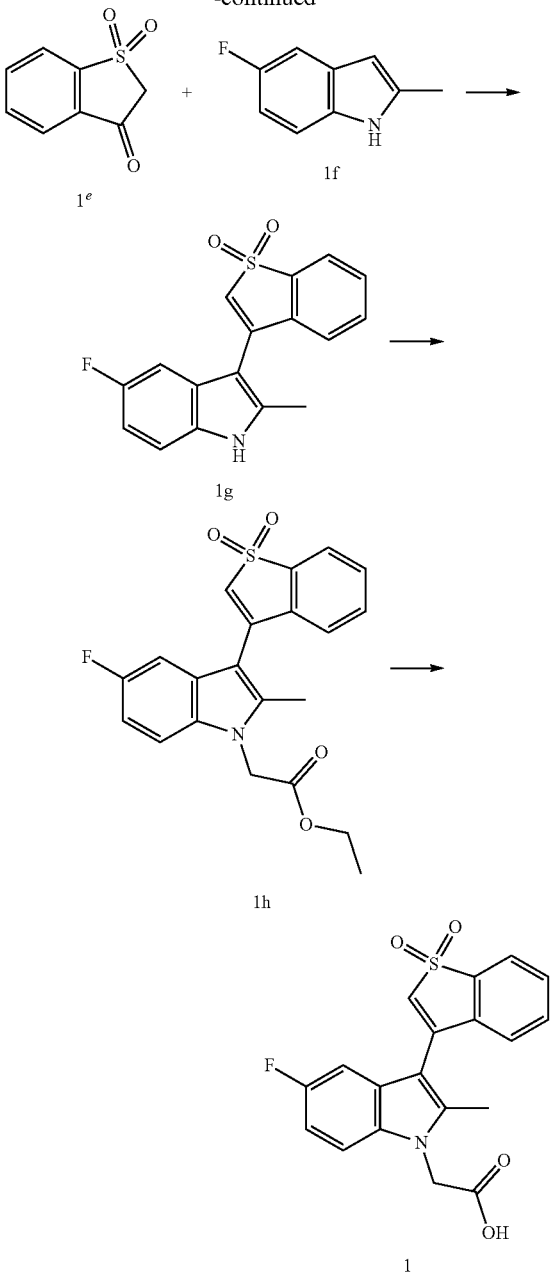

Step I

Compound 1a (50.00 g, 324.28 mmol) was dissolved in methanol (1 L), and a solution of sodium hydroxide (38.91 g, 972.84 mmol) in water (150 mL) was added. The resulting mixture was stirred for 15 min at 5-10° C., then iodomethane (80.54 g, 567.49 mmol) was added. The resulting reaction mixture was heated to reflux, and stirred for 16 hr. After the reaction mixture was concentrated to dryness, water (300 mL) was added, and the resulting mixture was adjusted with 1 N hydrochloric acid to pH 3-4. Precipitated solids were collected by filtration to give Compound 1b (51.00 g, yellowish solid, yield: 91%). $^1$H NMR (400 MHz, DMSO-d$_6$) δ 12.97 (br. s., 1H), 7.94-7.86 (m, 1H), 7.58-7.50 (m, 1H), 7.35 (d, J=8.0 Hz, 1H), 7.24-7.16 (m, 1H), 2.39 (s, 3H).

Step II

Compound 1b (51.00 g, 303.19 mmol) was dissolved in methanol (1 L), and sulfoxide chloride (108.21 g, 909.57 mmol) was added. The reaction mixture was heated to reflux, and stirred for 16 hr. The reaction mixture was concentrated to dryness, and dissolved in ethyl acetate (500 mL). The resulting mixture was washed with a saturated aqueous solution of sodium bicarbonate, and adjusted to pH 7. The organic phase was dried over anhydrous sodium sulfate, filtered, and concentrated under reduced pressure to dryness, to give Compound 1c (55.00 g, yellowish solid, 94%). $^1$H NMR (400 MHz, DMSO-$d_6$) δ 7.90 (d, J=7.6 Hz, 1H), 7.62-7.54 (m, 1H), 7.39 (d, J=8.4 Hz, 1H), 7.23 (t, J=7.6 Hz, 1H), 3.82 (s, 3H), 2.42 (s, 3H).

Step III

Compound 1c (55.00 g, 301.80 mmol) was dissolved in dichloromethane (1 L), and m-chloroperoxybenzoic acid (153.18 g, 754.50 mmol, 80%) was added at 0° C. The reaction mixture was stirred for 5 hr at 5-15° C., and then a saturated solution of sodium thiosulfate (150 mL) was added to quench the reaction. The resulting mixture was adjusted with a sodium carbonate solution to pH 8-9. The organic phase was further washed with a saturated aqueous solution of sodium bicarbonate (500 mL), dried over anhydrous sodium sulfate, filtered, and concentrated under reduced pressure to dryness, to give a crude product. The crude product was slurried in a mixed solvent of petroleum ether/ethyl acetate (200 mL, v/v=10/1), and filtered to give Compound 1d (62.90 g, white solid, 97%). $^1$H NMR (400 MHz, CDCl$_3$) δ 8.15-8.10 (m, 1H), 7.72-7.64 (m, 3H), 3.97 (s, 3H), 3.34 (s, 3H).

Step IV

Compound 1d (55.00 g, 256.72 mmol) was dissolved in tetrahydrofuran (1 L), and lithium bis(trimethylsilyl)amide (308.06 mmol, 1M, 308.06 mL) was slowly added dropwise at −78° C. The reaction mixture was warmed to 5-15° C. and stirred for 3 hr, and then water (500 mL) was added to quench the reaction. The resulting mixture was adjusted with 1 N hydrochloric acid solution to pH 6-7, and extracted with ethyl acetate (800 mL×2). The organic phase was dried over anhydrous sodium sulfate, filtered, and concentrated under reduced pressure to dryness, to give a crude product. The crude product was recrystallized with ethyl acetate (200 mL) to give Compound 1e (39.00 g, yellow solid, 74%). $^1$H NMR (400 MHz, CDCl$_3$) δ 8.06-7.99 (m, 2H), 7.99-7.93 (m, 1H), 7.87-7.81 (m, 1H), 4.11 (s, 2H).

Step V

Compound 1e (3.50 g, 23.46 mmol) and Compound 1f (4.28 g, 23.46 mmol) were dissolved in 1,2-dichloroethane (250 mL), and trifluoroacetic acid (70 mg, 0.62 mmol) was added. The reaction mixture was stirred for 16 hr at 50° C. The reaction mixture was washed with a saturated solution of sodium bicarbonate (250 mL), and extracted with dichloromethane (150 mL×2). The organic phases were combined, dried over anhydrous sodium sulfate, filtered, concentrated under reduced pressure to dryness, and separated and purified by flash silica gel column chromatography (petroleum ether/ethyl acetate 100-60%) to give Compound 1g (4.4 g, yellow solid, yield: 36%). MS-ESI calculated value [M+H]$^+$ 314, measured value 314.

Step VI

Compound 1g (4.40 g, 14.04 mmol) was dissolved in N,N-dimethylformamide (50 mL), and cesium carbonate (6.86 g, 21.06 mmol) was added, and ethyl bromoacetate (2.81 g, 16.85 mmol) was slowly added dropwise under stirring. The reaction mixture was stirred for 16 hr at 15-20° C., and then poured into water (300 mL), and the resulting mixture was extracted with ethyl acetate (150 mL×2). The organic phase was washed with saturated brine (200 mL), dried over anhydrous sodium sulfate, filtered, and concentrated under reduced pressure to dryness, to give Compound 1h (5.5 g, yellow solid, yield: 98%). $^1$H NMR (400 MHz, CDCl$_3$) δ 7.85-7.78 (m, 1H), 7.61-7.48 (m, 2H), 7.36 (d, J=7.2 Hz, 1H), 7.24-7.16 (m, 1H), 7.12-7.08 (m, 1H), 7.04-6.96 (m, 1H), 6.58 (s, 1H), 4.87 (d, J=3.2 Hz, 2H), 4.26 (q, J=7.2 Hz, 2H), 2.45 (s, 3H), 1.30 (t, J=7.2 Hz, 3H). MS-ESI calculated value [M+H]$^+$ 400, measured value 400.

Step VII

Compound 1h (1.60 g, 4.01 mmol) was dissolved in tetrahydrofuran (50 mL), and a solution of lithium hydroxide (840.40 mg, 20.03 mmol) in water (10 mL) was added. The reaction mixture was stirred for 2 hr at 25° C., neutralized by dropwise addition of 1N hydrochloric acid to pH 4-5, and extracted with ethyl acetate (30 mL×2). The organic phase was dried over anhydrous sodium sulfate, filtered, concentrated, and purified by a mixed solvent of petroleum ether/ethyl acetate (20 mL, v/v=2/1), to give Compound 1 (1.4 g, yield: 94%). $^1$H NMR (400 MHz, CD$_3$OD) δ 7.87-7.78 (m, 1H), 7.69-7.59 (m, 2H), 7.47-7.37 (m, 2H), 7.09-6.95 (m, 2H), 6.93 (s, 1H), 5.07 (d, J=2.4 Hz, 2H), 2.45 (s, 3H). MS-ESI calculated value [M+H]$^+$ 372, measured value 372.

Example 2

1h ⟶ 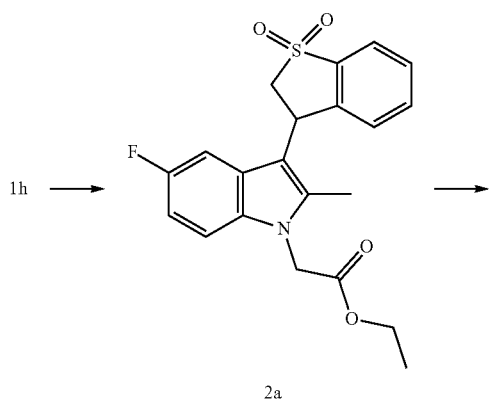 ⟶

2a

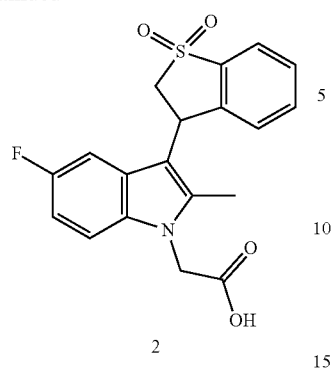

2

Step I

Compound 1h (1.50 g, 3.76 mmol) was dissolved in a mixed solvent of ethanol/ethyl acetate (150 mL, v/v=2/1), and wet palladium on carbon (150 mg, 10%, moisture content: 50%) was added. The reaction mixture was stirred under a hydrogen (15 psi) atmosphere for 16 hr at 25° C., and filtered through celite. The filtrate was concentrated to give Compound 2a (1.50 g, yellow solid, yield: 94%). $^1$H NMR (400 MHz, CDCl$_3$) δ 7.91-7.81 (m, 1H), 7.58-7.44 (m, 2H), 7.17-7.05 (m, 2H), 6.92-6.84 (m, 1H), 6.44 (br. s., 1H), 5.06 (t, J=8.4 Hz, 1H), 4.81 (s, 2H), 4.25 (q, J=7.2 Hz, 2H), 3.88-3.60 (m, 2H), 2.38 (br. s., 3H), 1.30 (t, J=7.2 Hz, 3H). MS-ESI calculated value [M+H]$^+$ 402, measured value 402.

Step II

Compound 2a (1.50 g, 3.74 mmol) was dissolved in tetrahydrofuran (50 mL), and a solution of lithium hydroxide (783.91 mg, 18.68 mmol) in water (10 mL) was added. The reaction mixture was stirred for 2 hr at 25° C., neutralized by dropwise addition of 1N hydrochloric acid to pH 4-5, and extracted with ethyl acetate (30 mL×2). The organic phase was dried over anhydrous sodium sulfate, filtered, concentrated, and purified by a mixed solvent of petroleum ether/ethyl acetate (20 mL, v/v=2/1), to give Compound 2 (1.30 g, yield: 89%). $^1$H NMR (400 MHz, CD$_3$OD) δ 7.89-7.79 (m, 1H), 7.64-7.53 (m, 2H), 7.31-7.23 (m, 1H), 7.21-7.11 (m, 1H), 6.89-6.75 (m, 1H), 6.37 (br. s., 1H), 5.19 (t, J=8.4 Hz, 1H), 4.95 (s, 2H), 4.04-3.94 (m, 1H), 3.64-3.54 (m, 1H), 2.40 (br. s., 3H). MS-ESI calculated value [M+H]$^+$ 374, measured value 374.

Example 3

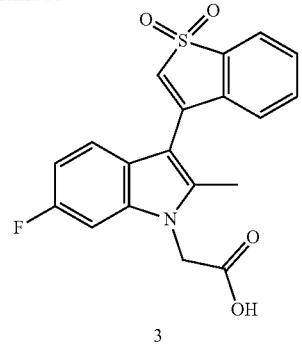

3

Compound 3 was synthesized from Compound 1e and Compound 3a according to the method in Example 1 (22 mg, yield: 35%). $^1$H NMR (400 MHz, CD$_3$OD) δ 7.82-7.80 (m, 1H), 7.67-7.55 (m, 2H), 7.42-7.40 (m, 1H), 7.36-7.30 (m, 1H), 7.22-7.16 (m, 1H), 6.90 (br.s., 2H), 5.02 (br.s., 2H), 2.43 (s, 3H). MS-ESI calculated value [M+H]$^+$ 372, measured value 372.

Example 4

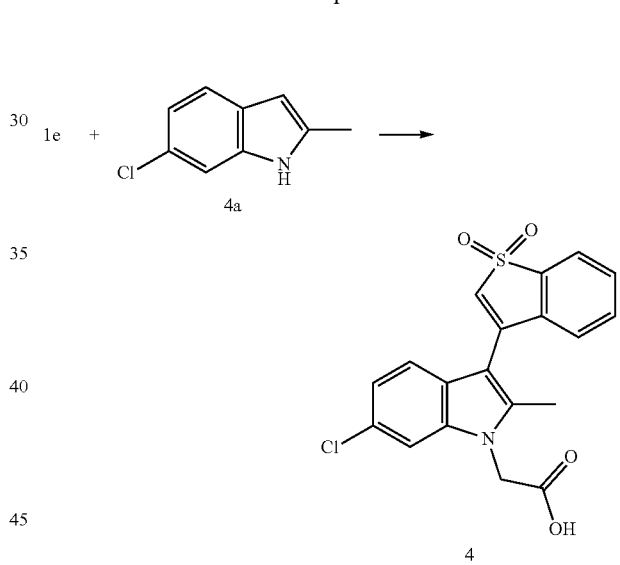

4

Compound 4 was synthesized from Compound 1e and Compound 4a according to the method in Example 1 (12 mg, yield: 34%). $^1$H NMR (400 MHz, CD$_3$OD) δ 7.86-7.79 (m, 1H), 7.70-7.56 (m, 2H), 7.48 (d, J=1.6 Hz, 1H), 7.44-7.38 (m, 1H), 7.36-7.34 (m, 1H), 7.13-7.07 (m, 1H), 6.94 (s, 1H), 5.06-5.05 (d, 2H), 2.45 (s, 3H). MS-ESI calculated value [M+H]$^+$ 388, measured value 388.

Example 5

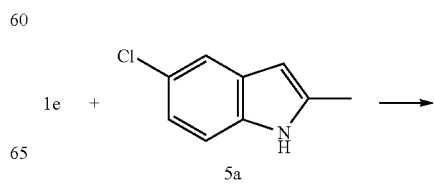

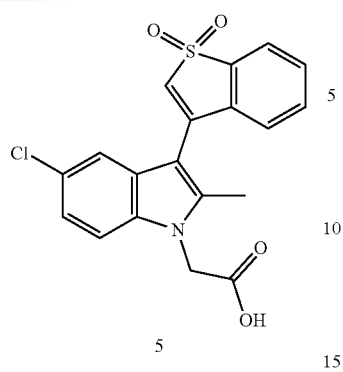

5

Compound 5 was synthesized from Compound 1e and Compound 5a according to the method in Example 1 (24 mg, yield: 39%). ¹H NMR (400 MHz, CD₃OD) δ 7.88-7.79 (m, 1H), 7.70-7.59 (m, 2H), 7.42-7.40 (m, 2H), 7.34-7.33 (m, 1H), 7.22-7.16 (m, 1H), 6.95 (s, 1H), 5.07-5.06 (m, 2H), 2.45 (s, 3H). MS-ESI calculated value [M+H]⁺ 388, measured value 388.

Example 6

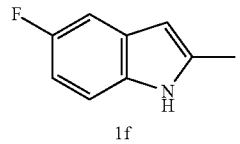 

1f

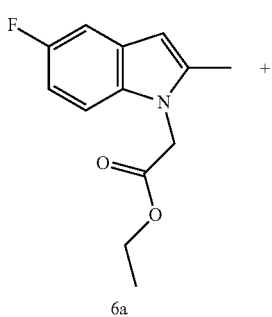

6a

+

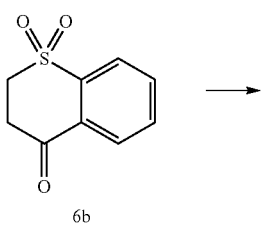 

6b

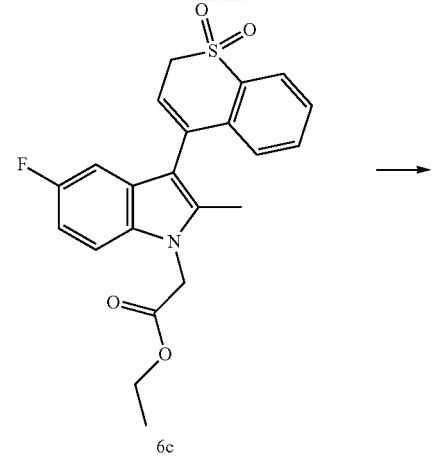

6c

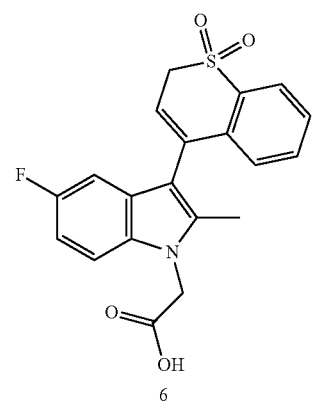

6

Step I

At room temperature, ethyl bromoacetate (13.44 g, 80.45 mmol) was added dropwise to a solution of Compound 1f (10.00 g, 67.04 mmol) and cesium carbonate (32.77 g, 100.56 mmol) in 100 mL of N,N-dimethylformamide. The reaction mixture was reacted for 3 hr at 60° C. After completion of the reaction, 200 mL of a saturated solution of sodium bicarbonate was added to the reaction mixture, and the resulting mixture was extracted with ethyl acetate (100 mL×3). The organic phase was washed with a saturated aqueous solution of sodium chloride, dried over anhydrous sodium sulfate, filtered, concentrated, and purified by silica gel column chromatography (petroleum ether/ethyl acetate 100-50%), to give the target Compound 6a (15.00 g, yellowish oil, yield: 95%). ¹H NMR (400 MHz, CDCl₃) δ 7.19-7.17 (m, 1H), 7.07-7.05 (m, 1H), 6.89-6.87 (m, 1H), 6.26 (s, 1H), 4.75 (s, 2H), 4.23 (m, 2H), 2.38 (s, 3H), 1.25 (m, 3H).

Step II

Compound 6c was synthesized from Compound 6a and Compound 6b according to the method in Example 1 (60 mg, white solid, 60%). MS-ESI calculated value [M+H]⁺ 414, measured value 414.

Step III

Compound 6 was synthesized from Compound 6c according to the method in Example 1 (10 mg, yield: 18%). ¹H NMR (400 MHz, CD$_3$OD) δ 8.06-7.99 (m, 1H), 7.60-7.50 (m, 2H), 7.36-7.28 (m, 1H), 7.21-7.13 (m, 1H), 6.93-6.87 (m, 1H), 6.84-6.78 (m, 1H), 6.29-6.27 (m, 1H), 4.99-4.98 (m, 2H), 4.27-4.26 (m, 2H), 2.27 (s, 3H). MS-ESI calculated value [M+H]$^+$ 386, measured value 386.

Example 7

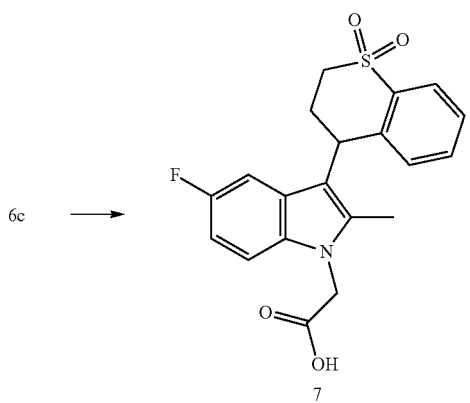 [SMILES: Cc1c(C2CCS(=O)(=O)c3ccccc32)c2cc(F)ccc2n1CC(=O)O]

Compound 7 was synthesized from Compound 6c according to the method in Example 2 (54 mg, yield: 71%). $^1$H NMR (400 MHz, CD$_3$OD) δ 7.94-7.92 (m, 1H), 7.49-7.41 (m, 1H), 7.40-7.33 (m, 1H), 7.28-7.18 (m, 1H), 7.06-7.05 (m, 1H), 6.86-6.75 (m, 1H), 6.49 (br.s., 1H), 4.96 (s, 2H), 4.64 (br.s., 1H), 3.71-3.60 (m, 1H), 3.54-3.44 (m, 1H), 2.90 (br.s., 1H), 2.59-2.33 (m, 4H). MS-ESI calculated value [M+H]$^+$ 388, measured value 388.

Example 8

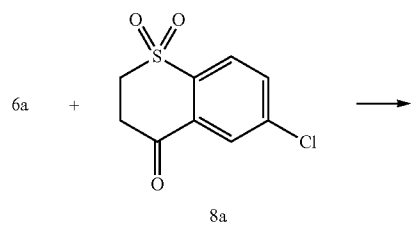

Compound 8 was synthesized from Compound 6a and Compound 8a according to the method in Example 1 (19 mg, yield: 33%). $^1$H NMR (400 MHz, CD$_3$OD) δ 8.02-8.00 (m, 1H), 7.59-7.56 (m, 1H), 7.33-7.32 (m, 1H), 7.12 (s, 1H), 6.93-6.82 (m, 1H), 6.83-6.80 (m, 1H), 6.36-6.33 (m, 1H), 5.01-5.00 (m, 2H), 4.31-4.29 (m, 2H), 2.28 (s, 3H). MS-ESI calculated value [M+H]$^+$ 422, measured value 422.

Example 9

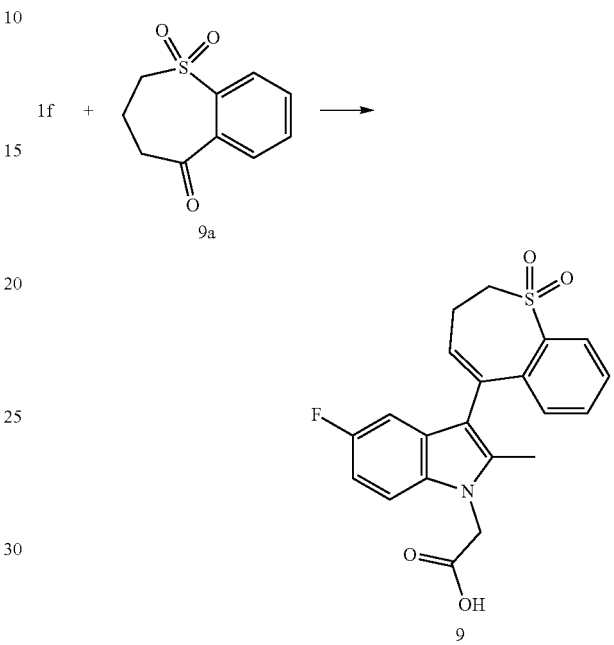

Compound 9 was synthesized from Compound 1f and Compound 9a according to the method in Example 1, except for replacing trifluoroacetic acid with p-toluenesulfonic acid (4 mg, yield: 10%). $^1$H NMR (400 MHz, CD$_3$OD) δ 8.18-8.08 (m, 1H), 7.63-7.47 (m, 2H), 7.29-7.19 (m, 1H), 7.14-7.12 (m, 1H), 6.94-6.88 (m, 1H), 6.86-6.82 (m, 1H), 6.33-6.31 (m, 1H), 4.94 (s, 2H), 3.95-3.92 (m, 2H), 2.70-2.57 (m, 2H), 2.19 (s, 3H). MS-ESI calculated value [M+H]$^+$ 400, measured value 400.

Example 10

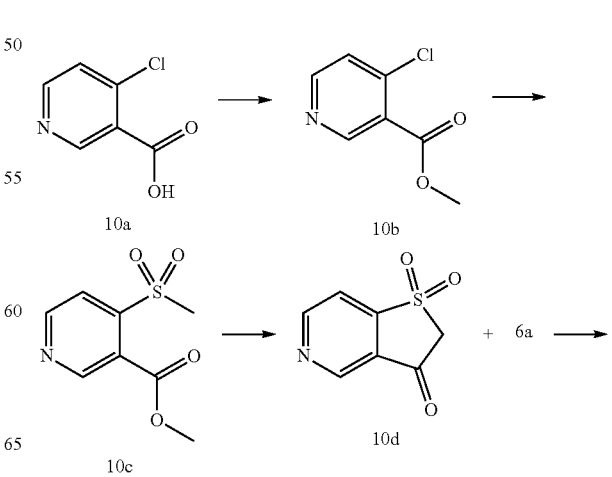

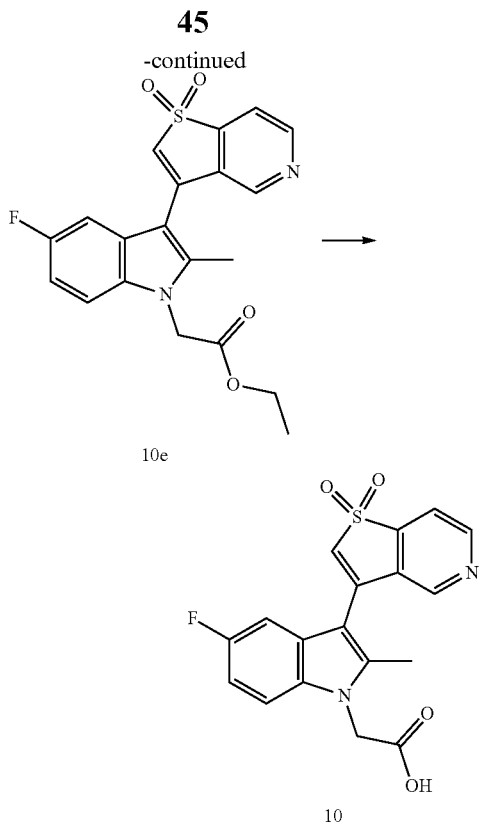

Step I

Compound 10a (13.30 g, 84.42 mmol) was dissolved in dichloromethane (75 mL) and methanol (30 mL), and trimethylsilyl diazomethane (126.64 mmol, 63.32 mL, 2 M) was slowly added dropwise at 0° C. The reaction mixture was warmed to 5-15° C., and stirred for 2 hr. The reaction mixture was directly concentrated to dryness, and then separated and purified by flash silica gel column chromatography (petroleum ether/ethyl acetate 100-60%), to give Compound 10b (9.80 g, brown oil, yield: 68%). $^1$H NMR (400 MHz, CDCl$_3$) δ 9.03 (s, 1H), 8.58 (d, J=5.6 Hz, 1H), 7.42 (d, J=5.6 Hz, 1H), 3.96 (s, 3H). MS-ESI calculated value [M+H]$^+$ 172, measured value 172.

Step II

Compound 10b (9.80 g, 57.12 mmol) and sodium methanesulfinate (14.58 g, 142.80 mmol) were dissolved in dimethyl sulfoxide (100 mL). The reaction mixture was heated to 100° C. and stirred for 3 hr. The reaction mixture was cooled to room temperature, and poured into water (600 mL). The resulting mixture was extracted with ethyl acetate (400 mL×2). The organic phases were combined, washed with saturated brine (400 mL), dried over anhydrous sodium sulfate, filtered, and concentrated under reduced pressure, to give Compound 10c (8.10 g, pink solid, yield: 66%). $^1$H NMR (400 MHz, CDCl$_3$) δ 9.05 (s, 1H), 9.01 (d, J=5.2 Hz, 1H), 8.00 (d, J=5.2 Hz, 1H), 4.02 (s, 3H), 3.41 (s, 3H). MS-ESI calculated value [M+H]$^+$ 216, measured value 216.

Step III

Compound 10c (8.00 g, 37.17 mmol) was dissolved in tetrahydrofuran (200 mL), and lithium bis(trimethylsilyl) amide (44.60 mmol, 1M, 44.60 mL) was slowly added dropwise at −78° C. The reaction mixture was warmed to room temperature and stirred for 3 hr, and then water (200 mL) was added to quench the reaction. The resulting mixture was adjusted with 1 N hydrochloric acid to pH 6-7, and extracted with ethyl acetate (250 mL×2). The organic phase was washed with saturated brine (250 mL), dried over anhydrous sodium sulfate, filtered, and concentrated under reduced pressure, to give Compound 10d (4.36 g, yellow solid, yield: 64%). $^1$H NMR (400 MHz, CDCl$_3$) δ 9.36 (s, 1H), 9.19 (d, J=5.2 Hz, 1H), 7.92-7.90 (m, 1H), 4.12 (s, 2H). MS-ESI calculated value [M+H]$^+$ 184, measured value 184.

Step IV

Compound 10d (78 mg, 0.43 mmol) and Compound 6a (100 mg, 0.43 mmol) were dissolved in 1,2-dichloroethane (10 mL), and triethylsilane (247 mg, 2.13 mmol) and p-toluenesulfonic acid monohydrate (121 mg, 0.64 mmol) were added. The resulting reaction mixture was heated to 60° C., and stirred for 16 hr. The reaction mixture was washed with a saturated aqueous solution of sodium bicarbonate (20 mL), and extracted with dichloromethane (10 mL×2). The organic phases were combined, dried over anhydrous sodium sulfate, filtered, concentrated under reduced pressure to dryness, and separated and purified by thin-layer silica gel chromatoplates (petroleum ether/ethyl acetate=2/1), to give Compound 10e (98 mg, yellow solid, yield: 20%). MS-ESI calculated value [M+H]$^+$ 401, measured value 401.

Step V

Compound 10 was synthesized from Compound 10e according to the method in Example 1 (10 mg, yield: 19%). $^1$H NMR (400 MHz, CD$_3$OD) δ 8.91 (br. s., 1H), 8.67 (br. s., 1H), 7.89 (d, J=2.8 Hz, 1H), 7.51-7.40 (m, 1H), 7.11-6.99 (m, 3H), 5.06 (br. s., 1H), 3.83 (s, 1H), 2.55-2.47 (m, 3H). MS-ESI calculated value [M+H]$^+$ 373, measured value 373.

Example 11

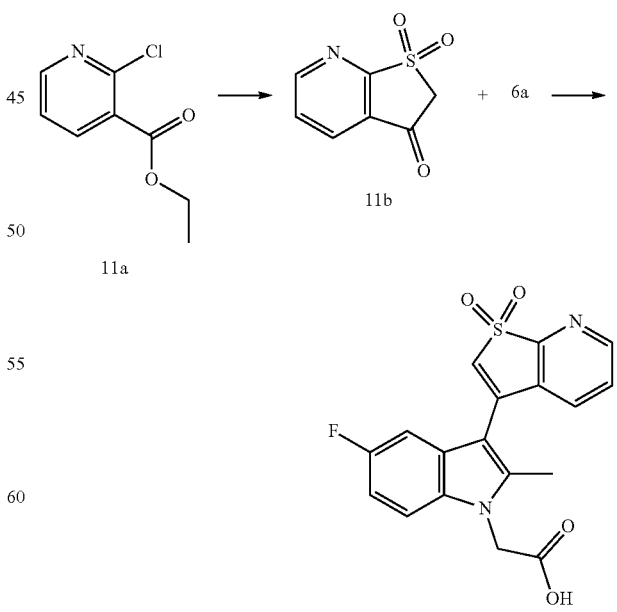

Compound 11b was synthesized from Compound 11a through a three-step reaction according to the method in Example 10, and then Compound 11 was synthesized from Compound 11b and Compound 6a according to the method in Example 1 (17 mg, yield: 29%). $^1$H NMR (400 MHz, CD$_3$OD) δ 8.69 (d, J=4.8 Hz, 1H), 7.86 (d, J=7.6 Hz, 1H), 7.66-7.58 (m, 1H), 7.46-7.38 (m, 1H), 7.08 (s, 1H), 7.07-6.97 (m, 2H), 5.08 (s, 2H), 2.47 (s, 3H). MS-ESI calculated value [M+H]$^+$ 373, measured value 373.

Example 12

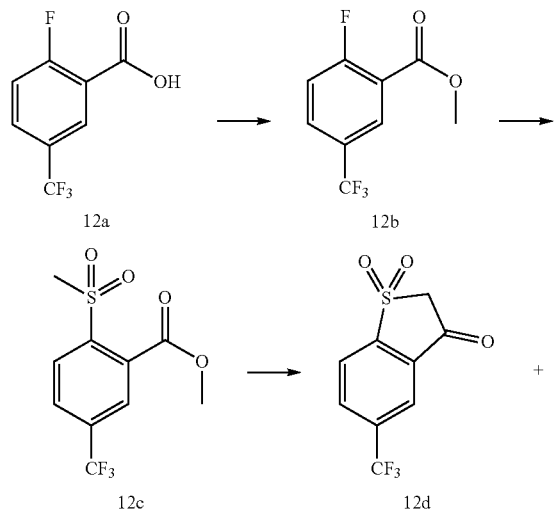

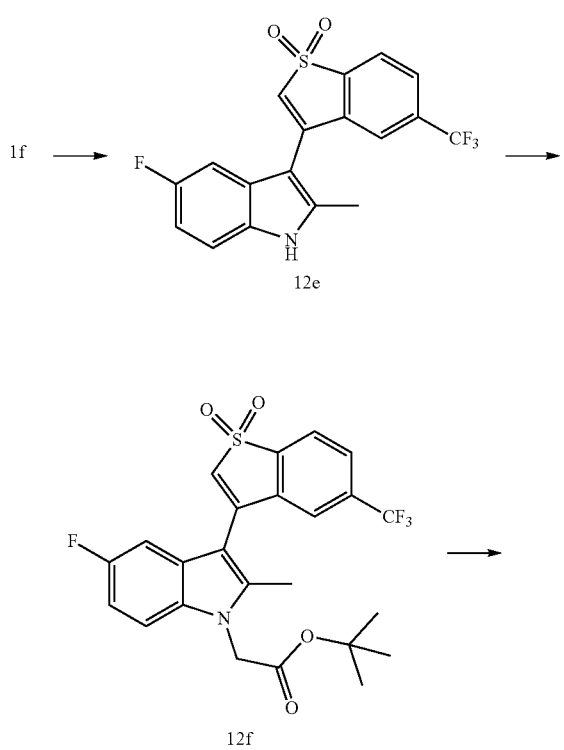

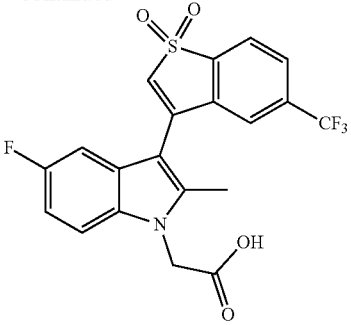

12

Step I

Compound 12a (2.00 g, 9.61 mmol) was added to a solution of sulfoxide chloride (2.29 g, 19.20 mmol) in methanol (20 mL) at 0° C. The resulting mixture was warmed to 30° C., and stirred for 16 hr. After removing the solvent under reduced pressure, the reaction mixture was diluted with ethyl acetate (50 mL), washed with a saturated aqueous solution of sodium bicarbonate (20 mL) and saturated brine (50 mL×3), and dried over anhydrous sodium sulfate. The drying agent was removed by filtration, and the solvent was removed from the filtrate under reduced pressure, to give Compound 12b as a colorless liquid (1.20 g, colorless liquid, yield: 56%). $^1$H NMR (400 MHz, CDCl$_3$) δ 8.25-8.24 (m, 1H), 7.80-7.78 (m, 1H), 7.30-7.25 (m, 1H), 3.97 (s, 3H).

Step II

Sodium methanesulfinate (827 mg, 8.10 mmol) was added to a solution of Compound 12b in N,N-dimethylformamide (5 mL), warmed to 90° C., and stirred for 2 hr. The reaction mixture was poured into water (30 mL), stirred for 10 min, and filtered, to give Compound 12c (910 mg, white solid, yield: 60%). $^1$H NMR (400 MHz, CDCl$_3$) δ 8.30-8.28 (m, 1H), 7.98 (s, 1H), 7.95-7.93 (m, 1H), 4.02 (s, 3H), 3.39 (s, 3H).

Step III

Sodium hydride (135 mg, 3.39 mmol, 60%) was added to a solution of Compound 12c (910 mg, 3.22 mmol) in tetrahydrofuran (20 mL) at 0° C. The resulting mixture was warmed to 20° C., and stirred for 1 hr. A saturated aqueous solution of ammonium chloride (5 mL) was added to quench the reaction. Then, the resulting mixture was extracted with ethyl acetate (5 mL×3), and dried over anhydrous sodium sulfate. The drying agent was removed by filtration, and the solvent was removed from the filtrate under reduced pressure. The residue was added to a mixture of ethyl acetate (0.5 mL) and petroleum ether (20 mL), stirred for 10 min, and filtered, to give Compound 12d (650 mg, yellow solid, yield: 81%). $^1$H NMR (400 MHz, CDCl$_3$) δ 8.30 (s, 1H), 8.22-8.15 (m, 2H), 4.19 (s, 2H).

Step IV

Compound 12e was synthesized from Compound 12d and Compound 1f according to the method in Example 1 (50 mg, yellow solid, yield: 52%). $^1$H NMR (400 MHz, CDCl$_3$) δ

7.94-7.92 (m, 1H), 7.86-7.84 (m, 1H), 7.63 (s, 1H), 7.33-7.30 (m, 1H), 7.05-7.03 (m, 1H), 6.99-6.98 (m, 1H), 6.66 (s, 1H), 2.51 (s, 3H).

Step V

Cesium carbonate (64 mg, 0.20 mmol) was added to a solution of Compound 12e (50 mg, 0.13 mmol) and t-butyl bromoacetate (31 mg, 0.16 mmol) in N,N-dimethylformamide (1 mL), and the resulting mixture was stirred for 16 hr at 30° C. The reaction mixture was poured into water (20 mL), and extracted with ethyl acetate (5 mL×2). The organic phase was dried over anhydrous sodium sulfate. The drying agent was removed by filtration, and the solvent was removed from the filtrate under reduced pressure. The residue was purified by thick-layer chromatoplates (petroleum ether/ethyl acetate=4/1), to give Compound 12f (40 mg, yellow solid, yield: 40%). $^1$H NMR (400 MHz, CDCl$_3$) δ 7.95-7.93 (m, 1H), 7.86-7.84 (m, 1H), 7.59 (s, 1H), 7.22-7.21 (m, 1H), 7.09-7.03 (m, 2H), 6.69 (s, 1H), 4.78 (s, 2H), 2.44 (s, 3H), 1.47 (s, 9H).

Step VI

Trifluoroacetic acid (0.2 mL) was added to a solution of Compound 12f (50 mg, 0.10 mmol) in 2 mL of dichloromethane at 0° C. The resulting mixture was warmed to 30° C., and stirred for 4 hr. The solvent was removed from the reaction mixture under reduced pressure. The residue was purified by preparative high performance liquid chromatography column, to give Compound 12 (23 mg, yield: 52%). $^1$H NMR (400 MHz, CDCl$_3$) δ 7.98-7.96 (m, 1H), 7.89-7.87 (m, 1H), 7.59 (s, 1H), 7.27-7.24 (m, 1H), 7.12-7.06 (m, 2H), 6.73 (s, 1H), 4.98 (s, 2H), 2.48 (s, 3H). MS-ESI calculated value [M+H]$^+$ 440, measured value 440.

Example 13

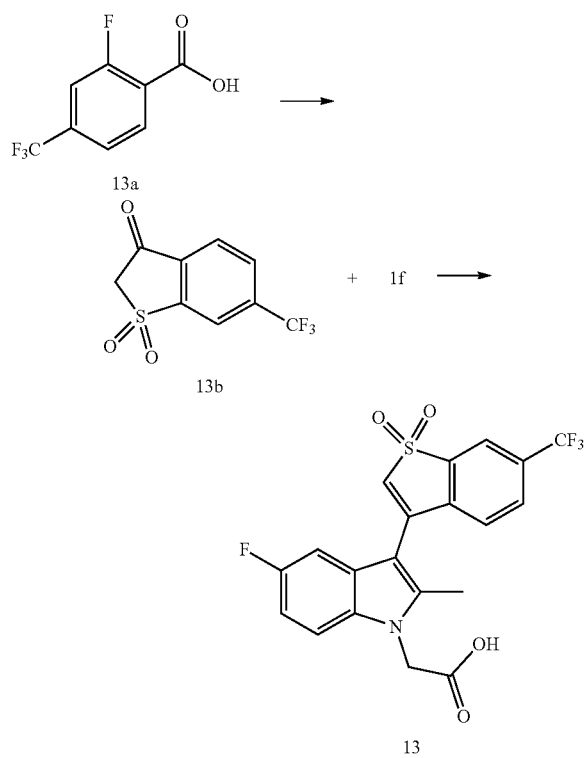

Compound 13 was obtained from Compound 13a through a multi-step reaction according to the method in Example 12 (20 mg, yield: 42%). $^1$H NMR (400 MHz, CDCl$_3$) δ 8.09 (s, 1H), 7.83-7.81 (m, 1H), 7.52-7.50 (m, 1H), 7.25-7.23 (m, 1H), 7.09-7.06 (m, 2H), 6.73 (s, 1H), 4.97 (s, 2H), 2.48 (s, 3H). MS-ESI calculated value [M+H]$^+$ 440, measured value 440.

Example 14

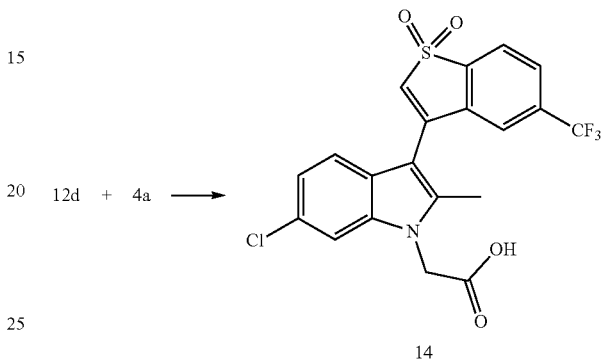

Compound 14 was synthesized from Compound 12d and Compound 4a according to the method in Example 12 (10 mg, yield: 12%). $^1$H NMR (400 MHz, CDCl$_3$) δ 7.95-7.93 (m, 1H), 7.86-7.84 (m, 1H), 7.57 (s, 1H), 7.32-7.30 (m, 2H), 7.17-7.15 (m, 1H), 6.70 (s, 1H), 4.89 (s, 2H), 2.46 (s, 3H). MS-ESI calculated value [M+H]$^+$ 456, measured value 456.

Example 15

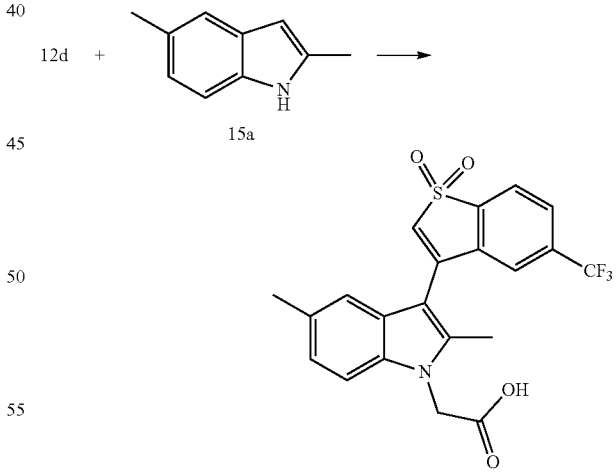

Compound 15 was synthesized from Compound 12d and Compound 15a according to the method in Example 12 (20 mg, yield: 25%). $^1$H NMR (400 MHz, CDCl$_3$) δ 7.95-7.93 (m, 1H), 7.85-7.83 (m, 1H), 7.64 (s, 1H), 7.22-7.18 (m, 2H), 7.13-7.11 (m, 1H), 6.69 (s, 1H), 4.94 (s, 2H), 2.45 (s, 3H), 2.40 (s, 3H). MS-ESI calculated value [M+H]$^{3O}$ 436, measured value 436.

Example 16

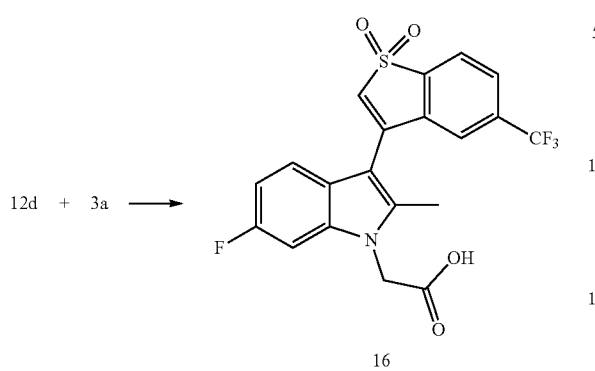

16

Compound 16 was synthesized from Compound 12d and Compound 3a according to the method in Example 12 (25 mg, yield: 31%). $^1$H NMR (400 MHz, CDCl$_3$) δ 7.97-7.95 (m, 1H), 7.88-7.86 (m, 1H), 7.59 (s, 1H), 7.36-7.34 (m, 1H), 7.03-6.98 (m, 2H), 6.72 (s, 1H), 4.93 (s, 2H), 2.47 (s, 3H). MS-ESI calculated value [M+H]$^+$ 440, measured value 440.

Example 17

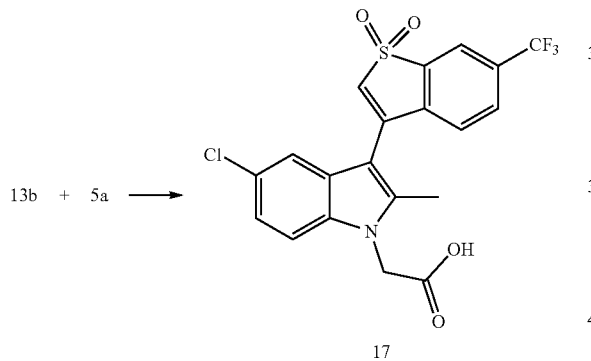

17

Compound 17 was synthesized from Compound 13b and Compound 5a according to the method in Example 12 (30 mg, yield: 81%). $^1$H NMR (400 MHz, CDCl$_3$) δ 8.07 (s, 1H), 7.82-7.80 (m, 1H), 7.48-7.46 (m, 1H), 7.38 (s, 1H), 7.24-7.22 (m, 2H), 6.73 (s, 1H), 4.95 (s, 2H), 2.46 (s, 3H). MS-ESI calculated value [M+H]$^+$ 456, measured value 456.

Example 18

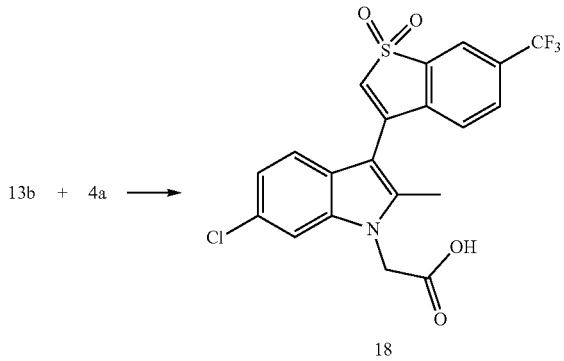 [SMILES: Cc1c(C2=CS(=O)(=O)c3cc(C(F)(F)F)ccc32)c2ccc(Cl)cc2n1CC(=O)O]

18

Compound 18 was synthesized from Compound 13b and Compound 4a according to the method in Example 12 (20 mg, yield: 45%). $^1$H NMR (400 MHz, CDCl$_3$) δ 8.06 (s, 1H), 7.79-7.77 (m, 1H), 7.46-7.45 (m, 1H), 7.32-7.30 (m, 2H), 7.16-7.14 (m, 1H), 6.72 (s, 1H), 4.92 (s, 2H), 2.45 (s, 3H). MS-ESI calculated value [M+H]$^+$ 456, measured value 456.

Example 19

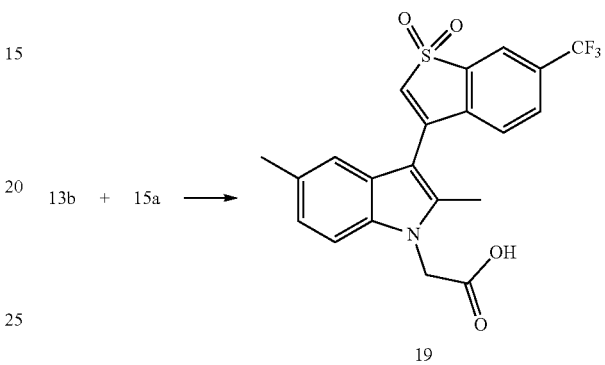

19

Compound 19 was synthesized from Compound 13b and Compound 15a according to the method in Example 12 (9 mg, yield: 33%). $^1$H NMR (400 MHz, CDCl$_3$) δ 8.06 (s, 1H), 7.78-7.76 (m, 1H), 7.53-7.51 (m, 1H), 7.20-7.18 (m, 2H), 7.13-7.11 (m, 1H), 6.70 (s, 1H), 4.93 (s, 2H), 2.44 (s, 3H), 2.41 (s, 3H). MS-ESI calculated value [M+H]$^+$ 436, measured value 436.

Example 20

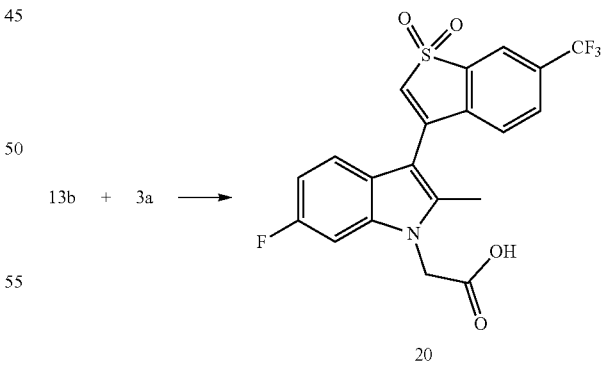

20

Compound 20 was synthesized from Compound 13b and Compound 3a according to the method in Example 12 (7 mg, yield: 26%). $^1$H NMR (400 MHz, CDCl$_3$) δ 8.06 (s, 1H), 7.79-7.77 (m, 1H), 7.49-7.47 (m, 1H), 7.34-7.33 (m, 1H), 7.02-6.92 (m, 2H), 6.72 (s, 1H), 4.91 (s, 2H), 2.46 (s, 3H). MS-ESI calculated value [M+H]$^+$ 440, measured value 440.

Example 21

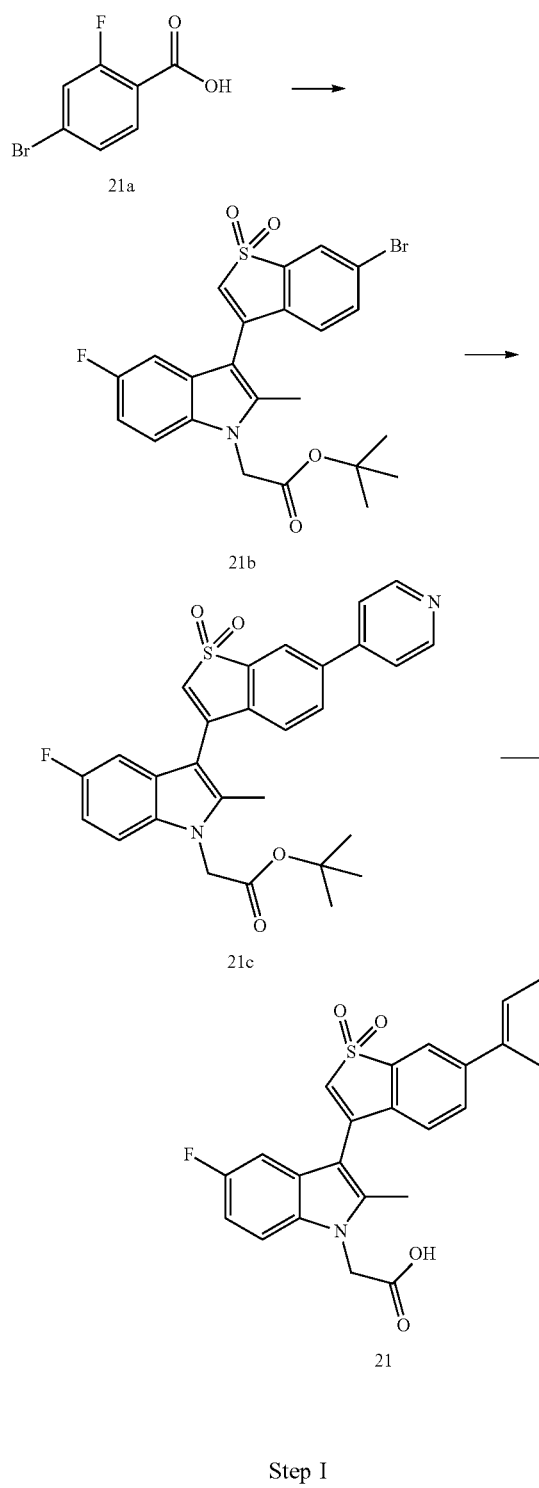

Step I

Compound 21b was synthesized from Compound 21a through a multi-step reaction according to the method in Example 12 (1.00 g, yellowish solid, yield: 83%). $^1$H NMR (400 MHz, CDCl$_3$) δ 7.93 (s, 1H), 7.66-7.64 (m, 1H), 7.24-7.18 (m, 2H), 7.07-7.01 (m, 2H), 6.55 (s, 1H), 4.77 (s, 2H), 2.44 (s, 3H), 1.47 (s, 9H).

Step II

Under the protection of nitrogen, 1,1'-bis(di-t-butylphosphino)ferrocene palladium dichloride (9 mg, 0.01 mmol) was added to a mixed solution of Compound 21a (70 mg, 0.14 mmol), 4-pyridinylboric acid (19 mg, 0.15 mmol) and potassium phosphate (73 mg, 0.35 mmol) in tetrahydrofuran (1 mL) and water (0.2 mL). The resulting mixture was warmed to 60° C., and stirred for 1.5 hr. The mixture was diluted with ethyl acetate (20 mL), washed with saturated brine (10 mL×3), and dried over anhydrous sodium sulfate. The drying agent was removed by filtration, and the solvent was removed from the filtrate under reduced pressure. The residue was purified by thick-layer chromatoplates (petroleum ether/ethyl acetate=4/1), to give Compound 21b (65 mg, yellow solid, yield: 92%). $^1$H NMR (400 MHz, CDCl$_3$) δ 8.08 (s, 1H), 7.80-7.70 (m, 3H), 7.50-7.48 (m, 1H), 7.21-7.20 (m, 1H), 7.13-7.10 (m, 1H), 7.02-7.00 (m, 1H), 6.63 (s, 1H), 4.79 (s, 2H), 2.48 (s, 3H), 1.48 (s, 9H).

Step III

Compound 21 was synthesized from Compound 21b according to the method in Example 12 (25 mg, yield: 47%). $^1$H NMR (400 MHz, CD$_3$OD) δ 8.86-8.85 (m, 2H), 8.46 (s, 1H), 8.30-8.28 (m, 2H), 8.21-8.19 (m, 1H), 7.68-7.66 (m, 1H), 7.46-7.44 (m, 1H), 7.14-7.04 (m, 3H), 5.13 (s, 2H), 2.51 (s, 3H). MS-ESI calculated value [M+H]$^+$ 449, measured value 449.

Example 22

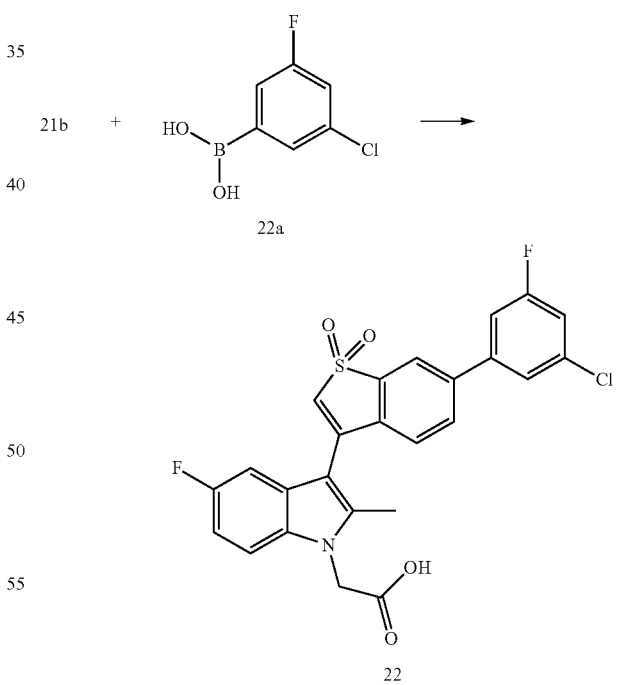

Compound 22 was synthesized from Compound 21b and Compound 22a according to the method in Example 21 (20 mg, yield: 44%). $^1$H NMR (400 MHz, CDCl$_3$) δ 7.98 (s, 1H), 7.69-7.67 (m, 1H), 7.44-7.41 (m, 2H), 7.23-7.21 (m, 2H), 7.17-7.13 (m, 2H), 7.05-7.03 (m, 1H), 6.62 (s, 1H), 4.95 (s, 2H), 2.47 (s, 3H). MS-ESI calculated value [M+H]$^+$ 500, measured value 500.

Example 23

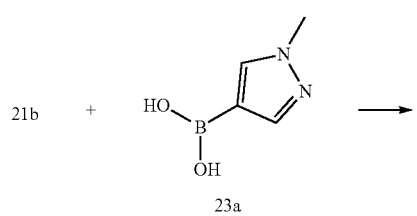

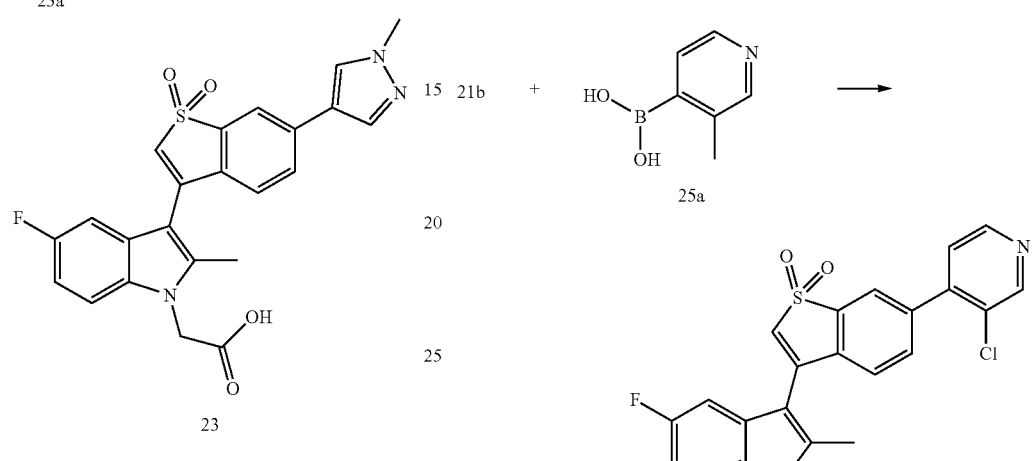

Compound 23 was synthesized from Compound 21b and Compound 23a according to the method in Example 21 (15 mg, yield: 48%). ¹H NMR (400 MHz, CD$_3$OD) δ 8.19 (s, 1H), 8.07 (s, 1H), 8.00 (s, 1H), 7.84-7.82 (m, 1H), 7.44-7.42 (m, 2H), 7.11-7.08 (m, 1H), 7.04-7.01 (m, 1H), 6.90 (s, 1H), 5.10 (s, 2H), 3.97 (s, 3H), 2.49 (s, 3H). MS-ESI calculated value [M+H]$^+$ 452, measured value 452.

Example 24

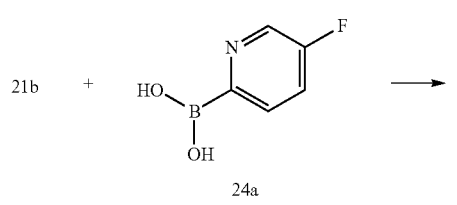

Compound 24 was synthesized from Compound 21b and Compound 24a according to the method in Example 21 (7 mg, yield: 52%). ¹H NMR (400 MHz, CD$_3$OD) δ 8.62-8.61 (m, 1H), 8.52 (s, 1H), 8.29-8.26 (m, 1H), 8.09-8.08 (m, 1H), 7.74-7.72 (m, 1H), 7.55-7.53 (m, 1H), 7.43-7.42 (m, 1H), 7.11-7.09 (m, 1H), 7.02-7.01 (m, 2H), 5.10 (s, 2H), 2.50 (s, 3H). MS-ESI calculated value [M+H]$^+$ 467, measured value 467.

Example 25

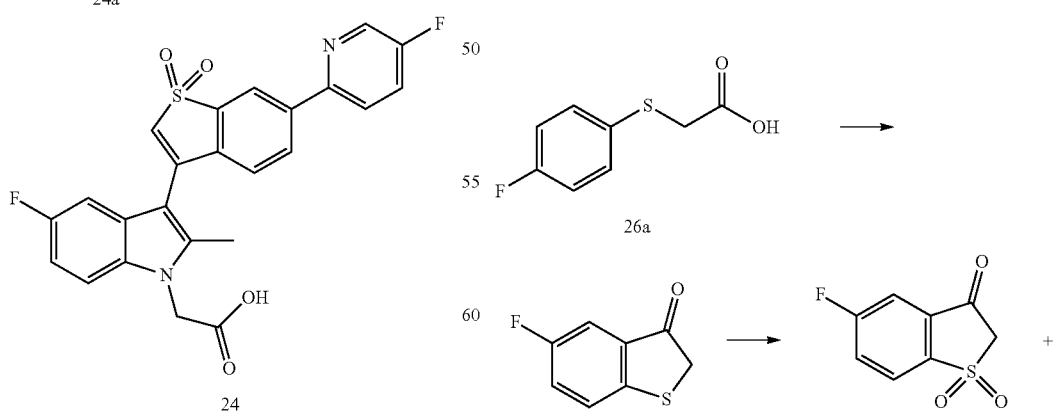

Compound 25 was synthesized from Compound 21b and Compound 25a according to the method in Example 21 (30 mg, yield: 56%). ¹H NMR (400 MHz, CD$_3$OD) δ 8.76 (s, 1H), 8.62-8.60 (m, 1H), 8.05 (s, 1H), 7.82-7.80 (m, 1H), 7.60-7.59 (m, 2H), 7.46-7.44 (m, 1H), 7.13-7.11 (m, 1H), 7.10 (s, 1H), 7.08-7.03 (m, 1H), 5.12 (s, 2H), 2.51 (s, 3H). MS-ESI calculated value [M+H]$^+$ 483, measured value 483.

Example 26

1f → 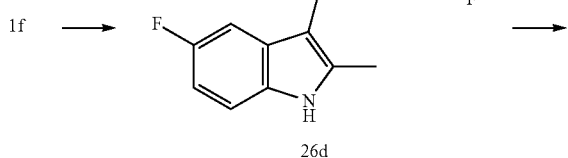 →

26d

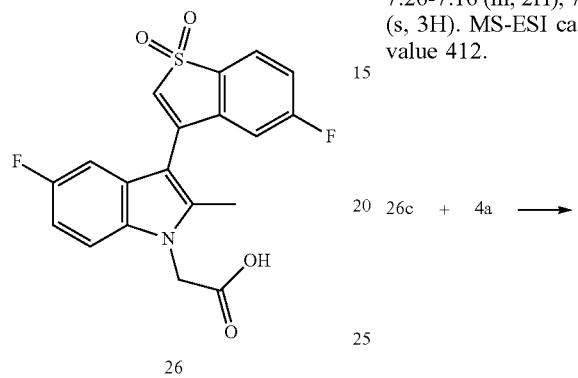

26

Step I

Oxalyl chloride (20.72 g, 163.26 mmol, 14.29 mL) and 1 mL of N,N-dimethylformamide were added dropwise to a solution of Compound 26a (15.20 g, 81.63 mmol) in 150 mL of dichloromethane at 0° C. The reaction mixture was reacted for 1 hr at 0° C., and concentrated. 200 mL of dichloromethane and aluminium trichloride (32.65 g, 244.89 mmol) were added to the concentrate, and the resulting mixture was stirred for 16 hr at room temperature. After completion of the reaction, the reaction mixture was poured into 200 mL of ice water, and extracted with dichloromethane (100 mL×3). The organic phase was washed with a saturated aqueous solution of sodium chloride, dried, filtered, and purified by silica gel column chromatography (petroleum ether/ethyl acetate 100-50%), to give the target Compound 26b (9.1 g, yellow solid, yield: 71%). $^1$H NMR (400 MHz, CDCl$_3$) δ 7.44 (dd, J=2.6, J=7.6 Hz, 1H), 7.37 (d, J=7.6 Hz, 1H), 7.34-7.28 (m, 1H), 3.87 (s, 2H).

Step II

At 0° C., m-chloroperoxybenzoic acid (32.71 g, 151.62 mmol, 80%) was added to a solution of Compound 26b (8.50 g, 50.54 mmol) in 150 mL of dichloromethane. The reaction mixture was stirred for 2 hr at room temperature. After completion of the reaction, 600 mL of a saturated solution of sodium bicarbonate was added to the reaction mixture, and the resulting mixture was extracted with ethyl acetate (100 mL×3). The organic phase was washed with a saturated aqueous solution of sodium chloride, dried over anhydrous sodium sulfate, filtered, and purified by silica gel column chromatography (petroleum ether/ethyl acetate 100-50%), to give the target Compound 26c (7.90 g, yellowish solid, yield: 78%). $^1$H NMR (400 MHz, CDCl$_3$) δ 8.12-8.10 (m, 1H), 8.04-8.02 (m, 1H), 7.62 (m, 1H), 4.16 (s, 2H).

Step III

Compound 26d was synthesized from Compound 26c and Compound 1f according to the method in Example 1 (85 mg, yellowish oil liquid, yield: 42%). $^1$H NMR (400 MHz, CDCl$_3$) δ 7.75-7.68 (m, 1H), 7.27-7.24 (m, 1H), 7.16 (m, 1H), 7.03-6.95 (m, 2H), 6.89-6.81 (m, 2H), 6.55 (s, 1H), 2.43 (s, 3H).

Step IV

Compound 26 was synthesized from Compound 26d through a multi-step reaction according to the method in Example 1 (18 mg, yield: 19%). $^1$H NMR (400 MHz, CD$_3$OD) δ 7.91-7.85 (m, 1H), 7.37 (d, J=9.6 Hz, 2H), 7.26-7.16 (m, 2H), 7.02 (s, 1H), 6.92 (d, J=9.6 Hz, 1H), 2.46 (s, 3H). MS-ESI calculated value [M+Na]$^+$ 412, measured value 412.

Example 27

26c + 4a →

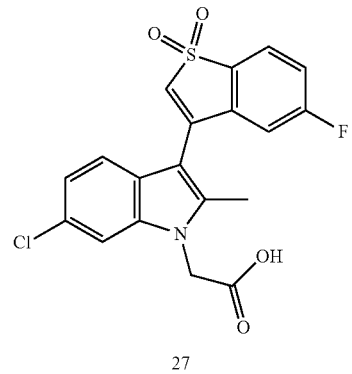

27

Compound 27 was synthesized from Compound 26c and Compound 4a according to the method in Example 1 (40 mg, yield: 25%). $^1$H NMR (400 MHz, CD$_3$OD) δ 7.93-7.86 (m, 1H), 7.50 (s, 1H), 7.43-7.33 (m, 2H), 7.19-7.11 (m, 2H), 7.05 (s, 1H), 5.02-4.97 (m, 2H), 2.47 (s, 3H). MS-ESI calculated value [M+Na]$^+$ 428, measured value 428.

Example 28

26c + 15a →

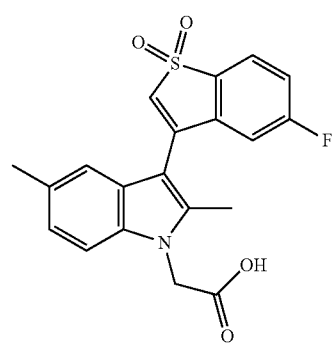

28

Compound 28 was synthesized from Compound 26c and Compound 15a according to the method in Example 1 (35 mg, yield: 20%). $^1$H NMR (400 MHz, CD$_3$OD) δ 7.89-7.83

(m, 1H), 7.36 (s, 1H), 7.31-7.26 (m, 1H), 7.19-7.12 (m, 2H), 7.10-7.05 (m, 1H), 6.97 (s, 1H), 5.02 (s, 2H), 2.43 (s, 3H), 2.39 (s, 3H). MS-ESI calculated value [M+Na]⁺ 408, measured value 408.

Example 29

26c + 5a ⟶

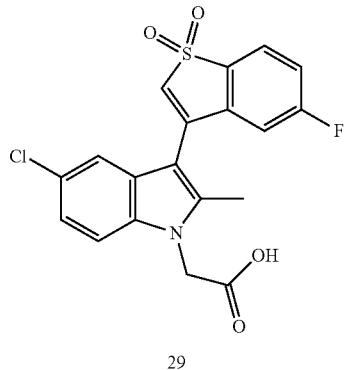

29

Compound 29 was synthesized from Compound 26c and Compound 5a according to the method in Example 1 (15 mg, yield: 12%). ¹H NMR (400 MHz, CD₃OD) δ 7.94-7.87 (m, 1H), 7.46-7.40 (m, 2H), 7.37-7.36 (m, 1H), 7.25-7.22 (m, 1H), 7.18-7.12 (m, 1H), 7.09 (s, 1H), 5.10-5.04 (m, 2H), 2.47 (s, 3H). MS-ESI calculated value [M+Na]⁺ 428, measured value 428.

Example 30

26c + 3a ⟶

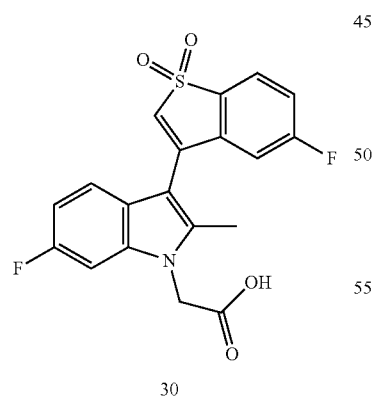

30

Compound 30 was synthesized from Compound 26c and Compound 3a according to the method in Example 1 (23 mg, yield: 18%). ¹H NMR (400 MHz, CD₃OD) δ 7.92-7.86 (m, 1H), 7.48-7.35 (m, 2H), 7.24-7.20 (m, 1H), 7.08-7.03 (m, 2H), 7.03-6.96 (m, 1H), 4.99-4.94 (m, 2H), 2.47 (s, 3H). MS-ESI calculated value [M+H]⁺ 390, measured value 390.

Example 31

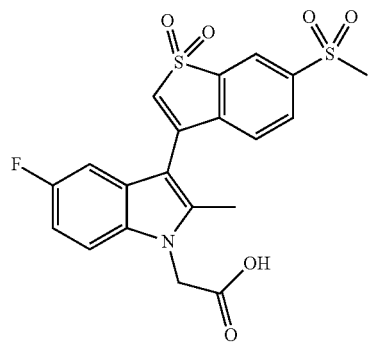

31

Compound 31 was synthesized according to the synthesis method in Example 21 (20 mg, yield: 28%). ¹H NMR (400 MHz, CDCl₃) δ 8.36 (s, 1H), 8.13-8.11 (m, 1H), 7.57-7.55 (m, 1H), 7.20-7.28 (m, 1H), 7.07-7.03 (m, 2H), 6.77 (s, 1H), 4.96 (s, 2H), 3.15 (s, 3H), 2.47 (s, 3H). MS-ESI calculated value [M+H]⁺ 450, measured value 450.

Example 32

1e +

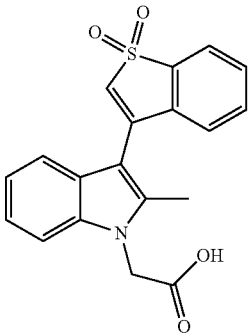

32a

⟶

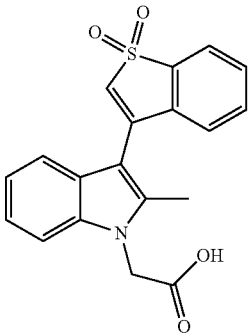

32

Compound 32 was synthesized from Compound 1e and Compound 32a according to the method in Example 1 (35 mg, yield: 30%). ¹H NMR (400 MHz, CDCl₃) δ 7.83-7.81 (m, 2H), 7.66-7.60 (m, 2H), 7.475-7.458 (m, 1H), 7.414-7.381 (m, 2H), 7.24-7.21 (m, 1H), 7.13-7.09 (m, 1H), 6.89 (s, 1H), 5.05 (s, 2H), 2.47 (s, 3H). MS-ESI calculated value [M+H]⁺ 354, measured value 354.

Example 33

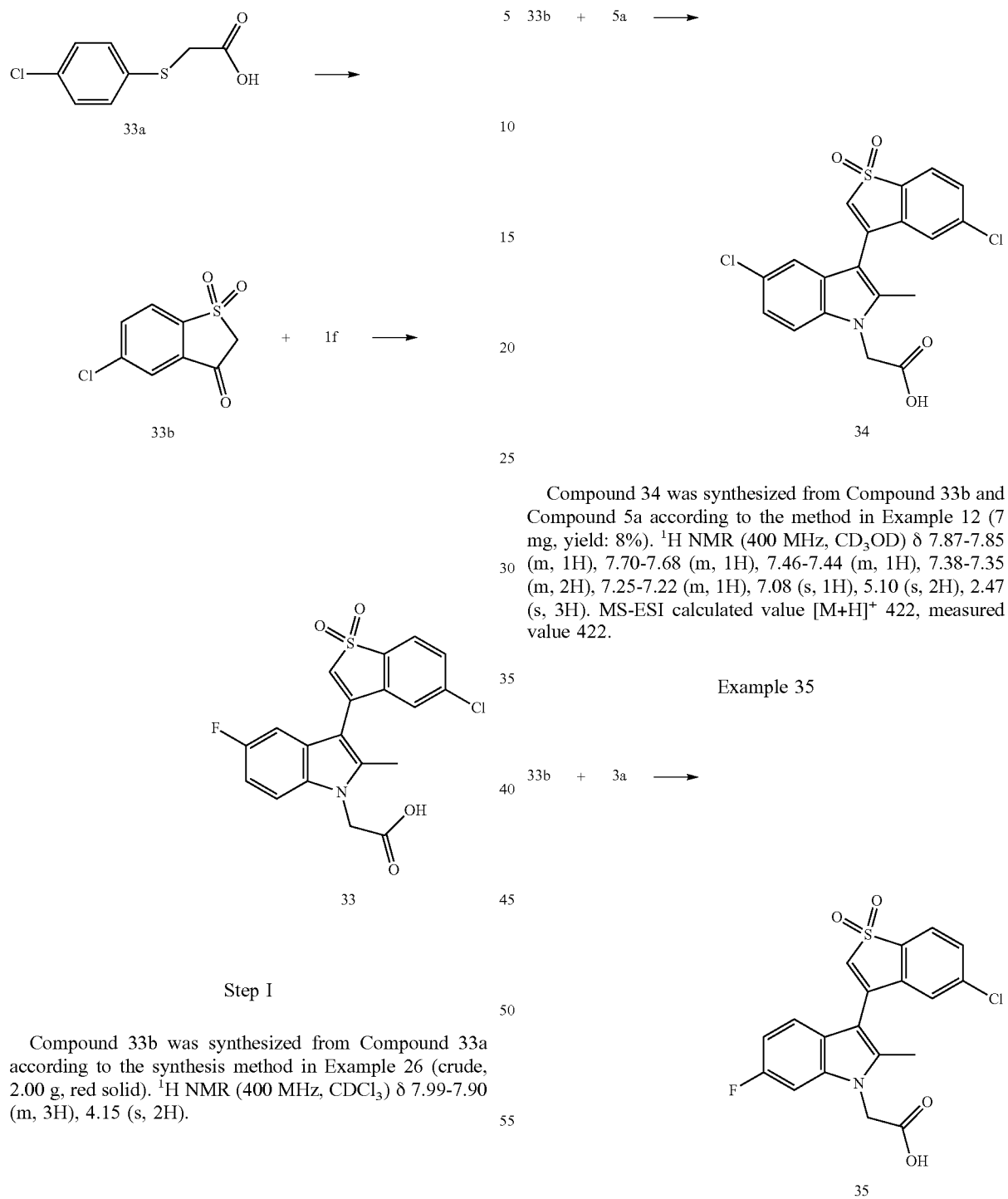

Step I

Compound 33b was synthesized from Compound 33a according to the synthesis method in Example 26 (crude, 2.00 g, red solid). $^1$H NMR (400 MHz, CDCl$_3$) δ 7.99-7.90 (m, 3H), 4.15 (s, 2H).

Step II

Compound 33 was synthesized from Compound 33b and Compound 1f according to the method in Example 12 (14 mg, yield: 22%). $^1$H NMR (400 MHz, CDCl$_3$) δ 7.76-7.74 (m, 1H), 7.55-7.53 (m, 1H), 7.28 (s, 1H), 7.23-7.20 (m, 1H), 7.12-7.00 (m, 2H), 6.63 (s, 1H), 4.93 (s, 2H), 2.44 (s, 3H). MS-ESI calculated value [M+H]$^+$ 406, measured value 406.

Example 34

Compound 34 was synthesized from Compound 33b and Compound 5a according to the method in Example 12 (7 mg, yield: 8%). $^1$H NMR (400 MHz, CD$_3$OD) δ 7.87-7.85 (m, 1H), 7.70-7.68 (m, 1H), 7.46-7.44 (m, 1H), 7.38-7.35 (m, 2H), 7.25-7.22 (m, 1H), 7.08 (s, 1H), 5.10 (s, 2H), 2.47 (s, 3H). MS-ESI calculated value [M+H]$^+$ 422, measured value 422.

Example 35

Compound 35 was synthesized from Compound 33b and Compound 3a according to the method in Example 12 (47 mg, yield: 45%). $^1$H NMR (400 MHz, CD$_3$OD) δ 7.84-7.82 (m, 1H), 7.67-7.65 (m, 1H), 7.39-7.32 (m, 2H), 7.25-7.21 (m, 1H), 7.02 (s, 1H), 6.96-6.91 (m, 1H), 5.07 (s, 2H), 2.45 (s, 3H). MS-ESI calculated value [M+H]$^+$ 406, measured value 406.

Example 36

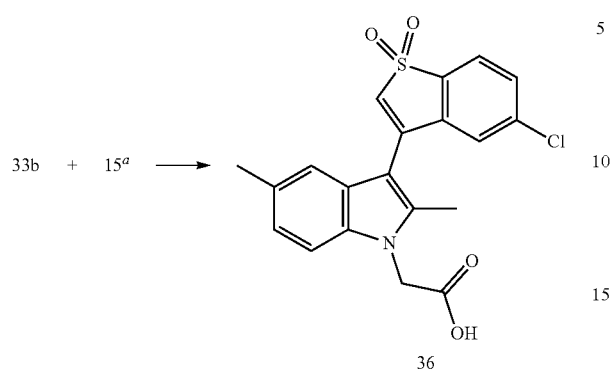

Compound 36 was synthesized from Compound 33b and Compound 15a according to the method in Example 12 (52 mg, yield: 51%). $^1$H NMR (400 MHz, CD$_3$OD) δ 7.82-7.80 (m, 1H), 7.66-7.63 (m, 1H), 7.41-7.39 (m, 1H), 7.31-7.28 (m, 1H), 7.15 (s, 1H), 7.08-7.06 (m, 1H), 6.95 (s, 1H), 5.03 (s, 2H), 2.43 (s, 3H), 2.38 (s, 3H). MS-ESI calculated value [M+H]$^+$ 402, measured value 402.

Example 37

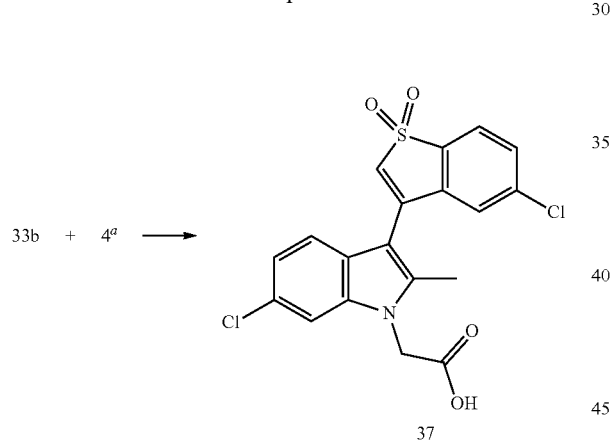

Compound 37 was synthesized from Compound 33b and Compound 4a according to the method in Example 12 (32 mg, yield: 32%). $^1$H NMR (400 MHz, CD$_3$OD) δ 7.85-7.83 (m, 1H), 7.69-7.66 (m, 1H), 7.53-7.51 (m, 1H), 7.38-7.32 (m, 2H), 7.15-7.13 (m, 1H), 7.05 (s, 1H), 5.09 (s, 2H), 2.46 (s, 3H). MS-ESI calculated value [M+H]$^+$ 422, measured value 422.

Example 38

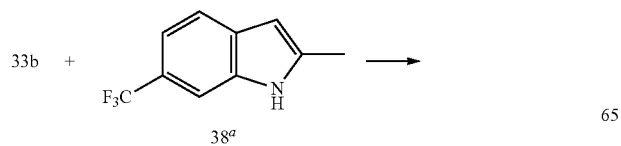

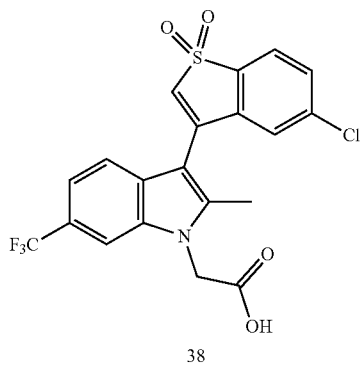

Compound 38 was synthesized from Compound 33b and Compound 38a according to the method in Example 12 (10 mg, yield: 18%). $^1$H NMR (400 MHz, CD$_3$OD) δ 7.87-7.82 (m, 2H), 7.70-7.68 (m, 1H), 7.56-7.53 (m, 1H), 7.44-7.42 (m, 1H), 7.36-7.35 (m, 1H), 7.12 (s, 1H), 5.21 (s, 2H), 2.51 (s, 3H). MS-ESI calculated value [M+H]$^+$ 456, measured value 456.

Example 39

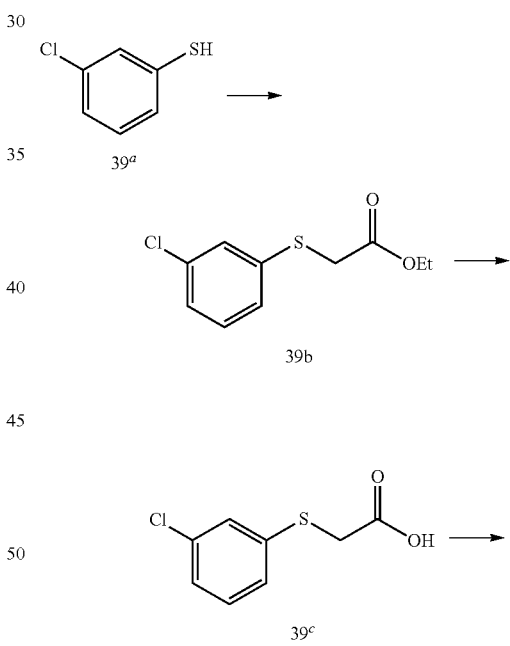

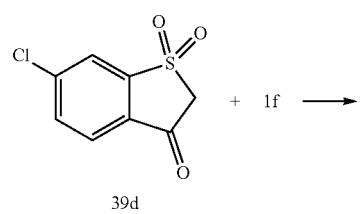

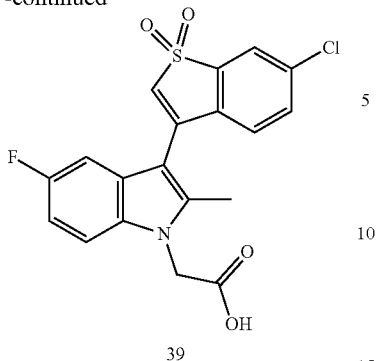

Step I

Compound 39a (10.00 g 69.15 mmol) was dissolved in acetonitrile (180 mL), and potassium carbonate (28.67 g 207.44 mmol) and ethyl bromoacetate (12.70 g 76.06 mmol) were added to the reaction mixture. The reaction mixture was further stirred for 10 hr at 50° C. The reaction mixture was directly filtered, and the filtrate was concentrated under reduced pressure, to give Compound 39b (crude, 16.00 g, yellow oil). $^1$H NMR (400 MHz, CDCl$_3$) δ 7.41 (s, 1H), 7.31-7.21 (m, 3H), 4.21 (q, J=7.2 Hz, 2H), 3.67 (s, 2H), 1.27 (t, J=7.2 Hz, 3H).

Step II

Compound 39b (16.00 g, 69.35 mmol) was dissolved in methanol (200 mL) and water (40 mL), and lithium hydroxide monohydrate (11.64 g, 277.40 mmol) was added. The reaction mixture was stirred for 10 hr at 25° C. The reaction mixture was concentrated under reduced pressure, adjusted with 2 N aqueous hydrochloric acid solution to pH=4, and filtered. The filter cake was dried to give Compound 39c (11.00 g, white solid, yield: 78%). $^1$H NMR (400 MHz, CDCl$_3$) δ 7.39 (s, 1H), 7.29-7.20 (m, 3H), 3.69 (s, 2H).

Step III

Compound 39d was synthesized from Compound 39c according to the synthesis method in Example 26 (crude, 420 mg, red solid). $^1$H NMR (400 MHz, CDCl$_3$) δ 7.98-7.96 (m, 2H), 7.80-7.78 (m, 1H), 4.13 (s, 2H).

Step IV

Compound 39 was synthesized from Compound 39d and Compound 1f according to the method in Example 12 (21 mg, yield: 22%). $^1$H NMR (400 MHz, CDCl$_3$) δ 7.91-7.90 (m, 1H), 7.67-7.64 (m, 1H), 7.44-7.40 (m, 2H), 7.06-6.99 (m, 3H), 5.09 (s, 2H), 2.46 (s, 3H). MS-ESI calculated value [M+H]$^+$ 406, measured value 406.

Example 40

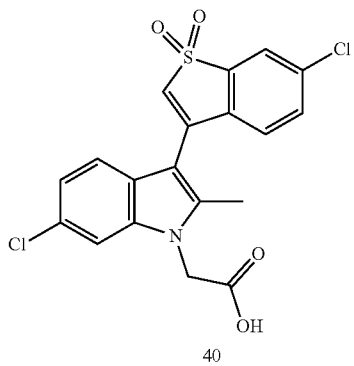

Compound 40 was synthesized from Compound 39d and Compound 4a according to the method in Example 12 (12 mg, yield: 21%). $^1$H NMR (400 MHz, CD$_3$OD) δ 7.91-7.90 (m, 1H), 7.66-7.63 (m, 1H), 7.51-7.50 (m, 1H), 7.41-7.34 (m, 2H), 7.15-7.12 (m, 1H), 7.00 (s, 1H), 5.09 (s, 2H), 2.46 (s, 3H). MS-ESI calculated value [M+H]$^+$ 422, measured value 422.

Example 41

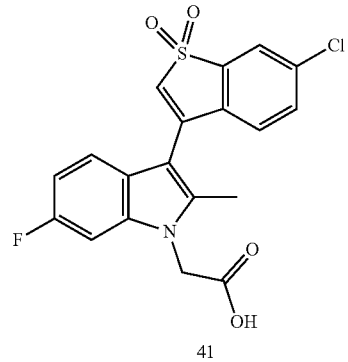

Compound 41 was synthesized from Compound 39d and Compound 3a according to the method in Example 12 (17 mg, yield: 26%). $^1$H NMR (400 MHz, CD$_3$OD) δ 7.89-7.88 (m, 1H), 7.64-7.61 (m, 1H), 7.40-7.38 (m, 1H), 7.35-7.32 (m, 1H), 7.22-7.19 (m, 1H), 6.97 (s, 1H), 6.93-6.88 (m, 1H), 5.04 (s, 2H), 2.43 (s, 3H). MS-ESI calculated value [M+H]$^+$ 406, measured value 406.

Example 42

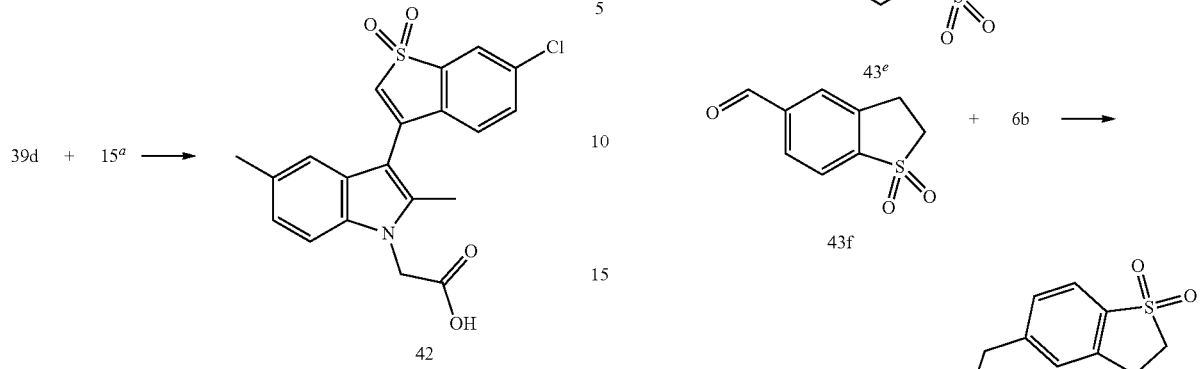

Compound 42 was synthesized from Compound 39d and Compound 15a according to the method in Example 12 (52 mg, yield: 56%). $^1$H NMR (400 MHz, CD$_3$OD) δ 7.89-7.88 (m, 1H), 7.64-7.62 (m, 1H), 7.45-7.43 (m, 1H), 7.31-7.28 (m, 1H), 7.17 (s, 1H), 7.08-7.06 (m, 1H), 6.92 (s, 1H), 5.04 (s, 2H), 2.44 (s, 3H), 2.39 (s, 3H). MS-ESI calculated value [M+H]$^+$ 402, measured value 402.

Example 43

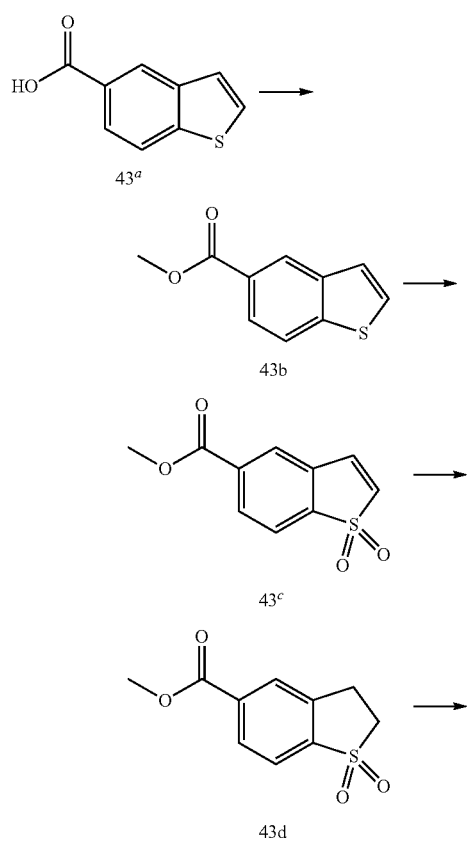

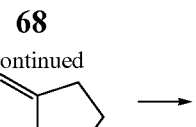

Step I

Compound 43a (1.32 g, 7.41 mmol) was dissolved in methanol (35 mL), and sulfoxide chloride (1.32 g, 11.12 mmol) was added in batch. The reaction mixture was heated to 60° C., stirred for 4 hr, and directly concentrated to dryness, to give Compound 43b (1.40 g, white solid, yield: 97%). $^1$H NMR (400 MHz, CDCl$_3$) δ 8.54 (d, J=1.2 Hz, 1H), 8.03-7.98 (m, 1H), 7.95-7.90 (m, 1H), 7.52 (d, J=5.6 Hz, 1H), 7.43 (d, J=5.6 Hz, 1H), 3.96 (s, 3H).

Step II

Compound 43b (1.40 g, 7.28 mmol) was dissolved in dichloromethane (50 mL), and m-chloroperoxybenzoic acid (4.43 g, 21.84 mmol, 80%) was added at 0° C. The reaction mixture was stirred for 16 hr at 30° C., and a saturated solution of sodium thiosulfate (20 mL) was added to quench the reaction. The resulting mixture was adjusted with a sodium carbonate solution to pH 7-8. The organic phase was washed with a saturated aqueous solution of sodium bicarbonate (50 mL), dried over anhydrous sodium sulfate, filtered, and concentrated under reduced pressure to dryness, to give Compound 43c (1.73 g, white solid, yield: 89%). $^1$H NMR (400 MHz, CDCl$_3$) δ 8.26-8.18 (m, 1H), 8.03 (s, 1H), 7.80 (d, J=7.6 Hz, 1H), 7.28 (d, J=7.2 Hz, 1H), 6.80 (d, J=6.8 Hz, 1H), 3.97 (s, 3H).

Step III

Compound 43c (200 mg, 0.89 mmol) was dissolved in methanol (20 mL), and wet palladium on carbon (20 mg, 10%, moisture content: 50%) was added. The reaction mixture was stirred under a hydrogen (15 psi) atmosphere for 16 hr at room temperature, and then filtered. The filtrate was concentrated under reduced pressure to dryness, to give Compound 43d (200 mg, white solid, yield: 99%). $^1$H NMR (400 MHz, CD₃OD) δ 8.16-8.11 (m, 2H), 7.80 (d, J=8.4 Hz, 1H), 3.95 (s, 3H), 3.62-3.56 (m, 2H), 3.48-3.43 (m, 2H).

Step IV

Compound 43d (150 mg, 0.66 mmol) was dissolved in tetrahydrofuran (5 mL), and a solution of diisobutyl aluminum hydride (2.65 mmol, 1 M, 2.65 mL) was slowly added dropwise at 5-15° C. The reaction mixture was stirred for 4 hr, and then water (10 mL) and 1 N hydrochloric acid (5 mL) were added. The resulting mixture was extracted with ethyl acetate (20 mL×2). The organic phases were combined, dried over anhydrous sodium sulfate, filtered, concentrated under reduced pressure to dryness, and separated and purified by thin-layer silica gel chromatoplates (petroleum ether/ethyl acetate=1/1), to give Compound 43e (80 mg, white solid, yield: 60%). ¹H NMR (400 MHz, CD₃OD) δ 7.66 (d, J=7.6 Hz, 1H), 7.52-7.46 (m, 2H), 4.70 (s, 2H), 3.58-3.50 (m, 2H), 3.43-3.36 (m, 2H).

Step V

Compound 43e (80.00 mg, 403.55 mmol) was dissolved in dichloromethane (10 mL), and manganese dioxide (281 mg, 3.23 mmol) was added. The reaction mixture was stirred for 3 hr at room temperature, and then filtered. The filtrate was directly concentrated to dryness, to give Compound 43f (71 mg, white solid, yield: 89%). ¹H NMR (400 MHz, CDCl₃) δ 10.10 (s, 1H), 8.02-7.96 (m, 1H), 7.95-7.89 (m, 2H), 3.62-3.45 (m, 4H).

Step VI

Compound 43 was synthesized from Compound 43f and Compound 6b according to the method in Example 1 (44 mg, yield: 31%). ¹H NMR (400 MHz, CD₃OD) δ 7.57-7.55 (m, 1H), 7.38-7.36 (m, 1H), 7.26 (s, 1H), 7.25-7.19 (m, 1H), 7.00-6.92 (m, 1H), 6.87-6.79 (m, 1H), 4.93 (s, 2H), 4.15 (s, 2H), 3.51-3.43 (m, 2H), 3.30-3.26 (m, 2H), 2.35 (s, 3H). MS-ESI calculated value [M+H]⁺ 388, measured value 388.

Example 44

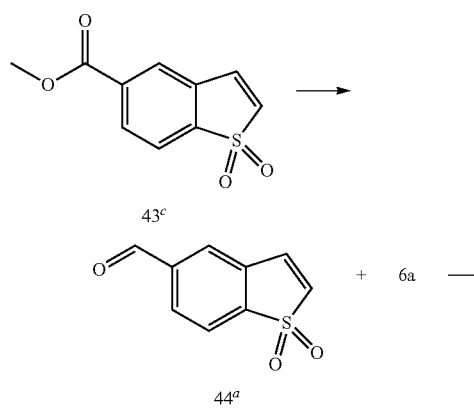

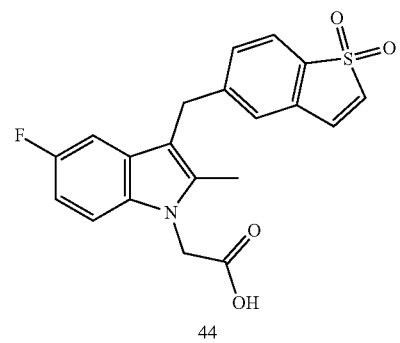

Step I

Compound 44a was synthesized from Compound 43c through a two-step reaction according to the method in Example 43 (71 mg, white solid, yield: 41%). MS-ESI calculated value [M+H]⁺ 195, measured value 195.

Step II

Compound 44 was synthesized from Compound 44a and Compound 6a according to the method in Example 1 (4 mg, yield: 7%). ¹H NMR (400 MHz, CD₃OD) δ 7.58 (d, =7.6 Hz, 1H), 7.43 (d, J=7.6 Hz, 1H), 7.33 (d, J=6.8 Hz, 1H), 7.29 (s, 1H), 7.26-7.20 (m, 1H), 7.02-6.96 (m, 1H), 6.90 (d, J=6.8 Hz, 1H), 6.88-6.82 (m, 1H), 4.94 (s, 2H), 4.17 (s, 2H), 2.35 (s, 3H). MS-ESI calculated value [M+H]⁺ 386, measured value 386.

Example 45

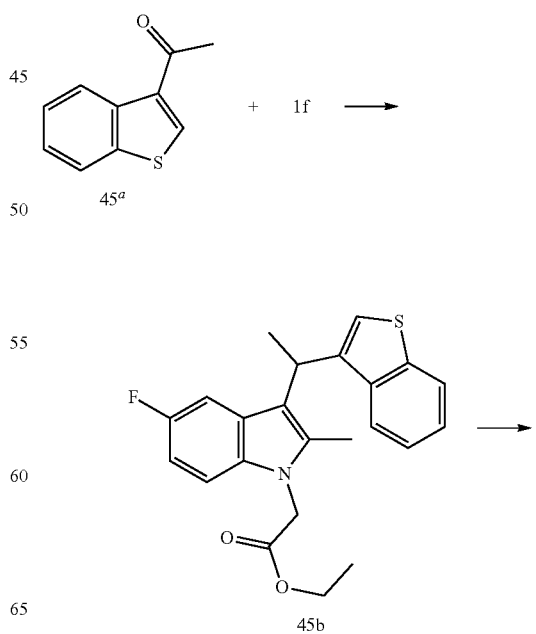

-continued

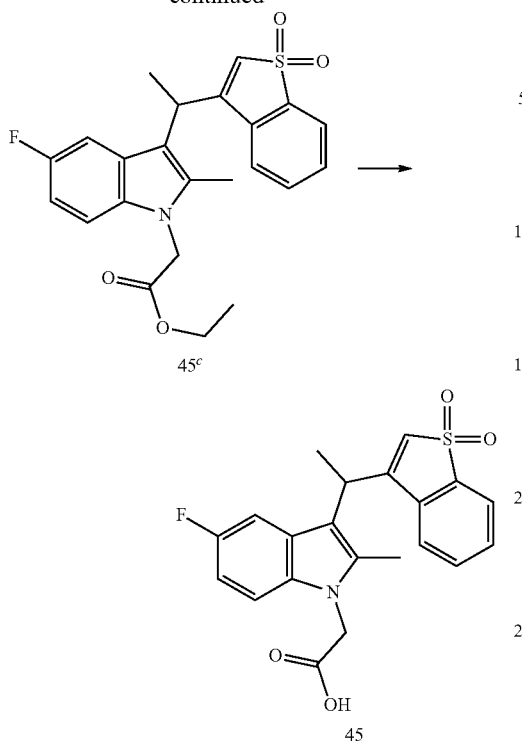

Step I

Compound 45b was synthesized from Compound 45a and Compound 1f according to the method in Example 1 (100 mg, yield: 39%).

Step II

At room temperature, sodium perborate tetrahydrate (292 mg, 1.90 mmol) was added to a solution of Compound 45b (300 mg, 0.76 mmol) in 1 mL of acetic acid. The reaction mixture was reacted for 1 hr at 45° C. After completion of the reaction, 30 mL of a saturated solution of sodium bicarbonate was added to the reaction mixture, and the resulting mixture was extracted with ethyl acetate (20 mL×3). The organic phase was washed with a saturated aqueous solution of sodium chloride, dried over anhydrous sodium sulfate, filtered, concentrated, and purified by thin-layer chromatography (petroleum ether/ethyl acetate 100-10%), to give the target Compound 45c (45 mg, yellowish oil, yield: 15%).

Step III

Compound 45 was synthesized from Compound 45c according to the method in Example 1 (7 mg, yield: 18%). $^1$H NMR (400 MHz, CD$_3$OD) δ 7.66 (s, 1H), 7.50-7.44 (m, 1H), 7.42-7.37 (m, 1H), 7.28-7.20 (m, 3H), 7.12-7.11 (m, 1H), 6.89-6.84 (m, 1H), 4.93-4.92 (m, 2H), 4.55-4.44 (m, 1H), 2.43 (s, 3H), 1.71-1.69 (m, 3H). MS-ESI calculated value [M+H]$^+$ 400, measured value 400.

Example 46

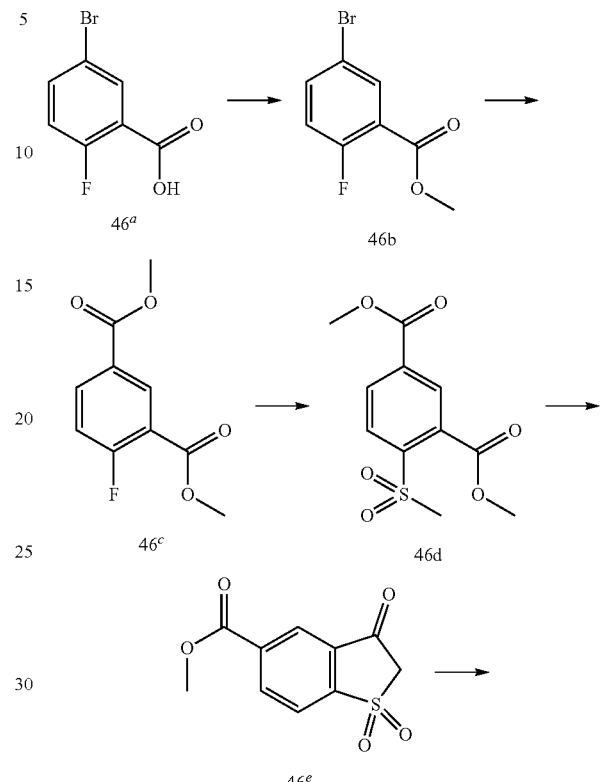

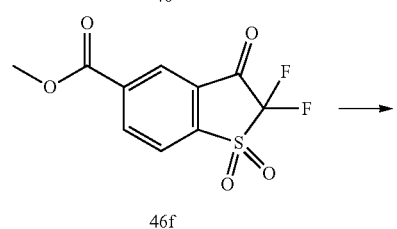

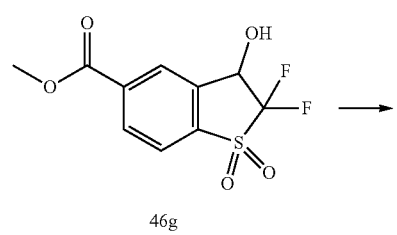

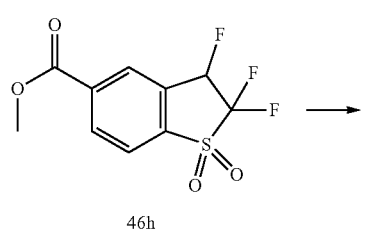

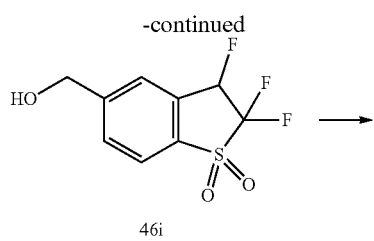

46i

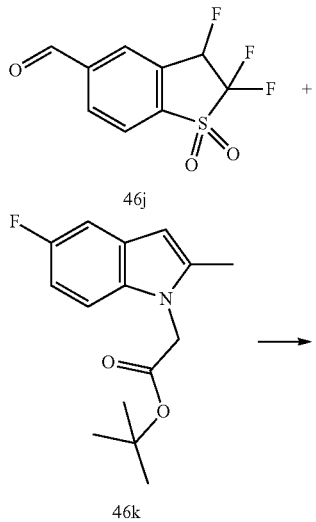

46j

46k

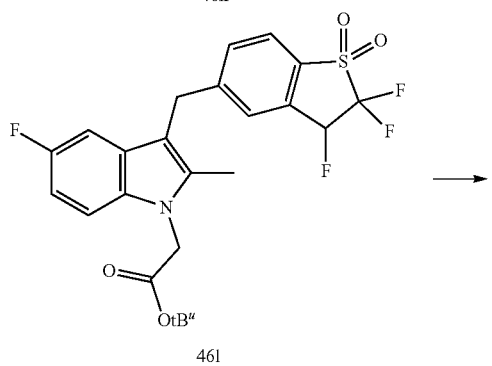

46l

46

Step I

Compound 46a (25.00 g, 114.15 mmol) was dissolved in methanol (250 mL), and concentrated sulfuric acid (5.60 g, 57.08 mmol) was slowly added dropwise. The resulting reaction mixture was stirred under reflux for 5 hr at 70° C. After completion of the reaction, the reaction system was adjusted with a saturated solution of sodium bicarbonate to pH 7, concentrated under reduced pressure to remove most of methanol, and then extracted with ethyl acetate (250 mL×2). The organic phases were combined, dried, concentrated under reduced pressure to dryness, and purified by silica gel column chromatography (petroleum ether/ethyl acetate=100-0%) to give Compound 46b (25.00 g). $^1$H NMR (400 MHz, CDCl$_3$) δ 3.93 (s, 3H) 7.04 (t, J=8.8 Hz, 1H) 7.59-7.62 (m, 1H), 8.04-8.07 (m, 1H). MS-ESI calculated value [M+H]$^+$ 234, measured value 234.

Step II

Compound 46b (24.00 g, 102.99 mmol) was dissolved in methanol (300 mL), and N,N-dimethylformamide (100 mL), triethylamine (100 mL), and [1,1-bis(diphenylphosphino)ferrocene]dichloropalladium (12.62 g, 15.45 mmol) were added. The reaction mixture was stirred under a carbon monoxide atmosphere (50 psi) for 16 hr at 80° C., filtered, concentrated under reduced pressure, and extracted with ethyl acetate (500 mL×2). The organic phases were combined, dried, concentrated under reduced pressure to dryness, and purified by silica gel column chromatography (petroleum ether/ethyl acetate=100-0%), to give Compound 46c (11.00 g). $^1$H NMR (400 Hz, CDCl$_3$) δ 3.95 (s, 3H), 3.97 (s, 3H), 7.20-7.24 (m, 1H), 8.21-8.23 (m, 1H), 8.63-8.65 (m, 1H). MS-ESI calculated value [M+H]$^+$ 213, measured value 213.

Step III

Compound 46c (11.00 g, 51.85 mmol) was dissolved in dimethyl sulfoxide (50 mL), and sodium methylsulfinate (5.82 g, 57.04 mmol) was added. The resulting reaction mixture was stirred for 16 hr at 90° C., and then poured into ice water (300 mL). The resulting mixture was extracted with ethyl acetate (400 mL×2). The organic phases were combined, dried, concentrated under reduced pressure to dryness, and separated and purified by silica gel column chromatography (petroleum ether/ethyl acetate=100-0%), to give Compound 46d (11.00 g). $^1$H NMR (400 Hz, CDCl$_3$) δ 3.93 (s, 3H), 3.93 (s, 3H), 3.97 (s, 3H), 8.21-8.29 (m, 1H), 8.30-8.36 (m, 1H), 8.37 (s, 1H). MS-ESI calculated value [M+H]$^+$ 273, measured value 273.

Step IV

Compound 46d (10.00 g, 36.73 mmol) was dissolved in tetrahydrofuran (300 mL), and lithium bis(trimethylsilyl)amide (7.99 g, 47.75 mmol) was slowly added dropwise at −78° C. After the resulting reaction mixture was stirred for 3 hr at −78° C., a saturated solution of ammonium chloride was added to quench the reaction and the pH was adjusted to 7. Most of tetrahydrofuran was removed by concentration under reduced pressure, and then the resulting mixture was extracted with ethyl acetate (500 mL×2). The organic phases were combined, dried, and concentrated under reduced pressure to dryness, to give Compound 46e (8.00 g). $^1$H NMR (400 MHz, CDCl$_3$) δ 4.02 (s, 3H), 4.17 (s, 2H), 3.97 (s, 3H), 8.09 (d, J=8.0 Hz, 1H), 8.59-8.61 (m, 1H), 8.66 (s, 1H). MS-ESI calculated value [M+H]$^+$ 241, measured value 241.

Step V

Compound 46e (4.00 g, 16.65 mmol) was dissolved in acetonitrile (50 mL), and anhydrous sodium carbonate (5.29 g, 49.95 mmol) was added. After completion of the addition, the resulting mixture was stirred for 0.5 hr at 20° C., and 1-chloromethyl-4-fluoro-1,4-diazoniabicyclo[2,2,2]octane bis(tetrafluoroborate) (12.98 g, 36.63 mmol) was added. The resulting reaction mixture was stirred for 0.5 hr at 20° C. A saturated solution of ammonium chloride was added to quench the reaction and the pH was adjusted to 7. The resulting mixture was extracted with ethyl acetate (50 mL×2). The organic phases were combined, dried, concentrated under reduced pressure to dryness, and separated and purified by silica gel column chromatography (petroleum ether/ethyl acetate=100-0%), to give Compound 46f (3.40 g). $^1$H NMR (400 MHz, CDCl$_3$) δ 4.05 (s, 3H), 8.18 (d, J=8.0 Hz, 1H), 8.73 (d, J=8.4 Hz, 1H), 8.77 (s, 1H). MS-ESI calculated value [M+H]$^+$ 277, measured value 277.

Step VI

Compound 46f (1.50 g, 5.43 mmol) was dissolved in tetrahydrofuran (30 mL), and sodium borohydride (230 mg, 6.08 mmol) was slowly added at 0° C. After the resulting reaction mixture was stirred for 2 hr at 0° C., 1 N hydrochloric acid was added to quench the reaction and the pH was adjusted to 7. Most of tetrahydrofuran was removed by concentration under reduced pressure, and then the resulting mixture was extracted with ethyl acetate (50 mL×2). The organic phases were combined, dried, concentrated under reduced pressure to dryness, and separated and purified by silica gel column chromatography (petroleum ether/ethyl acetate=100-0%), to give Compound 46g (1.20 g). $^1$H NMR (400 MHz, CDCl$_3$) δ 3.93 (s, 3H), 5.72 (m, 1H), 8.24-8.25 (m, 3H). MS-ESI calculated value [M+H]$^+$ 279, measured value 279.

Step VII

Compound 46g (1.20 g, 4.31 mmol) was dissolved in dichloromethane (20 mL), and diethyl sulfur trifluoride (1.39 g, 8.62 mmol) was slowly added dropwise at 0° C. The resulting reaction mixture was stirred for 16 hr at 20° C. A saturated solution of sodium bicarbonate was added to quench the reaction and the pH was adjusted to 7. The resulting mixture was extracted with dichloromethane (10 mL×2). The organic phases were combined, dried, concentrated under reduced pressure to dryness, and separated and purified by silica gel column chromatography (petroleum ether/ethyl acetate=100-0%), to give Compound 46h (180 mg). $^1$H NMR (400 MHz, CDCl$_3$) δ 4.02 (s, 3H), 5.95-6.13 (m, 1H), 8.00 (dd, J=8.4 Hz, J=1.2 Hz, 1H), 8.40-8.46 (m, 2H). MS-ESI calculated value [M+H]$^+$ 277, measured value 277.

Step VIII

Compound 46h (480 mg, 1.71 mmol) was dissolved in tetrahydrofuran (10 mL), and diisobutyl aluminum hydride (603.67 mg, 4.28 mmol) was slowly added dropwise at 0° C. The resulting reaction mixture was stirred for 5 hr at 20° C. 1 N hydrochloric acid was added to quench the reaction and the pH was adjusted to 7. The resulting mixture was extracted with ethyl acetate (60 mL×2). The organic phases were combined, dried, concentrated under reduced pressure to dryness, and separated and purified by chromatography on silica gel plates (petroleum ether/ethyl acetate=2/1), to give Compound 46i (180 mg). $^1$H NMR (400 MHz, CDCl$_3$) δ 7.88 (d, J=8.0 Hz, 1H), 7.80 (s, 1H), 7.75 (d, J=8.0 Hz, 1H), 5.89-6.08 (m, 1H), 4.90 (s, 2H). MS-ESI calculated value [M+H]$^+$ 253, measured value 253.

Step IX

Compound 46i (180 mg, 0.71 mmol) was dissolved in dichloromethane (10 mL), and then manganese dioxide (496 mg, 5.71 mmol) was added. The resulting reaction mixture was stirred for 2 hr at 20° C., filtered, and concentrated under reduced pressure to dryness, to give Compound 46j (160 mg). $^1$H NMR (400 MHz, CDCl$_3$) δ 10.17 (s, 1H), 8.24-8.33 (m, 2H), 8.11 (d, J=8.0 Hz, 1H), 5.99-6.18 (m, 1H). MS-ESI calculated value [M+H]$^+$ 251, measured value 251.

Step X

Compound 46j (52 mg, 0.21 mmol) and Compound 46k (60 mg, 0.23 mmol) were dissolved in 1,2-dichloroethane (5 mL), and triethylsilane (193 mg, 1.66 mmol) and trifluoroacetic acid (118 mg, 1.04 mmol) were added at 0° C. The reaction mixture was stirred for 2 hr at 60° C., and then water (5 mL) was added to quench the reaction. The resulting mixture was adjusted with a saturated solution of sodium bicarbonate to pH 7, and extracted with dichloromethane (50 ml×2). The organic phases were combined, dried, concentrated under reduced pressure to dryness, and separated and purified by chromatography on silica gel plates (petroleum ether/ethyl acetate=4/1), to give Compound 46l (50 mg). MS-ESI calculated value [M+H]$^+$ 498, measured value 498.

Step XI

Compound 46l (40 mg, 0.08 mmol) was dissolved in dichloromethane (5 mL), and then trifluoroacetic acid (9 mg, 0.0091 mmol) was added. The reaction mixture was stirred for 2 hr at 20° C., concentrated under reduced pressure to dryness, and separated and purified by high performance liquid chromatography, to give Compound 46 (24 mg). $^1$H NMR (400 MHz, DMSO-d$_6$) δ 8.12 (d, J=8.0 Hz, 1H), 7.71-7.80 (m, 2H), 7.38 (dd, J=8.4, J=4.4 Hz, 1H), 7.22 (d, J=7.6 Hz, 1H), 6.89 (t, J=8.4 Hz, 1H), 6.67-6.85 (m, 1H), 4.97 (s, 2H), 4.24 (s, 2H), 2.33 (s, 3H). MS-ESI calculated value [M+H]$^+$ 442, measured value 442.

Example 47

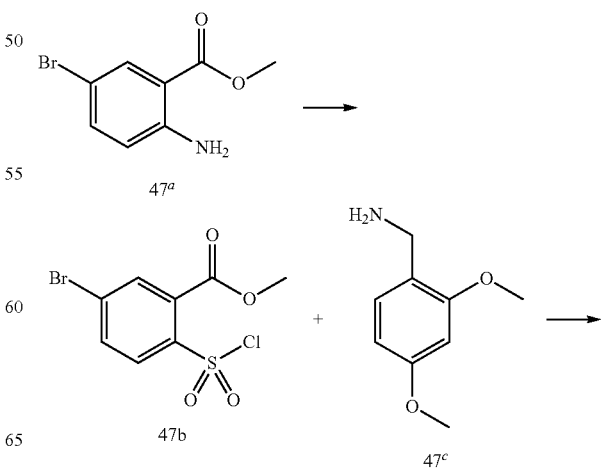

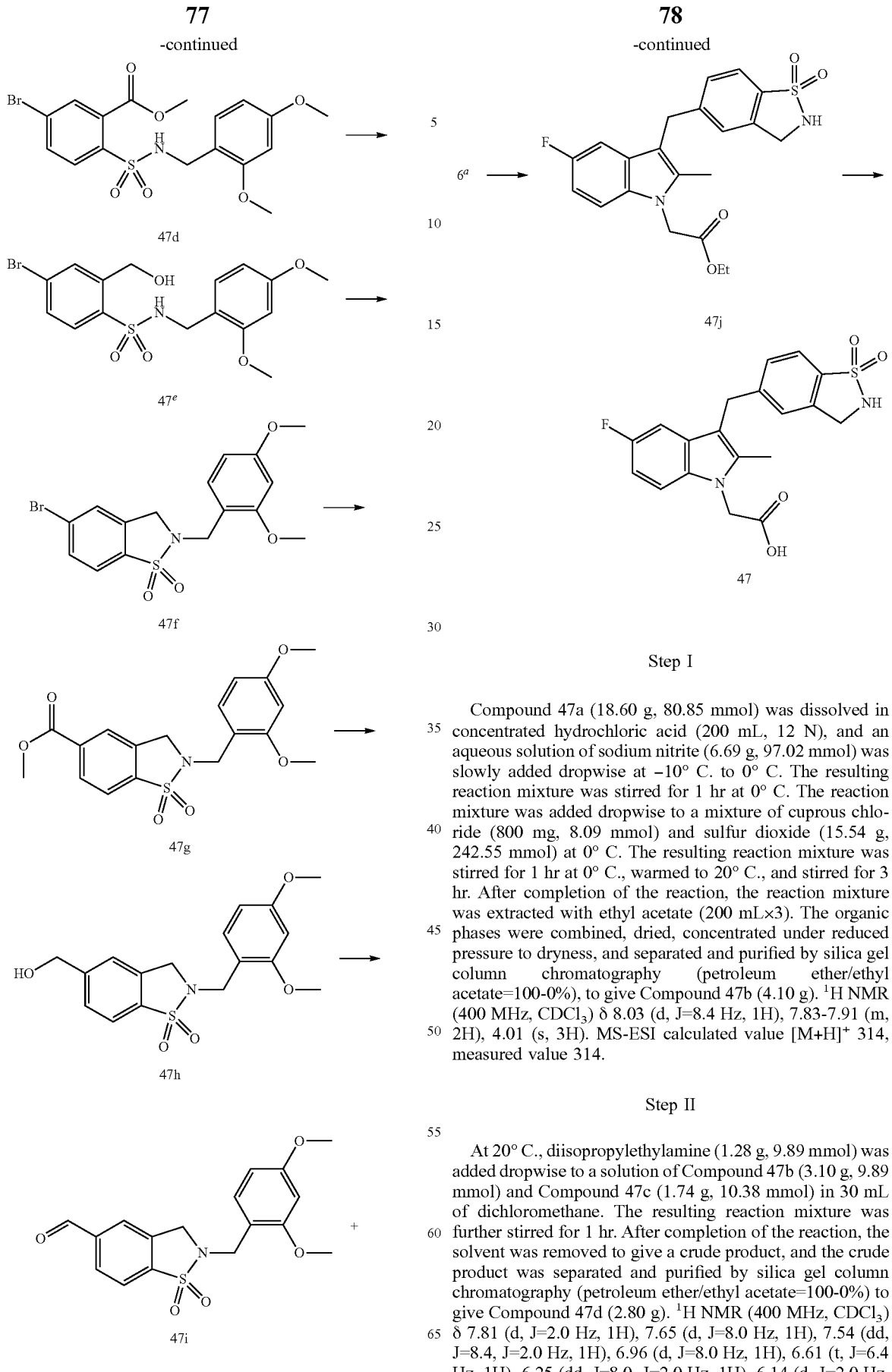

Step I

Compound 47a (18.60 g, 80.85 mmol) was dissolved in concentrated hydrochloric acid (200 mL, 12 N), and an aqueous solution of sodium nitrite (6.69 g, 97.02 mmol) was slowly added dropwise at −10° C. to 0° C. The resulting reaction mixture was stirred for 1 hr at 0° C. The reaction mixture was added dropwise to a mixture of cuprous chloride (800 mg, 8.09 mmol) and sulfur dioxide (15.54 g, 242.55 mmol) at 0° C. The resulting reaction mixture was stirred for 1 hr at 0° C., warmed to 20° C., and stirred for 3 hr. After completion of the reaction, the reaction mixture was extracted with ethyl acetate (200 mL×3). The organic phases were combined, dried, concentrated under reduced pressure to dryness, and separated and purified by silica gel column chromatography (petroleum ether/ethyl acetate=100-0%), to give Compound 47b (4.10 g). $^1$H NMR (400 MHz, CDCl$_3$) δ 8.03 (d, J=8.4 Hz, 1H), 7.83-7.91 (m, 2H), 4.01 (s, 3H). MS-ESI calculated value [M+H]$^+$ 314, measured value 314.

Step II

At 20° C., diisopropylethylamine (1.28 g, 9.89 mmol) was added dropwise to a solution of Compound 47b (3.10 g, 9.89 mmol) and Compound 47c (1.74 g, 10.38 mmol) in 30 mL of dichloromethane. The resulting reaction mixture was further stirred for 1 hr. After completion of the reaction, the solvent was removed to give a crude product, and the crude product was separated and purified by silica gel column chromatography (petroleum ether/ethyl acetate=100-0%) to give Compound 47d (2.80 g). $^1$H NMR (400 MHz, CDCl$_3$) δ 7.81 (d, J=2.0 Hz, 1H), 7.65 (d, J=8.0 Hz, 1H), 7.54 (dd, J=8.4, J=2.0 Hz, 1H), 6.96 (d, J=8.0 Hz, 1H), 6.61 (t, J=6.4 Hz, 1H), 6.25 (dd, J=8.0, J=2.0 Hz, 1H), 6.14 (d, J=2.0 Hz, 1H), 4.19 (d, J=6.4 Hz, 2H), 3.95 (s, 3H), 3.75 (s, 3H), 3.62 (s, 3H). MS-ESI calculated value [M+H]+ 445, measured value 445.

Step III

Compound 47e (1.85 g) was synthesized from Compound 47d according to the synthesis method of Compound 46i in Example 46. $^1$H NMR (400 MHz, CDCl$_3$) δ 7.69 (d, J=8.4 Hz, 1H), 7.57 (s, 1H), 7.45 (dd, J=8.4, J=2.0 Hz, 1H), 6.89 (d, J=8.0 Hz, 1H), 6.25-6.33 (m, 2H), 5.55 (t, J=5.6 Hz, 1H), 4.83 (d, J=6.8 Hz, 2H), 4.07-4.12 (m, 2H), 3.78 (s, 3H), 3.71 (s, 3H), 2.63-2.72 (m, 1H). MS-ESI calculated value [M+H]+ 417, measured value 417.

Step IV

Compound 47e (1.85 g, 4.44 mmol) was dissolved in tetrahydrofuran (300 mL), and triphenylphosphine (2.33 g, 8.88 mmol) and diisopropyl azodicarboxylate (1.80 g, 8.88 mmol) were added under the protection of nitrogen. The reaction mixture was stirred for 16 hr at 20° C. After completion of the reaction, water (30 mL) was added to quench the reaction. Most of tetrahydrofuran was removed by concentration under reduced pressure, and then the resulting mixture was extracted with ethyl acetate (200 mL×3). The organic phases were combined, dried, concentrated under reduced pressure to dryness, and separated and purified by silica gel column chromatography (petroleum ether/ethyl acetate=100-0%), to give Compound 47f (2.80 g). $^1$H NMR (400 MHz, CDCl$_3$) δ 7.62-7.71 (m, 2H), 7.48 (brs, 1H), 7.32 (d, J=8.8 Hz, 1H), 6.47-6.52 (m, 2H), 4.44 (s, 2H), 4.23 (s, 2H), 3.85 (s, 3H), 3.82 (s, 3H). MS-ESI calculated value [M+H]+ 399, measured value 399.

Step V

Compound 47g (2.11 g) was synthesized from Compound 47f according to the synthesis method of Compound 46c in Example 46. $^1$H NMR (400 MHz, CDCl$_3$) δ 8.18 (d, J=8.0 Hz, 1H), 8.14-8.21 (m, 1H), 8.01 (s, 1H), 7.89 (d, J=8.0 Hz, 1H), 7.34 (d, J=8.8 Hz, 1H), 6.48-6.53 (m, 2H), 4.48 (s, 2H), 4.30 (s, 2H), 3.96 (s, 3H), 3.87 (s, 3H), 3.82 (s, 3H). MS-ESI calculated value [M+H]+ 378, measured value 378.

Step VI

Compound 47h (810 mg) was synthesized from Compound 47g according to the synthesis method of Compound 46i in Example 46. $^1$H NMR (400 MHz, CDCl$_3$) δ 7.75 (d, J=8.0 Hz, 1H), 7.45 (d, J=8.0 Hz, 1H), 7.31-7.36 (m, 2H), 6.47-6.53 (m, 2H), 5.31 (s, 1H), 4.77 (brs, 2H), 4.44 (s, 2H), 4.23 (s, 2H), 3.86 (s, 3H), 3.82 (s, 3H). MS-ESI calculated value [M+H]+ 350, measured value 350.

Step VII

Compound 47i (640 mg) was synthesized from Compound 47h according to the synthesis method of Compound 43f in Example 43. $^1$H NMR (400 MHz, CDCl$_3$) δ 10.09 (s, 1H), 7.98-8.05 (m, 2H), 7.85 (s, 1H), 7.34 (d, J=9.2 Hz, 1H), 6.48-6.53 (m, 2H), 4.49 (s, 2H), 4.34 (s, 2H), 3.87 (s, 3H), 3.83 (s, 3H). MS-ESI calculated value [M+H]+ 348, measured value 348.

Step VIII

Compound 47j (13 mg) was synthesized from Compound 47i and Compound 6a according to the synthesis method of Compound 6c in Example 6. MS-ESI calculated value [M+H]+ 417, measured value 417.

Step IX

Compound 47 (9 mg) was synthesized from Compound 47j according to the synthesis method in Example 1. $^1$H NMR (400 MHz, DMSO-d$_6$) δ 7.67 (d, J=8.0 Hz, 2H), 7.39 (brs, J=8.8 Hz, 1H), 7.34 (s, 1H), 7.16 (dd, J=9.6, J=2.4 Hz, 1H), 6.87 (td, J=9.6, J=2.4 Hz, 1H), 4.96 (s, 2H), 4.32 (d, J=4.8 Hz, 2H), 4.12 (s, 2H), 2.35-2.35 (m, 1H), 2.32 (s, 2H), 2.07 (s, 1H). MS-ESI calculated value [M+H]+ 389, measured value 389.

Example 48

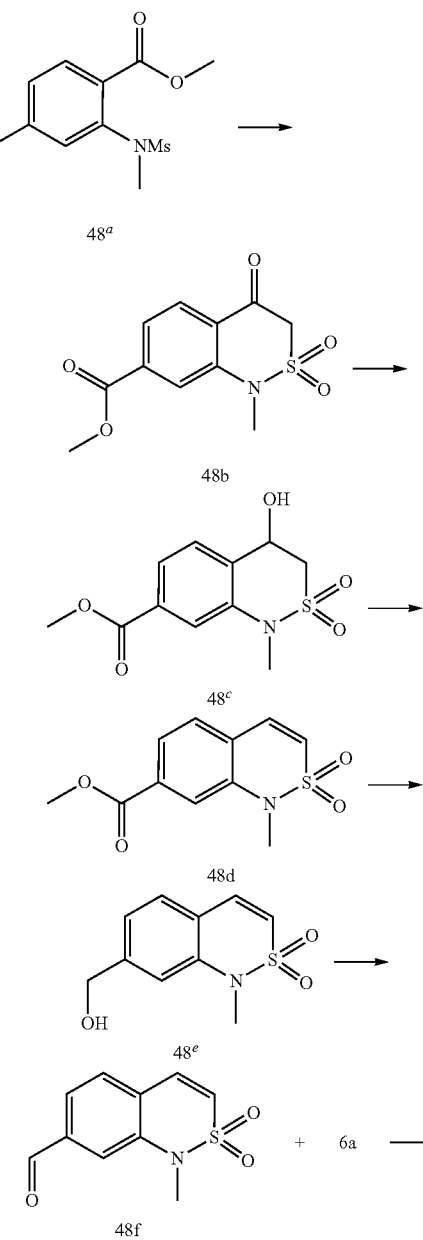

-continued

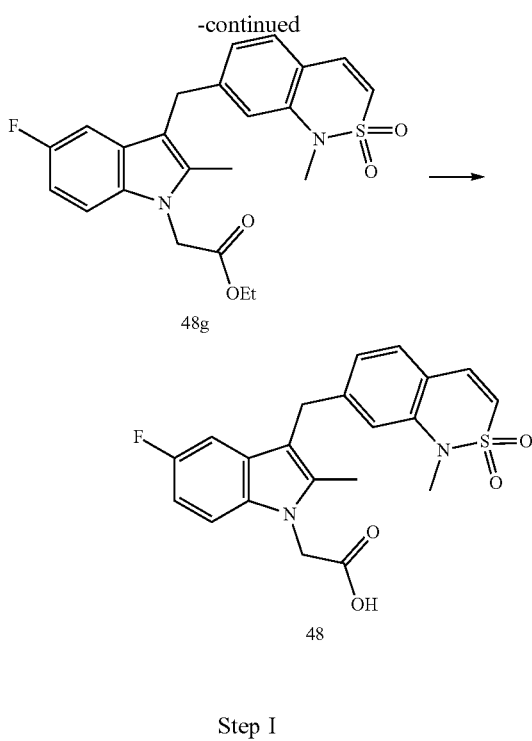

Step I

Compound 48a (5.80 g, 19.25 mmol) was dissolved in tetrahydrofuran (150 mL), and sodium hydride (1.54 g, 38.50 mmol, 60%) was added in batch at 0° C. The resulting reaction mixture was stirred for 3 hr at 20° C. After completion of the reaction, a saturated solution of ammonium chloride was added to quench the reaction and the pH was adjusted to 6-7. Most of tetrahydrofuran was removed by concentration under reduced pressure, and then the resulting mixture was extracted with ethyl acetate (100 mL×3). The organic phases were combined, dried, and concentrated under reduced pressure to dryness to give Compound 48b (5.00 g). $^1$H NMR (400 MHz, CDCl$_3$) δ 8.21 (d, J=8.4 Hz, 1H), 8.06-8.12 (m, 1H), 7.89 (d, J=8.0 Hz, 1H), 4.39 (s, 2H), 3.95-4.01 (m, 3H), 3.00 (s, 3H). MS-ESI calculated value [M+H]$^+$ 270, measured value 270.

Step II

Compound 48b (3.00 g, 11.14 mmol) was dissolved in tetrahydrofuran (30 mL), and sodium borohydride (506 mg, 13.37 mmol) was added in batch at 0° C. The resulting reaction mixture was stirred for 0.5 hr at 20° C. After completion of the reaction, a saturated solution of ammonium chloride was added to quench the reaction and the pH was adjusted to 6-7. Most of tetrahydrofuran was removed by concentration under reduced pressure, and then the resulting mixture was extracted with ethyl acetate (50 mL×2). The organic phases were combined, dried, concentrated under reduced pressure to dryness, and separated and purified by silica gel column chromatography (petroleum ether/ethyl acetate=100-0%), to give Compound 48c (2.70 g). MS-ESI calculated value [M+H]$^+$ 272, measured value 272.

Step III

At −10° C., methanesulfonyl chloride (1.70 g, 14.84 mmol) was slowly added dropwise to a solution of Compound 48c (1.30 g, 4.79 mmol) and triethylamine (2.42 g, 23.96 mmol) in 30 mL of dichloromethane. The resulting reaction mixture was warmed to 20° C., and further stirred for 1 hr. Then, 1,8-diazabicyclo[5.4.0]undec-7-ene (3.65 g, 23.96 mmol) was added. The resulting reaction mixture was further stirred for 1 hr at 20° C. After completion of the reaction, at 0° C., a saturated solution of ammonium chloride was added to quench the reaction, and the pH was adjusted to 6-7. The resulting mixture was extracted with dichloromethane (30 mL×2). The organic phases were combined, dried, concentrated under reduced pressure to dryness, and separated and purified by silica gel column chromatography (petroleum ether/ethyl acetate=100-0%), to give Compound 48d (1.13 g). $^1$H NMR (400 MHz, CDCl$_3$) δ 7.75-7.91 (m, 2H), 7.51 (d, J=8.0 Hz, 1H), 7.33 (d, J=10.0 Hz, 1H), 6.88 (d, J=10 Hz, 1H), 3.98 (s, 3H), 3.58 (s, 3H). MS-ESI calculated value [M+H]$^{30}$ 254, measured value 254.

Step IV

Compound 48e (90 mg) was synthesized from Compound 48d according to the synthesis method of Compound 43e in Example 43. $^1$H NMR (400 MHz, CDCl$_3$) δ 7.42 (d, J=8.0 Hz, 1H), 7.21 (s, 1H), 7.13-7.18 (m, 1H), 6.99-7.06 (m, 1H), 6.75 (d, J=10.0 Hz, 1H), 4.81 (d, J=6.0 Hz, 2H), 4.70 (d, J=6.0 Hz, 1H), 3.52 (s, 3H). MS-ESI calculated value [M+H]$^+$ 226, measured value 226.

Step V

Compound 48f (40 mg) was synthesized from Compound 48e according to the synthesis method of Compound 43f in Example 43. $^1$H NMR (400 MHz, CDCl$_3$) δ 10.4 (s, 1H), 7.67-7.72 (m, 2H), 7.60-7.66 (m, 1H), 7.35 (d, J=10.4 Hz, 1H), 6.93 (d, J=10.4 Hz, 1H), 3.60 (s, 3H). MS-ESI calculated value [M+H]$^+$ 224, measured value 224.

Step VI

Compound 48g (23 mg) was synthesized from Compound 48f and Compound 6a according to the synthesis method of Compound 6c in Example 6. MS-ESI calculated value [M+H]$^+$ 443, measured value 443.

Step VII

Compound 48 (9 mg) was synthesized from Compound 48g according to the synthesis method in Example 1. $^1$H NMR (400 MHz, DMSO-d$_6$) δ 7.44-7.54 (m, 2H), 7.36 (dd, J=9.2, J=4.4 Hz, 1H), 7.19-7.26 (m, 2H), 7.15 (d, J=10.0 Hz, 1H), 7.01 (d, J=8.2 Hz, 1H), 6.81-6.91 (m, 1H), 4.97 (s, 2H), 4.12 (s, 2H), 2.35 (s, 3H). MS-ESI calculated value [M+H]$^+$ 415, measured value 415.

Example 49

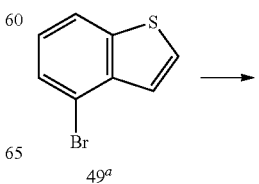

49a

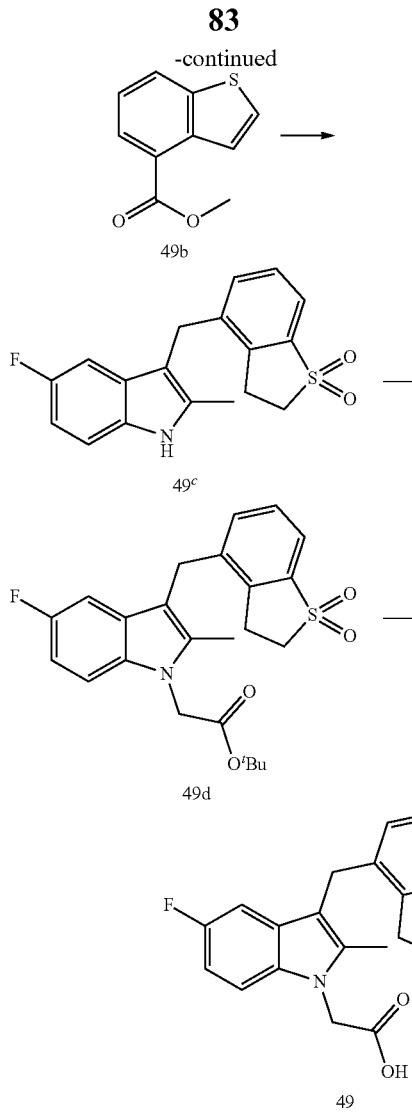

Step I

Compound 49b (5.80 g) was synthesized from Compound 49a according to the synthesis method of Compound 46c in Example 46. $^1$H NMR (400 MHz, CDCl$_3$) δ 8.25-5.24 (d, J=6.4 Hz, 1H), 8.15-8.08 (m, 2H), 7.64-7.63 (d, J=6.4 Hz, 1H), 7.43-7.39 (t, J=8.0, 1H), 4.00 (s, 3H).

Step II

Compound 49c (105 mg) was synthesized from Compound 49b through a multi-step reaction according to the synthesis method in Example 43. $^1$H NMR (400 MHz, CDCl$_3$) δ 7.94 (s, 1H), 7.63-7.62 (m, 1H), 7.40-7.36 (m, 1H), 7.30 (s, 1H), 7.26-7.22 (m, 1H), 6.88-6.87 (m, 1H), 4.03 (s, 2H), 3.54-3.51 (m, 2H), 3.36-3.32 (m, 2H), 2.34 (s, 3H).

Step III

Cesium carbonate (156 mg, 0.48 mmol) and t-butyl bromoacetate (93 mg, 0.48 mmol) were added to a solution of Compound 49c (105 mg, 0.32 mmol) in N,N-dimethylformamide (5 mL) at 25° C. After the resulting reaction mixture was further stirred for 1 hr, a saturated solution of ammonium chloride (30 mL) was added to the reaction system to quench the reaction, and then the resulting mixture was extracted with ethyl acetate (50 mL×3). The organic phases were combined, washed with a saturated solution of sodium chloride (30 mL×3), dried over anhydrous sodium sulfate, filtered, and concentrated under reduced pressure to give Compound 49d (141 mg). MS-ESI calculated value [M+H]$^+$ 443, measured value 443.

Step IV

Compound 49 (25 mg) was synthesized from Compound 49c according to the synthesis method of Compound 12 in Example 12. $^1$H NMR (400 MHz, DMSO-d$_6$) δ 7.56-7.54 (m, 1H), 7.40-7.35 (m, 2H), 7.26-7.24 (m, 1H), 7.05-7.03 (m, 1H), 7.02-6.86 (m, 1H), 4.88 (s, 2H), 4.09 (s, 2H), 3.60-3.57 (m, 2H), 3.35-3.30 (m, 2H), 2.27 (m, 3H). MS-ESI calculated value [M+H]$^+$ 388, measured value 388.

Example 50

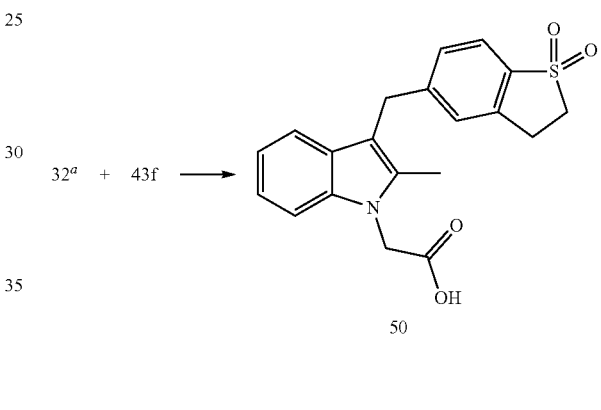

Step I

Compound 50 (16 mg) was synthesized from Compound 32a and Compound 43f according to the synthesis method of Compound 12 in Example 12. $^1$H NMR (400 MHz, DMSO-d$_6$) δ 7.61-7.59 (m, 1H), 7.38-7.32 (m, 4H), 7.04-7.02 (m, 1H), 6.97-6.95 (m, 1H), 4.91 (s, 2H), 4.13 (s, 2H), 3.53-3.51 (m, 2H), 3.27-3.23 (m, 2H), 2.34 (s, 3H). MS-ESI calculated value [M+H]$^+$ 370, measured value 370.

Example 51

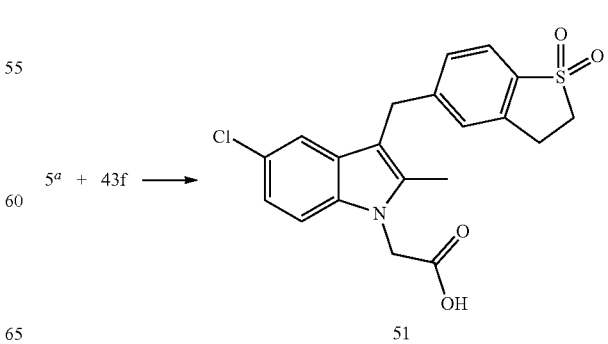

Step I

Compound 51 (84 mg) was synthesized from Compound 5a and Compound 43f according to the synthesis method of Compound 12 in Example 12. $^1$H NMR (400 MHz, DMSO-$d_6$) δ 7.63-7.61 (m, 1H), 7.43-7.30 (m, 3H), 7.05 (s, 1H), 7.05-7.03 (m, 1H), 4.97 (s, 2H), 4.13 (s, 2H), 3.54-3.51 (m, 2H), 3.26-3.24 (m, 2H), 2.32 (s, 3H). MS-ESI calculated value [M+H]$^+$ 404, measured value 404.

Example 52

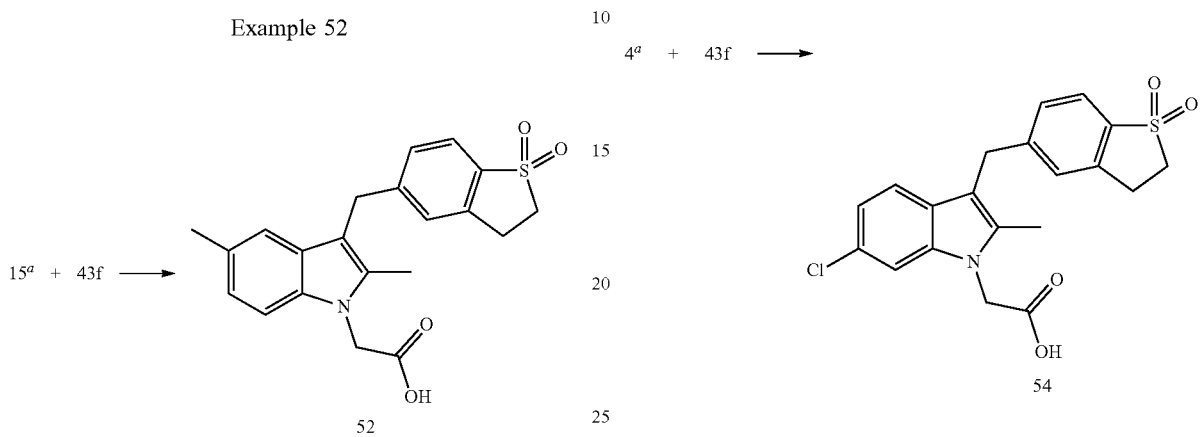

52

Step I

Compound 52 (28 mg) was synthesized from Compound 15a and Compound 43f according to the synthesis method of Compound 12 in Example 12. $^1$H NMR (400 MHz, DMSO-$d_6$) δ 7.61-7.59 (m, 1H), 7.35-7.33 (m, 1H), 7.29 (s, 1H), 7.23-7.21 (m, 1H), 7.16 (s, 1H), 6.87-6.85 (m, 1H), 4.90 (s, 2H), 4.10 (s, 2H), 3.54-3.52 (m, 2H), 3.25 (s, 2H), 2.32 (s, 3H), 2.30 (s, 3H). MS-ESI calculated value [M+H]$^+$ 384, measured value 384.

Example 53

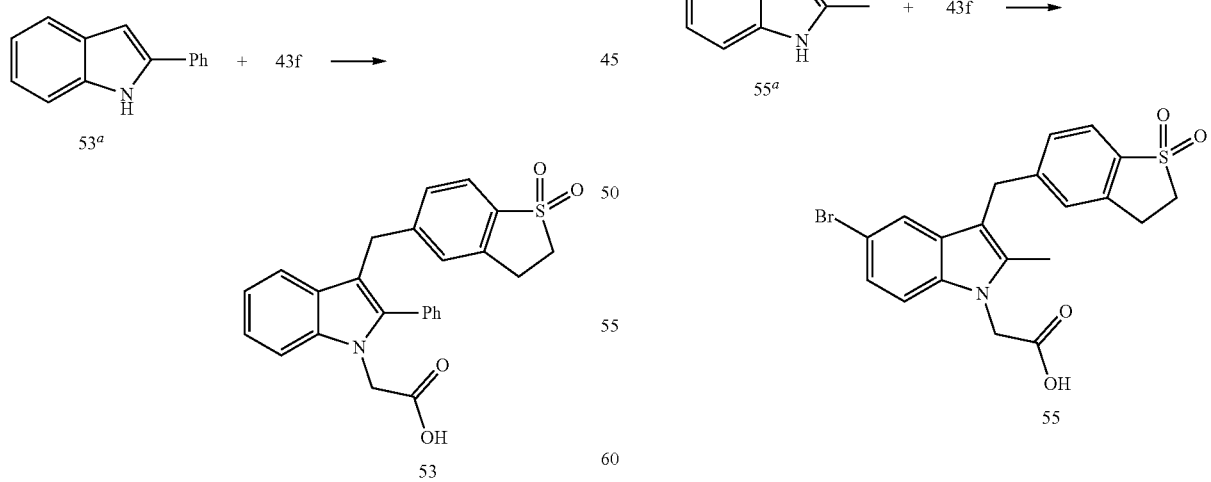

53

Step I

Compound 53 (21 mg) was synthesized from Compound 53a and Compound 43f according to the synthesis method of Compound 12 in Example 12. $^1$H NMR (400 MHz, DMSO-$d_6$) δ 7.56-7.39 (m, 8H), 7.39-7.20 (m, 3H), 7.04 (s, 1H), 4.78 (s, 2H), 4.07 (s, 2H), 3.52-3.49 (m, 2H), 3.24-3.20 (m, 2H). MS-ESI calculated value [M+H]$^+$ 432, measured value 432.

Example 54

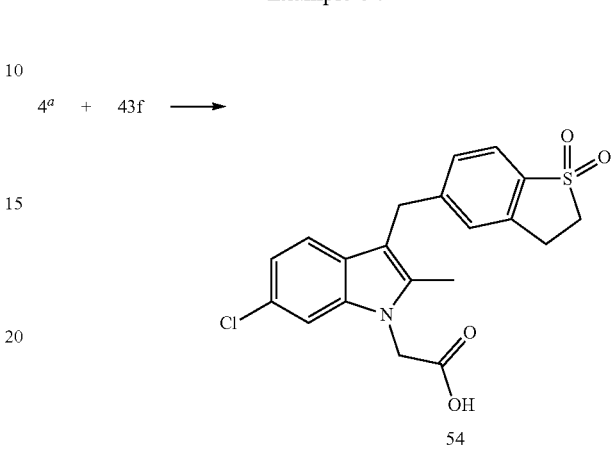

54

Step I

Compound 54 (43 mg) was synthesized from Compound 4a and Compound 43f according to the synthesis method of Compound 12 in Example 12. $^1$H NMR (400 MHz, CD$_3$OD) δ 7.57-7.55 (m, 1H), 7.39 (s, 1H), 7.31-7.30 (m, 2H), 7.26-7.24 (m, 1H), 6.96-6.93 (m, 1H), 4.92 (s, 2H), 4.18 (s, 2H), 3.50-3.46 (m, 2H), 3.28 (s, 2H), 2.35 (s, 3H). MS-ESI calculated value [M+H]$^+$ 404, measured value 404.

Example 55

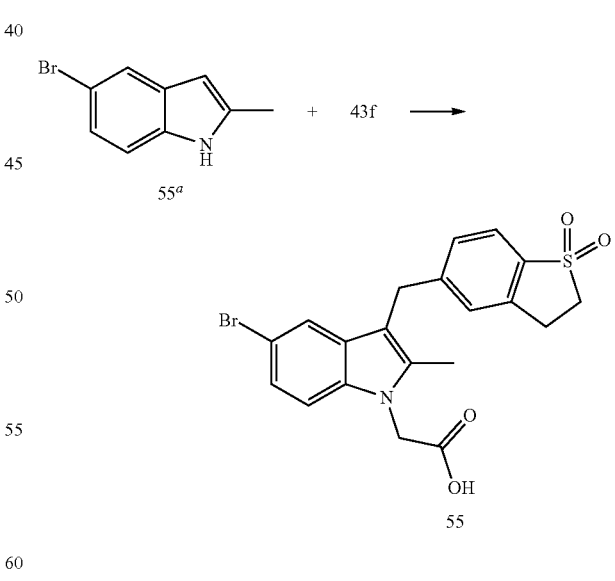

55

Step I

Compound 55 (47 mg) was synthesized from Compound 55a and Compound 43f according to the synthesis method of Compound 12 in Example 12. $^1$H NMR (400 MHz, DMSO-$d_6$) δ 7.63-7.57 (m, 1H), 7.57 (s, 1H), 7.37-7.34 (m, 2H), 7.29 (s, 1H), 7.17-7.15 (m, 1H), 4.98 (s, 2H), 4.13 (s, 2H), 3.54-3.51 (m, 2H), 3.28-3.24 (m, 2H), 2.32 (s, 3H). MS-ESI calculated value [M+H]$^+$ 449, measured value 449.

Example 56

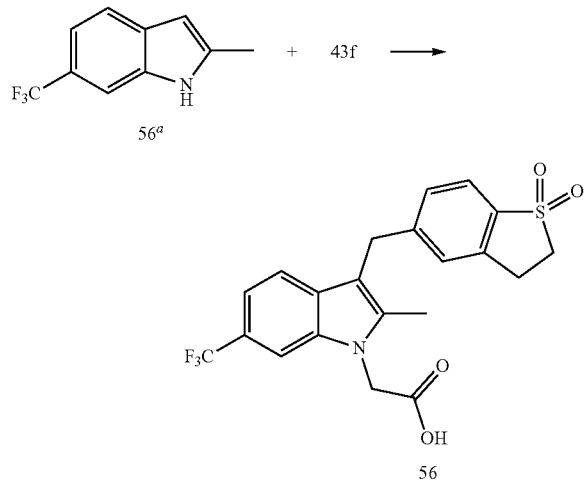

Step I

Compound 56 (47 mg) was synthesized from Compound 56a and Compound 43f according to the synthesis method of Compound 12 in Example 12. $^1$H NMR (400 MHz, DMSO-d$_6$) δ 7.80 (s, 1H), 7.61-7.56 (m, 2H), 7.36-7.32 (m, 2H), 7.25-7.23 (m, 1H), 5.02 (s, 2H), 4.17 (s, 2H), 3.51 (s, 2H), 3.27-3.23 (m, 2H), 2.37 (s, 3H). MS-ESI calculated value [M+H]$^+$ 438, measured value 438.

Example 57

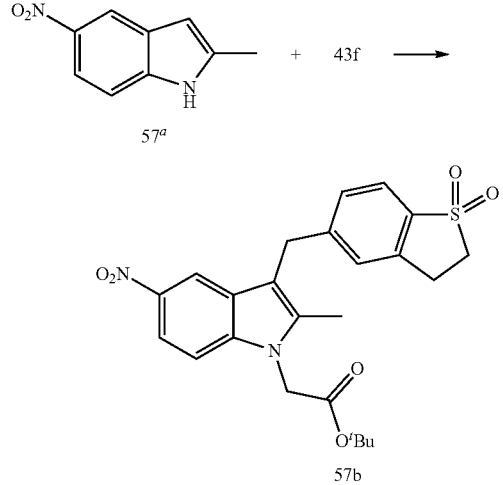

-continued

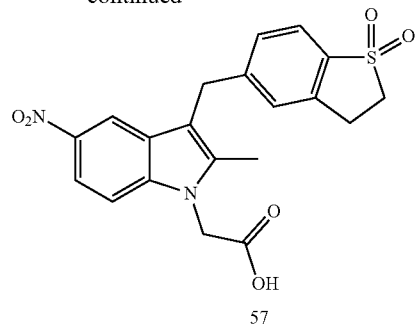

Step I

Compound 57b (480 mg) was synthesized from Compound 57a and Compound 43f according to the synthesis method of Compound 12f in Example 12. MS-ESI calculated value [M+H]$^+$ 471, measured value 471.

Step II

Compound 57 (28 mg) was synthesized from Compound 57b according to the synthesis method of Compound 12 in Example 12. $^1$H NMR (400 MHz, DMSO-d$_6$) δ 8.34 (s, 1H), 7.91-7.89 (m, 1H), 7.63-7.61 (m, 1H), 7.44-7.42 (m, 1H), 7.38-7.36 (m, 1H), 7.33 (s, 1H), 4.59 (s, 2H), 4.23 (s, 2H), 3.54-3.50 (m, 2H), 3.28 (m, 2H), 2.35 (s, 3H). MS-ESI calculated value [M+H]$^+$ 415, measured value 415.

Example 58

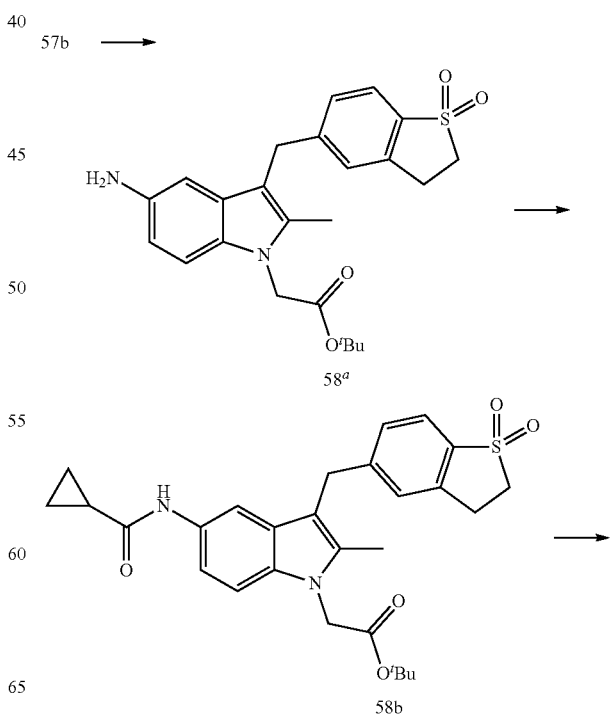

89
-continued

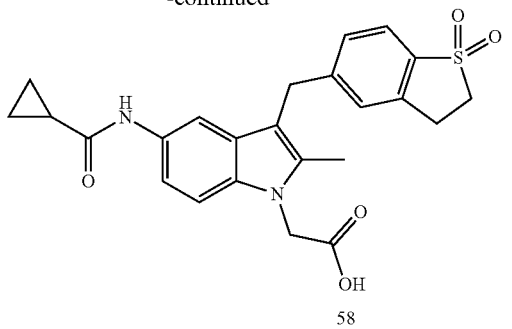

58

Step I

Zinc powder (1.08 g, 16.58 mmol) and an ammonium chloride solution (5 mL, 6 M) were added to a solution of Compound 57b (390 mg, 0.83 mmol) in 5 mL of acetone. The resulting mixture was stirred for 1 hr at 25° C., and filtered. The filtrate was extracted with ethyl acetate (100 mL×5). The organic phases were combined, dried over anhydrous sodium sulfate, filtered, and concentrated under reduced pressure to give a residue. The residue was separated and purified by column chromatography (petroleum ether/ethyl acetate=100-0%) to give Compound 58a (320 mg). MS-ESI calculated value [M+H]$^+$ 441, measured value 441.

Step II

Cyclopropanecarbonyl chloride (24 mg, 0.24 mmol) and diisopropylethylamine (41 mg, 0.32 mmol) were added to a solution of Compound 58a (70 mg, 0.16 mmol) in 5 mL of dichloromethane. After the resulting reaction mixture was stirred for 2 hr at 25° C., a saturated solution of ammonium chloride (20 mL) was added to the reaction system to quench the reaction, and then the resulting mixture was extracted with ethyl acetate (30 mL×3). The organic phases were combined, washed with a saturated solution of sodium chloride (20 mL×1), dried over anhydrous sodium sulfate, filtered, and concentrated under reduced pressure to give a residue. The residue was separated and purified by thin-layer silica gel chromatoplates (petroleum ether/ethyl acetate=1/1) to give Compound 58b (60 mg).

Step III

Compound 58 (4 mg) was synthesized from Compound 58b according to the method in Example 12. $^1$H NMR (400 MHz, DMSO-d$_6$) δ 9.54 (s, 1H), 8.28 (s, 1H), 7.61-7.60 (m, 2H), 7.34-7.32 (m, 1H), 7.28 (s, 1H), 7.18 (s, 2H), 4.60 (s, 2H), 4.07 (s, 2H), 3.68-3.60 (m, 2H), 3.28-3.24 (m, 2H), 2.30 (s, 3H), 1.76-1.74 (m, 1H), 0.75-0.71 (m, 4H). MS-ESI calculated value [M+H]$^+$ 453, measured value 453.

90

Example 59

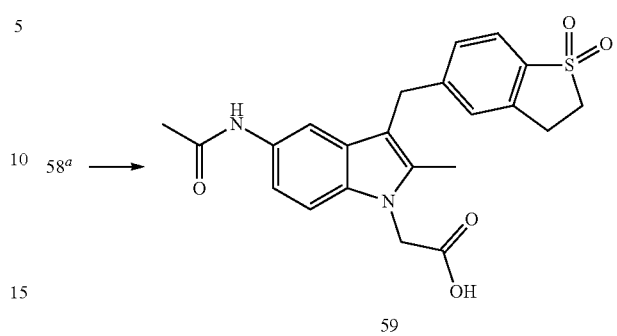

58$^a$ ⟶

59

Step I

Compound 59 (18 mg) was synthesized from Compound 58a according to the method in Example 58. $^1$H NMR (400 MHz, DMSO-d$_6$) δ 9.68 (s, 1H), 8.27 (s, 1H), 7.62-7.56 (m, 2H), 7.34-7.30 (m, 2H), 7.12 (s, 2H), 4.61 (s, 2H), 4.07 (s, 2H), 3.52-3.50 (m, 2H), 3.28-3.26 (m, 2H), 2.31 (s, 3H), 1.98 (m, 3H). MS-ESI calculated value [M+H]$^+$427, measured value 427.

Example 60

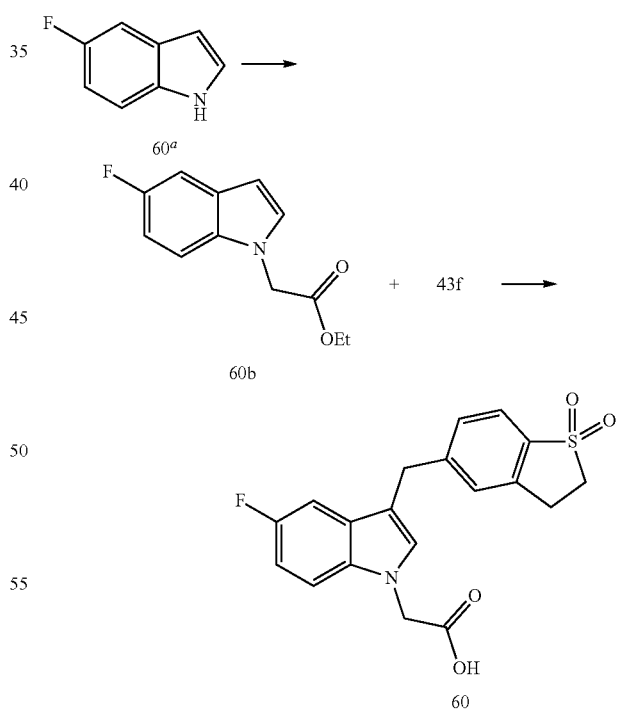

60

Step I

Compound 60b (1.50 g) was synthesized from Compound 60a according to the synthesis method of Compound 6a in Example 6. $^1$H NMR (400 MHz, CDCl$_3$) δ 7.31-7.29 (m, 1H), 7.18-7.15 (m, 2H), 6.99-6.98 (m, 1H), 6.54-6.54 (m, 1H), 4.84 (s, 2H), 4.29-4.16 (m, 2H), 1.30-1.23 (m, 3H).

Step II

Compound 60 (15 mg) was synthesized from Compound 60b and Compound 43f according to the synthesis method in Example 1. $^1$H NMR (400 MHz, CD$_3$OD) δ 7.62-7.60 (m, 1H), 7.47-7.46 (m, 1H), 7.39 (s, 1H), 7.27-7.26 (m, 1H), 7.12 (s, 1H), 7.07-7.05 (m, 1H), 6.96-6.93 (m, 1H), 4.94 (s, 2H), 4.16 (s, 2H), 3.52-3.49 (m, 2H), 3.34-3.33 (m, 2H). MS-ESI calculated value [M+H]$^+$ 374, measured value 374.

Example 61

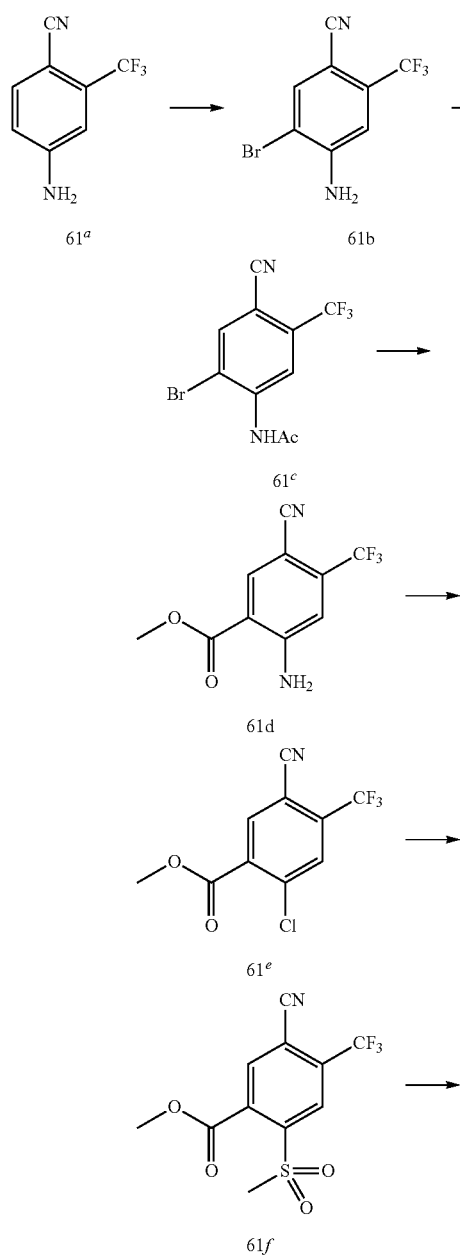

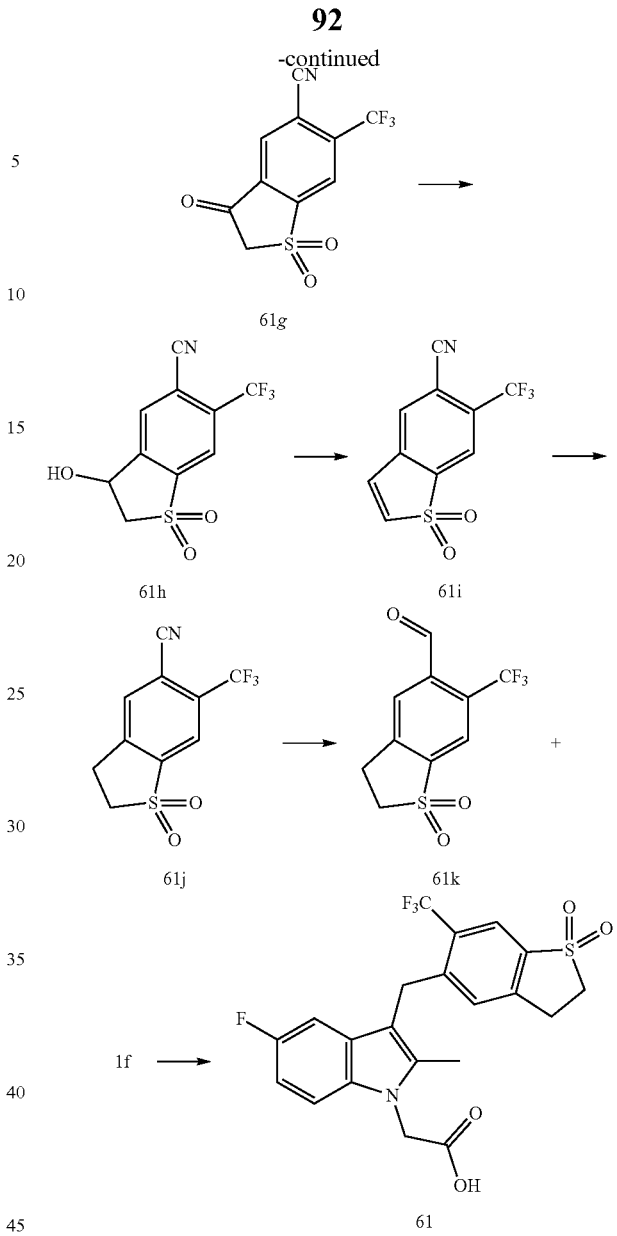

Step I

At 0° C., liquid bromine (21.68 g, 135.66 mmol) was slowly added dropwise to a solution of Compound 61a (25.00 g, 134.31 mmol) in methanol (200 mL). After the resulting reaction mixture was further stirred for 0.5 hr, a saturated solution of sodium thiosulfate (200 mL) was added to the reaction system at 0° C. to quench the reaction. Then, the resulting mixture was diluted with water (1000 mL), and filtered. The resulting solid was washed with water (200 mL×3), and then dried under reduced pressure, to give Compound 61b (34.30 g). $^1$H NMR (400 MHz, DMSO-d$_6$) δ 8.14 (s, 1H), 7.20 (s, 1H), 6.90 (brs, 2H).

Step II

At 0° C., diisopropylethylamine (2.54 g, 19.62 mmol) and trifluoroacetic anhydride (3.49 g 16.60 mmol) were added to a solution of Compound 61b (4.00 g 15.09 mmol) in 50 mL of dichloromethane. After the resulting reaction mixture was stirred for 10 hr at 25° C., a saturated solution of sodium chloride (100 mL) was added to the reaction system at 0° C. to quench the reaction. The resulting mixture was diluted with 100 mL of a saturated solution of sodium chloride, and extracted with ethyl acetate (100 mL×3). The organic phases were combined, washed with a saturated solution of sodium chloride (100 mL×3), dried over anhydrous sodium sulfate, filtered, and concentrated under reduced pressure to give a residue. The residue was separated and purified by column chromatography (petroleum ether/ethyl acetate=100-0%), to give Compound 61c (5.20 g). $^1$H NMR (400 MHz, DMSO-$d_6$) δ 11.78 (brs, 1H), 8.72 (s, 1H), 8.56 (s, 1H).

Step III

Compound 61d (2.87 g) was synthesized from Compound 61c according to the synthesis method of Compound 46c in Example 46.

Step IV

At 0° C., a solution of sodium nitrite (1.21 g, 17.51 mmol) in 20 mL of water was slowly added dropwise to a solution of Compound 61d (2.85 g, 11.67 mmol) in concentrated hydrochloric acid (42.89 mL, 12 N) and 50 mL of acetic acid. After the resulting reaction mixture was stirred for 1 hr, a suspension of cuprous chloride (3.47 g, 35.01 mmol) in concentrated hydrochloric acid (42.89 mL, 12 N) was added to the reaction system, and the resulting mixture was stirred for 1 hr. The reaction system was dispersed in 200 mL of a saturated solution of sodium chloride and 250 mL of ethyl acetate. The organic phase was separated, washed successively with a saturated solution of sodium chloride (100 mL×5) and a saturated solution of sodium bicarbonate (100 mL×3), dried over anhydrous sodium sulfate, filtered, and concentrated under reduced pressure to give a residue. The residue was separated and purified by silica gel column chromatography (petroleum ether/ethyl acetate=100-0%), to give Compound 61e (2.60 g). $^1$H NMR (400 MHz, DMSO-$d_6$) δ 8.59 (s, 1H), 8.32 (s, 1H), 3.93 (s, 3H).

Step V

Sodium methanesulfinate (3.02 g, 29.58 mmol) was added to a solution of Compound 61e (2.60 g, 9.86 mmol) in N,N-dimethylformamide (30 mL). After the resulting reaction mixture was stirred for 1 hr at 50° C., water (100 mL) was added to the reaction system to quench the reaction, and the system was filtered. The resulting solid was washed with water, and dissolved in ethyl acetate (100 mL). The resulting mixture was dried over anhydrous sodium sulfate, filtered, and concentrated under reduced pressure, to give a residue. The residue was separated and purified by silica gel column chromatography (petroleum ether/ethyl acetate=100-0%), to give Compound 61f (2.50 g). $^1$H NMR (400 MHz, DMSO-$d_6$) δ 8.68 (s, 1H), 8.42 (s, 1H), 3.93 (s, 3H), 3.50 (s, 3H).

Step VI

Compound 61g (1.45 g) was synthesized from Compound 61f according to the synthesis method of Compound 1e in Example 1. $^1$H NMR (400 MHz, DMSO-$d_6$) δ 8.99 (s, 1H), 8.87 (s, 1H), 4.76 (s, 2H).

Step VII

At 0° C., sodium borohydride (219 mg, 5.80 mmol) was added in batch to a solution of Compound 61g (1.45 g, 5.27 mmol) in methanol (30 mL). After the resulting reaction mixture was further stirred for 0.5 hr, a saturated solution of ammonium chloride (100 mL) was added to the reaction system at 0° C., and the resulting system was extracted with ethyl acetate (100 mL×3). The organic phases were combined, washed with a saturated solution of sodium chloride (100 mL×3), dried over anhydrous sodium sulfate, and concentrated under reduced pressure to give a residue. The residue was separated and purified by column chromatography (petroleum ether/ethyl acetate=100-0%) to give Compound 61h (1.20 g). $^1$H NMR (400 MHz, DMSO-$d_6$) δ 8.57 (s, 1H), 8.50 (s, 1H), 6.68-6.66 (d, J=6.0 Hz, 1H), 5.54-5.50 (m, 1H), 4.20-4.15 (m, 1H), 4.20-4.15 (m, 1H).

Step VIII

At 0° C., methanesulfonyl chloride (595 mg, 5.20 mmol) and triethylamine (876 mg, 8.66 mmol) were added to a solution of Compound 61h (1.20 g, 4.33 mmol) in dichloromethane (20 mL). After the resulting reaction mixture was stirred for 1 hr at 25° C., a saturated solution of sodium chloride (100 mL) was added to the reaction system to quench the reaction, and the resulting system was diluted with ethyl acetate (200 mL). The organic phase was separated, washed with a saturated solution of sodium chloride (50 mL×3), dried over anhydrous sodium sulfate, filtered, and concentrated under reduced pressure, to give a residue. The residue was separated and purified by column chromatography (petroleum ether/ethyl acetate=100-0%), to give Compound 61i (1.10 g).

Step IX

Compound 61j (900 mg) was synthesized from Compound 61i according to the synthesis method of Compound 43d in Example 43. $^1$H NMR (400 MHz, DMSO-$d_6$) δ 8.50 (s, 1H), 8.47 (s, 1H), 3.79-3.76 (m, 2H), 3.52-3.49 (m, 2H).

Step X

Under the protection of nitrogen and at −78° C., DIBAL-H (1.15 mL, 1.15 mmol, 1M) was slowly added dropwise to a solution of Compound 61j (200 mg, 0.77 mmol) in 5 mL of dichloromethane. After the resulting reaction mixture was stirred for 1 hr at −78° C., a saturated solution of ammonium chloride (50 mL) was added to the reaction system to quench the reaction, and then the resulting system was extracted with ethyl acetate (50 mL×3). The organic phases were combined, washed with a saturated solution of sodium chloride (50 mL×3), dried over anhydrous sodium sulfate, filtered, and concentrated under reduced pressure to give a residue. The residue was separated and purified by column chromatography (petroleum ether/ethyl acetate=100-0%), to give Compound 61k (150 mg). $^1$H NMR (400 MHz, DMSO-$d_6$) δ 10.31-10.30 (d, J=2.0 Hz, 1H), 8.33 (s, 1H), 8.25 (s, 1H), 3.77-3.74 (m, 2H), 3.55-3.52 (m, 2H).

Step XI

Compound 61 (26 mg) was synthesized from Compound 61k and Compound 1f according to the synthesis method in Example 1. $^1$H NMR (400 MHz, CD$_3$OD) δ 8.03 (s, 1H), 7.30-7.27 (m, 1H), 7.13 (s, 1H), 6.87-6.80 (m, 2H), 4.98 (s, 2H), 4.31 (s, 2H), 3.52-3.48 (m, 2H), 3.24-3.21 (m, 2H), 2.31 (s, 3H). MS-ESI calculated value [M+H]$^+$ 456, measured value 456.

Example 62

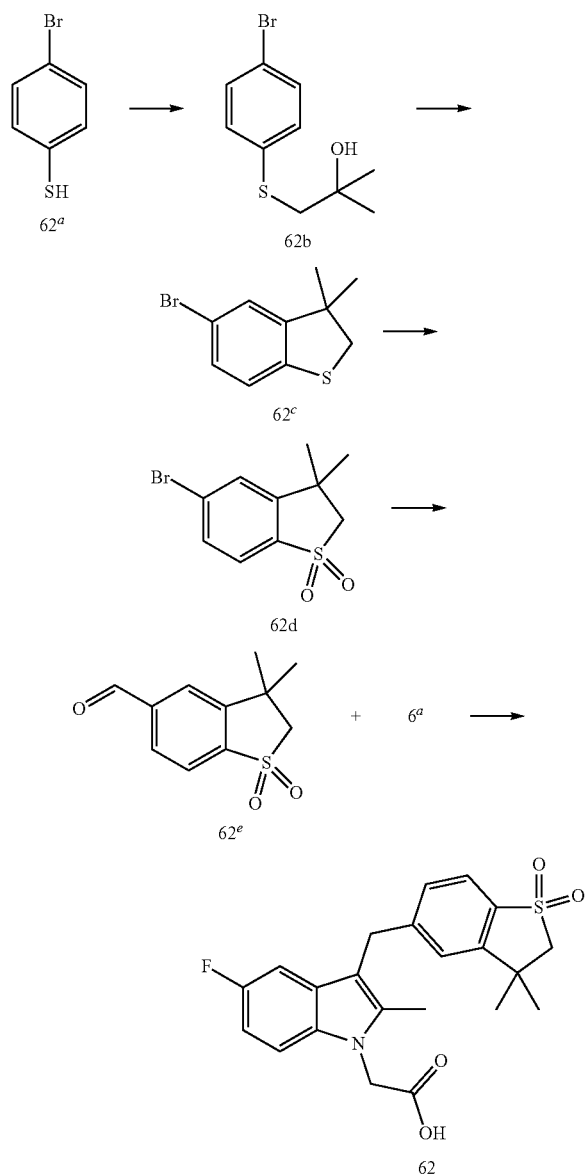

Isobutylene oxide (4.20 g, 58.18 mmol) and potassium carbonate (10.96 g, 79.34 mmol) were added to a solution of Compound 62a (10.00 g, 52.89 mmol) in 100 mL of N,N-dimethylformamide. The resulting reaction mixture was stirred for 0.5 hr at 20° C., a saturated solution of sodium chloride (500 mL) was added to the reaction system to quench the reaction, and then the resulting system was extracted with ethyl acetate (300 mL×3). The organic phases were combined, washed with a saturated solution of sodium chloride (100 mL×3), dried over anhydrous sodium sulfate, filtered, and concentrated under reduced pressure to give a residue. The residue was separated and purified by column chromatography (petroleum ether/ethyl acetate=100-0%), to give Compound 62b (8.50 g). $^1$H NMR (400 MHz, CDCl$_3$) δ 7.33-7.31 (d, =−8.8 Hz, 2H), 7.21-7.19 (d, =−8.4 Hz, 2H), 3.02 (s, 2H), 1.24 (s, 6H).

Step II

At −10° C., a solution of Compound 62b (8.00 g, 30.64 mmol) in 160 mL of carbon disulfide was added to a suspension of aluminium trichloride (14.32 g, 107.28 mmol) in carbon disulfide (160 mL). The resulting reaction mixture was stirred for 0.5 hr at 75° C., and then cooled to 0° C. 1 N diluted hydrochloric acid (200 mL) was added to the reaction system, and the resulting mixture was then extracted with ethyl acetate (150 mL×3). The organic phases were combined, washed with a saturated solution of sodium chloride (100 mL×3), dried over anhydrous sodium sulfate, filtered, and concentrated under reduced pressure, to give a residue. The residue was separated and purified by column chromatography (petroleum ether/ethyl acetate=100-0%) to give Compound 62c (2.20 g). $^1$H NMR (400 MHz, CDCl$_3$) δ 7.24-7.22 (m, 1H), 7.15 (s, 1H), 7.06-7.03 (d, =−8.4 Hz, 1H), 3.19 (s, 2H), 1.37 (s, 6H).

Step III

Compound 62d (900 mg) was synthesized from Compound 62c according to the synthesis method of Compound 1d in Example 1. $^1$H NMR (400 MHz, CDCl$_3$) δ 7.64-7.56 (m, 3H), 3.36 (s, 2H), 1.55 (s, 6H).

Step IV

Compound 62e (340 mg) was synthesized from Compound 62d according to the synthesis method in Example 47. $^1$H NMR (400 MHz, CDCl$_3$) δ 10.12 (s, 1H), 8.00-7.99 (m, 2H), 7.90-7.88 (d, J=8.4 Hz, 1H), 3.43 (s, 2H), 1.61 (s, 6H).

Step V

Compound 62 (40 mg) was synthesized from Compound 62e and Compound 6a according to the synthesis method in Example 6. $^1$H NMR (400 MHz, CD$_3$OD) δ 7.51-7.47 (m, 2H), 7.35-7.33 (d, J=8.0 Hz, 1H), 7.21-7.20 (m, 1H), 6.98-6.97 (m, 1H), 6.95-6.82 (m, 1H), 4.81 (s, 2H), 4.18 (s, 2H), 3.38 (s, 2H), 2.35 (s, 3H), 1.47 (s, 6H). MS-ESI calculated value [M+H]$^+$ 416, measured value 416.

Example 63

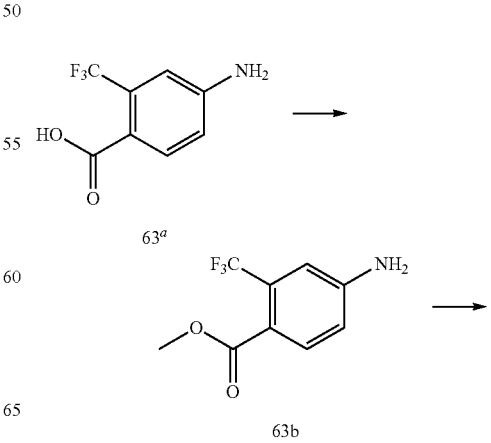

-continued

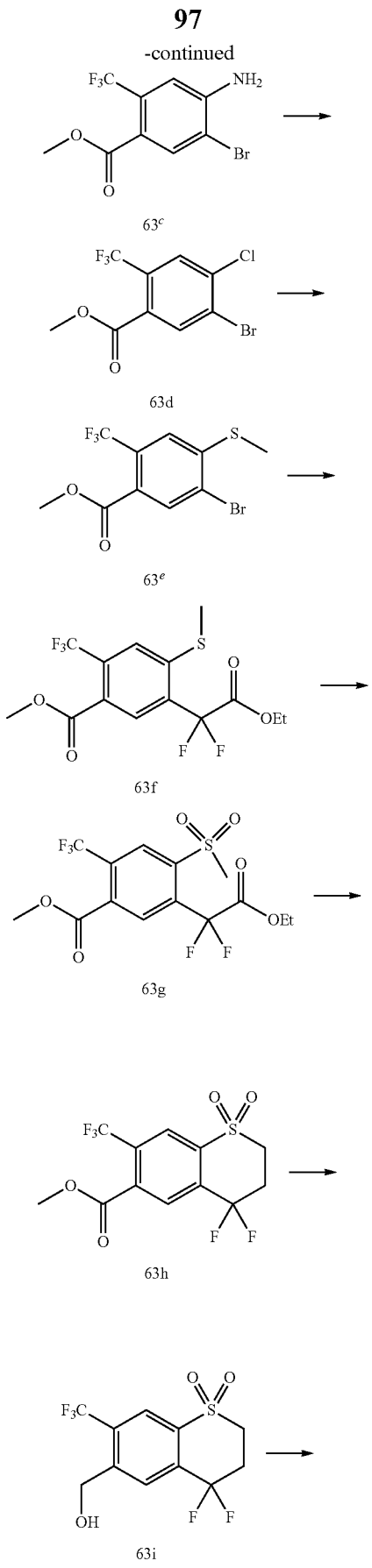

63c

63d

63e

63f

63g

63h

63i

-continued

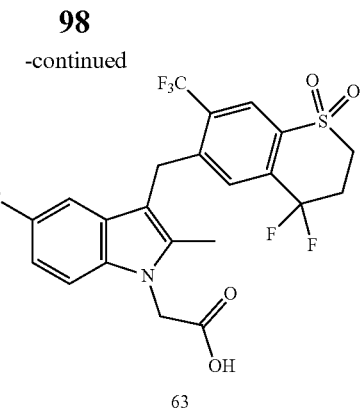

63

Step I

At 0° C., trimethylsilyl diazomethane (55.57 mL, 2 M, 111.15 mmol) was slowly added dropwise to a mixed solution of Compound 63a (19.00 g, 92.62 mmol) in 150 mL of methanol and 150 mL of dichloromethane. The resulting reaction mixture was stirred for 1 hr at 0° C., and 10 mL of water was added to quench the reaction. The resulting mixture was directly concentrated under reduced pressure, to give Compound 63b (20.30 g). $^1$H NMR (400 MHz, CDCl$_3$) δ 7.78-7.76 (d, J=8.8 Hz, 1H), 6.99-6.98 (d, J=2.0 Hz, 1H), 6.78-6.75 (dd, J=8.4 Hz, J=2.4 Hz, 1H), 4.21 (s, 2H), 3.88 (s, 3H).

Step II

At 0° C., a solution of liquid bromine (15.54 g, 97.26 mmol) in 200 mL of methanol was slowly added dropwise to a solution of Compound 63b (20.30 g, 92.63 mmol) in 200 mL of methanol. The resulting reaction mixture was stirred for 1 hr at 0° C., and concentrated under reduced pressure to give a residue. The residue was diluted with 200 mL of ethyl acetate and 200 mL of a saturated solution of sodium bicarbonate, and then the resulting mixture was extracted with ethyl acetate (100 mL×3). The organic phases were combined, dried over anhydrous sodium sulfate, filtered, and concentrated under reduced pressure, to give Compound 63c (27.00 g). MS-ESI calculated value [M+H]$^+$ 298, measured value 298.

Step III

Compound 63d (3.40 g) was synthesized from Compound 63c according to the synthesis method of Compound 61e in Example 61.

Step IV

At 0° C., sodium thiomethoxide (1.84 g, 26.21 mmol) was added to a solution of Compound 63d (6.40 g, 20.16 mmol) in 70 mL of N,N-dimethylformamide. The resulting reaction mixture was stirred for 1 hr at 0° C., and 1 N diluted hydrochloric acid (20 mL) was added to the reaction mixture. The resulting mixture was diluted with a saturated solution of sodium chloride (50 mL), and extracted with ethyl acetate (50 mL×3). The organic phases were combined, washed with a saturated solution of sodium chloride (50 mL×3), dried over anhydrous sodium sulfate, filtered, and concentrated under reduced pressure, to give a residue.

99

The residue was separated and purified by column chromatography (petroleum ether/ethyl acetate=100-0%), to give Compound 63e (5.80 g).

Step V

Copper powder (8.96 g, 140.98 mmol) and ethyl bromodifluoroacetate (14.31 g, 70.49 mmol) were added to a solution of Compound 63e (5.80 g, 17.62 mmol) in 100 mL of dimethyl sulfoxide under the protection of nitrogen. The resulting reaction mixture was stirred for 5 hr at 80° C., and then cooled to room temperature. The reaction mixture was diluted with ethyl acetate (100 mL), filtered, and washed with ethyl acetate (50 mL×3). Then, the filtrate was diluted with a saturated solution of sodium chloride (100 mL), and extracted with ethyl acetate (50 mL×3). The organic phases were combined, washed with a saturated solution of sodium chloride (50 mL×3), dried over anhydrous sodium sulfate, filtered, and concentrated under reduced pressure, to give a residue. The residue was separated and purified by column chromatography (petroleum ether/ethyl acetate=100-0%), to give Compound 63f (5.60 g).

Step VI

Compound 63g (4.60 g) was synthesized from Compound 63f according to the synthesis method of Compound 1d in Example 1. $^1$H NMR (400 MHz, CDCl$_3$) δ 8.52 (s, 1H), 8.30 (s, 1H), 4.36 (q, J=7.2 Hz, 2H), 4.03 (s, 3H), 3.22 (s, 3H).

Step VII

Compound 63h (540 mg) was synthesized from Compound 63g according to the synthesis method of Compound 61j in Example 61. $^1$H NMR (400 MHz, CDCl$_3$) δ 8.32 (s, 1H), 8.22 (s, 1H), 4.02 (s, 3H), 4.01-3.66 (m, 2H), 3.15-3.09 (m, 2H).

Step VIII

At 0° C., lithium aluminum hydride (46 mg, 1.22 mmol) was added to a solution of Compound 63h (420 mg, 1.22 mmol) in 5 mL of tetrahydrofuran. The resulting reaction mixture was stirred for 0.5 hr. Water (50 μL), 15% sodium hydroxide solution (50 μL), and water (150 μL) were added successively to the reaction system at 0° C. The resulting mixture was further stirred for 0.5 hr, filtered, and concentrated under reduced pressure, to give a residue. The residue was separated and purified by column chromatography (petroleum ether/ethyl acetate=100-0%), to give Compound 63i (100 mg).

Step IX

Compound 63 (30 mg) was synthesized from Compound 63i according to the synthesis method in Example 47. $^1$H NMR (400 MHz, DMSO-d$_6$) δ 8.14 (s, 1H), 7.42-7.39 (m, 2H), 6.96-6.89 (m, 2H), 4.87 (s, 2H), 4.32 (s, 2H), 3.91-3.88 (m, 2H), 3.03-2.96 (m, 2H), 2.25 (s, 3H). MS-ESI calculated value [M+H]$^+$ 506, measured value 506.

100

Example 64

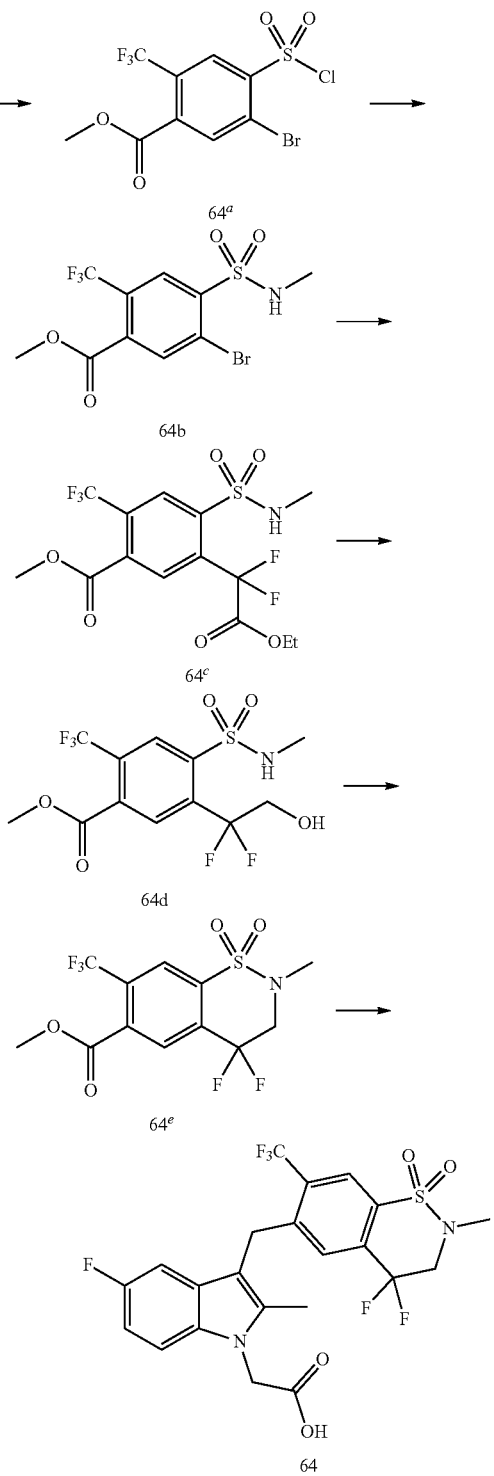

Step I

Concentrated hydrochloric acid (100 mL, 12 N) was slowly added dropwise to a solution of Compound 63c in acetic acid (100 mL), and the resulting mixture was stirred for 0.5 hr. A solution of sodium nitrite (8.80 g, 127.49 mmol) in 5 mL of water was slowly added dropwise to the reaction system at 0° C. After completion of the dropwise addition, the resulting reaction mixture was further stirred for 0.5 hr. The reaction mixture was added dropwise to a mixture of cuprous chloride (1.89 g, 19.12 mmol) and liquid sulfur dioxide (200 g, 3.12 mol) at 0° C., and then the resulting reaction mixture was further stirred for 0.5 hr. The reaction mixture was diluted with 500 mL of water, and extracted with ethyl acetate (200 mL×4). The organic phases were combined, washed with a saturated solution of sodium chloride (150 mL×4), dried over anhydrous sodium sulfate, filtered, and concentrated under reduced pressure, to give Compound 64a (24.32 g).

Step II

A solution of Compound 64a (24.32 g, 63.74 mmol) in acetonitrile (200 mL) was slowly added dropwise to a solution of methylamine (319.98 mmol, 2M) in 160 mL of tetrahydrofuran at 0° C. The resulting reaction mixture was stirred for 1 hr, and concentrated under reduced pressure, to give a residue. The residue was slurried (in 50 mL of a mixed solvent of ethyl acetate/petroleum ether=10/1) to give Compound 64b (15.00 g). $^1$H NMR (400 MHz, CDCl$_3$) δ 8.48 (s, 1H), 8.14 (s, 1H), 5.10-5.09 (d, J=5.2 Hz, 1H), 3.99 (s, 3H), 2.71-2.70 (d, J=5.2 Hz, 3H).

Step III

Compound 64c (8.00 g) was synthesized from Compound 64b according to the synthesis method of Compound 63f in Example 63.

Step IV

Compound 64d (630 mg) was synthesized from Compound 64c according to the synthesis method of Compound 63i in Example 63.

Step V

Compound 64e (15 mg) was synthesized from Compound 64d according to the synthesis method of Compound 47f in Example 47. $^1$H NMR (400 MHz, CD$_3$OD) δ 8.14 (s, 1H), 7.45 (s, 1H), 7.31-7.29 (m, 1H), 6.85-6.83 (m, 2H), 4.99 (s, 2H), 4.36 (s, 2H), 4.23 (t, J=-12.4 Hz, 2H), 2.97 (s, 3H), 2.32 (s, 3H). MS-ESI calculated value [M+H]$^+$ 521, measured value 521.

Example 65

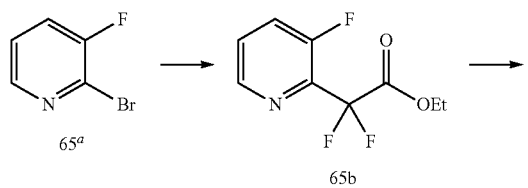

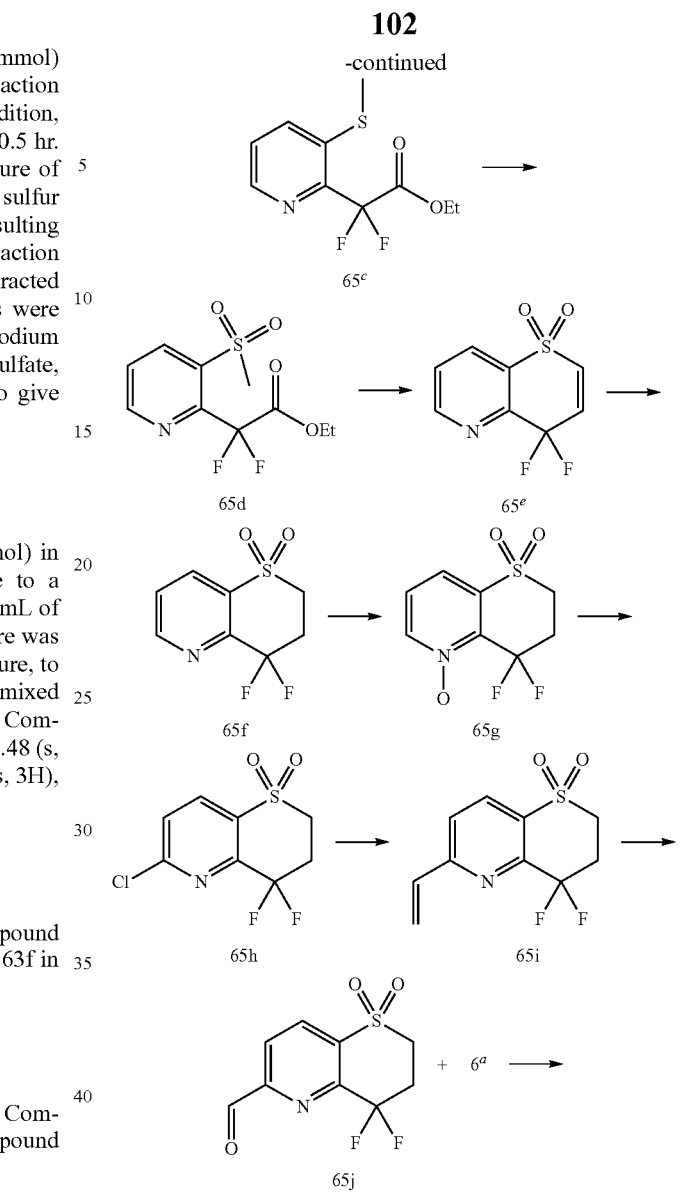

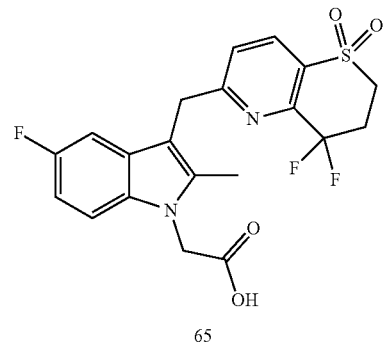 [SMILES: Cc1c(Cc2ccc3c(n2)C(F)(F)CCS3(=O)=O)c2cc(F)ccc2n1CC(=O)O]

Step I

Compound 65b (19.00 g) was synthesized from Compound 65a according to the synthesis method of Compound 63f in Example 63.

Step II

Compound 65c (17.00 g) was synthesized from Compound 65b according to the synthesis method of Compound 63e in Example 63.

Step III

Compound 65d (15.00 g) was synthesized from Compound 65c according to the synthesis method of Compound 1d in Example 1.

Step IV

Compound 65e (5.40 g) was synthesized from Compound 65d according to the synthesis method of Compound 61i in Example 61.

Step V

At 0° C., sodium borohydride (2.00 g, 52.86 mmol) was added in batch to a mixed solution of Compound 65e (5.80 g, 26.70 mmol) in 40 mL of tetrahydrofuran and 40 mL of methanol. The resulting reaction mixture was further stirred for 1 hr, water (1 mL) was slowly added to the reaction system at 0° C., and then the reaction system was concentrated under reduced pressure, to give a residue. The residue was separated and purified by column chromatography (petroleum ether/ethyl acetate=100-0%), to give Compound 65f (4.80 g). $^1$H NMR (400 MHz, DMSO-$d_6$) δ 9.04-9.03 (m, 1H), 8.47-8.45 (d, =−8.0 Hz, 1H), 7.92-7.89 (m, 1H), 3.98-3.95 (m, 2H), 3.12-3.02 (m, 2H).

Step VI

At 0° C., urea hydrogen peroxide (21.46 g, 228.09 mmol) and trifluoroacetic anhydride (47.91 g, 228.09 mmol) were added to a solution of Compound 65f (5.00 g, 22.81 mmol) in 35 mL of dichloromethane and 35 mL of acetonitrile. The resulting reaction mixture was stirred for 5 hr at 50° C., and then cooled to 0° C. A saturated solution of sodium chloride (200 mL) was added to the reaction system to quench the reaction, and then the resulting mixture was extracted with ethyl acetate (100 mL×3). The organic phases were combined, washed with a saturated solution of sodium chloride (50 mL×3), dried over anhydrous sodium sulfate, filtered, and concentrated under reduced pressure, to give a residue. The residue was separated and purified by column chromatography (petroleum ether/ethyl acetate=100-0%), to give Compound 65g (3.50 g). $^1$H NMR (400 MHz, DMSO-$d_6$) δ 8.59-8.57 (m, 1H), 7.82-7.77 (m, 2H), 3.97-3.94 (m, 2H), 3.08-2.97 (m, 2H).

Step VII

Compound 65g (3.45 g, 14.67 mmol) was dissolved in phosphorus oxychloride (70 mL). The resulting reaction mixture was stirred for 3 hr at 70° C., and then cooled to room temperature. The reaction mixture was slowly added dropwise to water (200 mL), and then the resulting mixture was extracted with ethyl acetate (150 mL×3). The organic phases were combined, washed with a saturated solution of sodium chloride (100 mL×1), dried over anhydrous sodium sulfate, filtered, and concentrated under reduced pressure, to give a residue. The residue was separated and purified by column chromatography (petroleum ether/ethyl acetate=100-0%) to give Compound 65h (1.60 g).

Step VIII

Under the protection of nitrogen, [1,1'-bis(diphenylphosphino)ferrocene]dichloropalladium (65 mg, 0.89 mmol), potassium carbonate (245 mg, 1.77 mmol), and potassium ethenyltrifluoroborate (119 mg, 0.89 mmol) were added to a solution of Compound 65h (150 mg, 0.59 mmol) in N,N-dimethylformamide (5 mL). The resulting reaction mixture was stirred for 3 hr at 80° C., and then cooled to room temperature. The reaction system was diluted with ethyl acetate (80 mL), and filtered. The filtrate was washed with a saturated solution of sodium chloride (20 mL×2), dried over anhydrous sodium sulfate, filtered, and concentrated under reduced pressure, to give a residue. The residue was separated and purified by column chromatography (petroleum ether/ethyl acetate=100-0%), to give Compound 65i (320 mg). $^1$H NMR (400 MHz, CDCl$_3$) δ 8.23-8.21 (d, J=8.4 Hz, 1H), 7.68-7.66 (d, J=8.4 Hz, 1H), 6.96-6.89 (m, 1H), 6.49-6.45 (d, J=8.4 Hz, 1H), 5.79-5.76 (d, J=11.2 Hz, 1H), 3.65-3.62 (m, 2H), 3.13-3.06 (m, 2H). MS-ESI calculated value [M+H]$^+$ 246, measured value 246.

Step IX

At 0° C., osmium tetroxide (30 mg, 0.12 mmol) and sodium periodate (1.01 g, 4.73 mmol) were successively added to a solution of Compound 65i (290 mg, 1.18 mmol) in tetrahydrofuran (3 mL) and water (3 mL). The resulting reaction system was stirred for 1 hr, and a saturated solution of sodium thiosulfate (20 mL) was added to the reaction system to quench the reaction. The reaction mixture was extracted with ethyl acetate (20 mL×3). The organic phases were combined, washed with a saturated solution of sodium chloride (20 mL×3), dried over anhydrous sodium sulfate, filtered, and concentrated under reduced pressure, to give Compound 65j (80 mg).

Step X

Compound 65 (65 mg) was synthesized from Compound 65j and Compound 6a according to the synthesis method in Example 6. $^1$H NMR (400 MHz, DMSO-$d_6$) δ 8.27-8.24 (d, J=8.4 Hz, 1H), 7.56-7.53 (d, J=8.8 Hz, 1H), 7.26-7.21 (m, 2H), 6.84-6.80 (m, 1H), 4.58 (s, 2H), 4.30 (s, 2H), 3.91-3.88 (m, 2H), 3.05-3.02 (m, 2H), 2.34 (s, 3H). MS-ESI calculated value [M+H]$^+$ 439, measured value 439.

Example 66

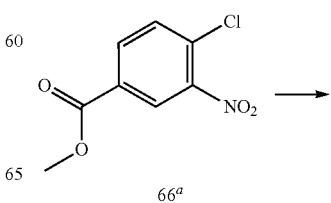

66$^a$

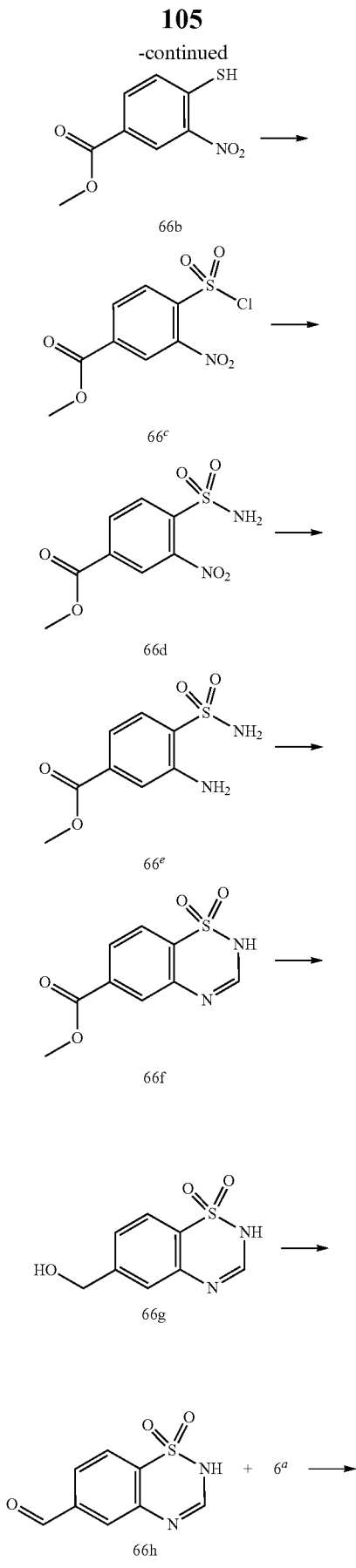

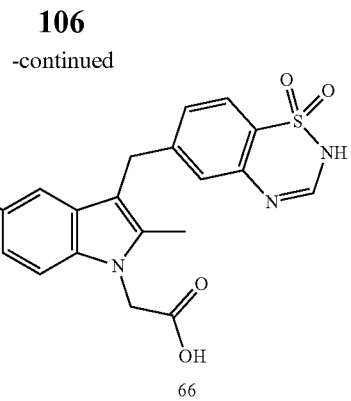

66

Step I

Sodium sulfide (10.86 g, 139.15 mmol) was added to a solution of Compound 66a (25.00 g, 115.96 mmol) in dimethylformamide (200 mL). The resulting reaction mixture was stirred for 16 hr at 20° C. After completion of the reaction, the reaction mixture was poured into water (500 mL), and adjusted with 1 N aqueous solution of hydrochloric acid to pH 5. Solids were precipitated. The solids were obtained by filtration, and then slurried in a mixed solvent of petroleum ether and ethyl acetate (200 mL, v/v=3/1), to give Compound 66b (16.70 g). $^1$H NMR (400 MHz, CDCl$_3$) δ 8.89 (d, J=1.6 Hz, 1H), 8.05 (dd, J=1.6, J=8.4 Hz, 1H), 7.52 (d, J=8.4 Hz, 1H), 4.21 (s, 1H), 3.96 (s, 3H).

Step II

Compound 66b (16.7 g, 78.33 mmol) was added in batch to a solution of chlorosuccinimide (52.29 g, 391.63 mmol) and hydrochloric acid (2 M, 83.42 mL) in acetonitrile (500 mL), and the reaction system was placed in an ice bath to maintain the temperature of the reaction system was less than 20° C. during the addition process. After completion of the addition, the resulting reaction mixture was warmed to 20° C., and stirred for 16 hr. After completion of the reaction, the reaction mixture was diluted with water (200 mL), evaporated to remove most of acetonitrile, and extracted with ethyl acetate (200 mL×2). The organic phases were combined, washed successively with a saturated solution of sodium bicarbonate (500 mL×2) and saturated brine (500 mL×2), dried over anhydrous sodium sulfate, filtered, and concentrated, to give Compound 66c (25.00 g). $^1$H NMR (400 MHz, CDCl$_3$) δ 8.49-8.43 (m, 2H), 8.33 (m, 1H), 4.03 (m, 3H).

Step III

A solution of ammonia in acetonitrile (6 M, 44.70 mL) was added to a solution of Compound 66c (15 g, 53.64 mmol) in acetonitrile (250 mL). The resulting reaction mixture was stirred for 1 hr at 25° C. After completion of the reaction, the reaction mixture was diluted with water (500 mL), evaporated to remove most of acetonitrile, and extracted with ethyl acetate (300 mL×2). The organic phases were combined, washed with saturated brine (500 mL×2), dried over anhydrous sodium sulfate, filtered, and concentrated, to give Compound 66d (9.60 g). $^1$H NMR (400 MHz, DMSO-d$_6$) δ 8.46-8.34 (m, 2H), 8.20 (d, J=8.4 Hz, 1H), 8.06 (s, 2H), 3.92 (s, 3H).

Step IV

A solution of Compound 66d (9.60 g, 36.89 mmol) and raney nickel (316 mg) in methanol (100 mL) and tetrahydrofuran (100 mL) was stirred for 5 hr at 20° C. under a hydrogen (50 PSI) atmosphere. After completion of the reaction, the reaction mixture was filtered, and concentrated, to give Compound 66e (8.45 g). $^1$H NMR (400 MHz, DMSO-$d_6$) δ 7.64 (d, J=8.4 Hz, 1H), 7.45 (d, J=1.6 Hz, 1H), 7.42 (s, 2H), 7.13 (m, 1H), 6.09 (s, 2H), 3.83 (s, 3H).

Step V

A solution of Compound 66e (1.00 g, 4.34 mmol) in formic acid (50 mL) was heated to 100° C., and stirred for 0.5 hr. After completion of the reaction, the reaction mixture was concentrated to dryness. The residue was slurried in a mixed solvent of petroleum ether and ethyl acetate (20 mL, v/v=5/1), and filtered, to give Compound 66f (800 mg). $^1$H NMR (400 MHz, DMSO-$d_6$) δ 8.03 (s, 1H), 7.97-7.89 (m, 3H), 3.91 (s, 3H). MS-ESI calculated value [M+H]$^+$ 241, measured value 241.

Step VI

Compound 66g (0.35 g) was synthesized from Compound 66f according to the synthesis method of Compound 63i in Example 63. MS-ESI calculated value [M+H]$^+$ 213, measured value 213.

Step VII

Compound 66h (0.08 g) was synthesized from Compound 66g according to the synthesis method of Compound 43f in Example 43.

Step VIII

Compound 66 (61 mg) was synthesized from Compound 66h and Compound 6a according to the method in Example 1. $^1$H NMR (400 MHz, DMSO-$d_6$) δ 7.88 (s, 1H), 7.70 (d, J=8.4 Hz, 1H), 7.37 (m, 1H), 7.33 (d, J=9.2 Hz, 1H), 7.16 (m, 1H), 7.09 (s, 1H), 6.92-6.84 (m, 1H), 4.96 (s, 2H), 4.11 (s, 2H), 2.31 (s, 3H). MS-ESI calculated value [M+H]$^+$ 402, measured value 402.

Example 67

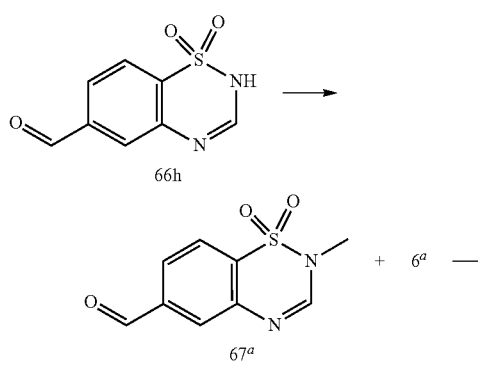

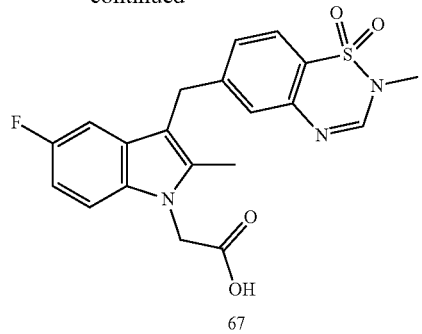

Step I

Cesium carbonate (248 mg, 0.76 mmol) and iodomethane (81 mg, 0.57 mmol) were added to a solution of Compound 66h (0.08 g, 0.38 mmol) in dimethylformamide (10 mL). The resulting reaction mixture was stirred for 2 hr at 50° C. After completion of the reaction, the reaction mixture was directly filtered, and the filtrate was concentrated to give Compound 67a (0.09 g).

Step II

Compound 67 (13 mg) was synthesized from Compound 67a and Compound 6a according to the method in Example 1. $^1$H NMR (400 MHz, DMSO-$d_6$) δ 8.03 (s, 1H), 7.74 (d, J=8.0 Hz, 1H), 7.39 (s, 1H), 7.38-7.34 (m, 1H), 7.28 (d, J=8.4 Hz, 1H), 7.22 (m, 1H), 6.87 (m, 1H), 4.97 (s, 2H), 4.17 (s, 2H), 3.57 (s, 3H), 2.34 (s, 3H). MS-ESI calculated value [M+H]$^+$ 416, measured value 416.

Example 68

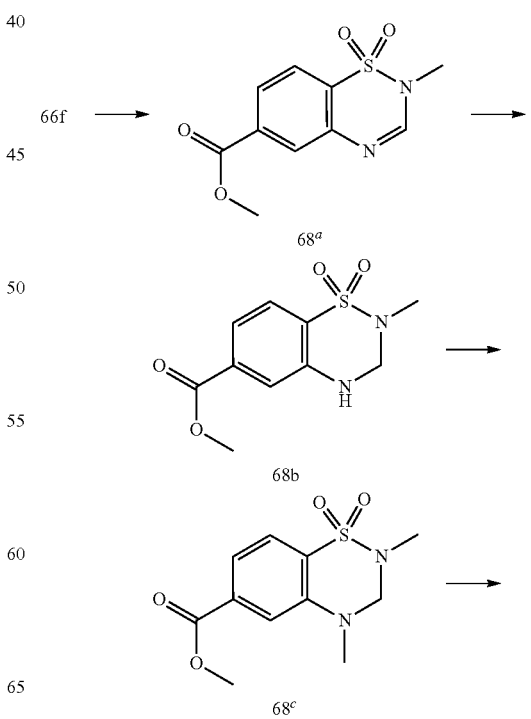

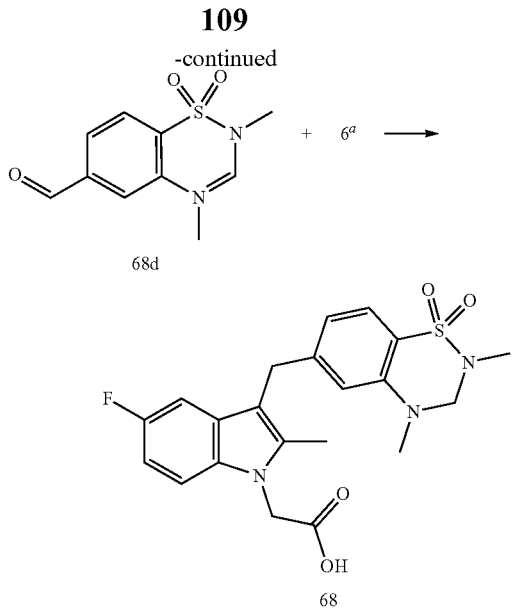

Step I

Cesium carbonate (1.76 g, 5.41 mmol) and iodomethane (461 mg, 3.25 mmol) were added to a solution of Compound 66f (520 mg, 2.16 mmol) in dimethylformamide (15 mL). The resulting reaction mixture was stirred for 2 hr at 50° C. After completion of the reaction, the reaction mixture was poured into water (100 mL), and extracted with ethyl acetate (20 mL×2). The organic phases were combined, washed with saturated brine (50 mL×2), dried over anhydrous sodium sulfate, filtered, concentrated, and then washed with methyl t-butyl ether (5 mL×1), to give Compound 68a (330 mg). MS-ESI calculated value $[M+H]^+$ 255, measured value 255.

Step II

At 0° C., sodium borohydride (34 mg, 0.91 mmol) was added to a solution of Compound 68a (330 mg, 0.91 mmol) in tetrahydrofuran (50 mL). The resulting reaction mixture was warmed to 25° C., and further stirred for 1 hr. After completion of the reaction, water (20 mL) was added to the reaction mixture to quench the reaction, and the resulting mixture was extracted with ethyl acetate (30 mL×2). The organic phases were combined, dried over anhydrous sodium sulfate, filtered, concentrated, and separated and purified by column chromatography (petroleum ether/ethyl acetate=100-0%), to give Compound 68b (214 m). $^1$H NMR (400 MHz, DMSO-$d_6$) δ 8.24-8.22 (m, 1H), 7.68 (d, J=8.4 Hz, 1H), 7.32 (m, 2H), 4.73 (d, J=8.0 Hz, 2H), 3.87 (s, 3H), 3 (s, 3H). MS-ESI calculated value $[M+H]^+$257, measured value 257.

Step III

At 0° C., sodium hydride (33 mg, 0.84 mmol, purity: 60%) was added to a solution of Compound 68b (214 mg, 0.84 mmol) in dimethylformamide (10 mL). The resulting reaction mixture was further stirred for 0.5 hr. Iodomethane (178 mg, 1.25 mmol) was added, and the resulting reaction mixture was stirred for 1 hr at 20° C. After completion of the reaction, the reaction mixture was poured into water (100 mL), and extracted with ethyl acetate (20 mL×2). The organic phases were combined, washed with saturated brine (50 mL×2), dried over anhydrous sodium sulfate, filtered, and concentrated, to give Compound 68c (200 mg). MS-ESI calculated value $[M+H]^+$ 271, measured value 271.

Step IV

Compound 68d (161 mg) was synthesized from Compound 68c according to the synthesis method in Example 43. MS-ESI calculated value $[M+H]^+$ 241, measured value 241.

Step VI

Compound 68 (63 mg) was synthesized from Compound 68d and Compound 6a according to the method in Example 1. $^1$H NMR (400 MHz, DMSO-$d_6$) δ 7.40 (d, J=8.0 Hz, 1H), 7.36 (m, 1H), 7.20 (m, 1H), 6.86 (m, 1H), 6.77 (s, 1H), 6.62 (d, J=8.0 Hz, 1H), 4.97 (s, 2H), 4.82 (s, 2H), 4.01 (s, 2H), 2.93 (s, 3H), 2.63 (s, 3H), 2.33 (s, 3H). MS-ESI calculated value $[M+H]^+$ 432, measured value 432.

Example 69

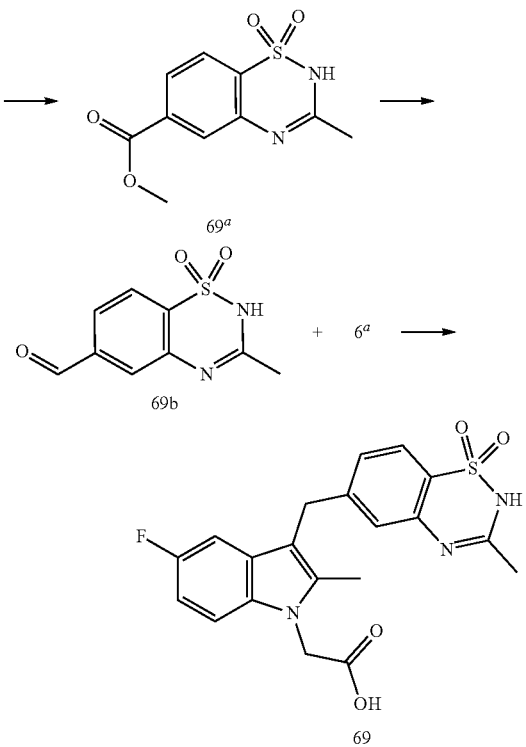

Step I

A solution of Compound 66e (1.20 g, 5.21 mmol) in acetic anhydride (50 mL) was heated to 120° C., and stirred for 2 hr. After completion of the reaction, the reaction mixture was washed with a saturated solution of sodium bicarbonate (200 mL), and extracted with ethyl acetate (50 mL×2). The organic phases were combined, washed with saturated brine (100 mL×2), dried over anhydrous sodium sulfate, filtered, concentrated, and then washed with methyl t-butyl ether (10 mL), to give Compound 69a (370 mg). MS-ESI calculated value [M+H]+ 255, measured value 255.

Step II

Compound 69b (200 mg) was synthesized from Compound 69a according to the synthesis method in Example 66. MS-ESI calculated value [M+H]+ 225, measured value 225.

Step III

Compound 69 (13 mg) was synthesized from Compound 69b and Compound 6a according to the method in Example 1. $^1$H NMR (400 MHz, DMSO-d$_6$) δ 11.87 (brs, 1H), 7.68 (d, J=8.4 Hz, 1H), 7.38 (m, 1H), 7.34 (d, J=8.0 Hz, 1H), 7.16 (m, 1H), 7 (s, 1H), 6.89 (m, 1H), 4.97 (s, 2H), 4.11 (s, 2H), 2.31 (s, 3H), 2.22 (s, 3H). MS-ESI calculated value [M+H]+ 416, measured value 416.

Example 70

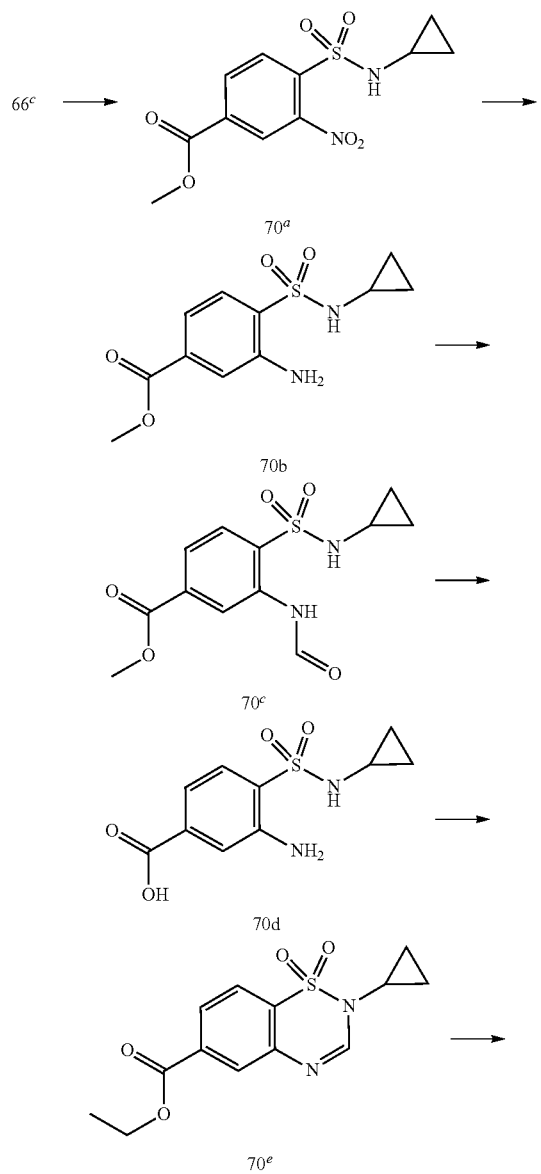

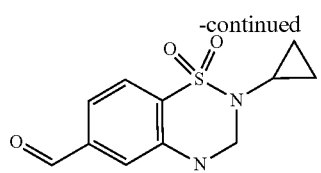

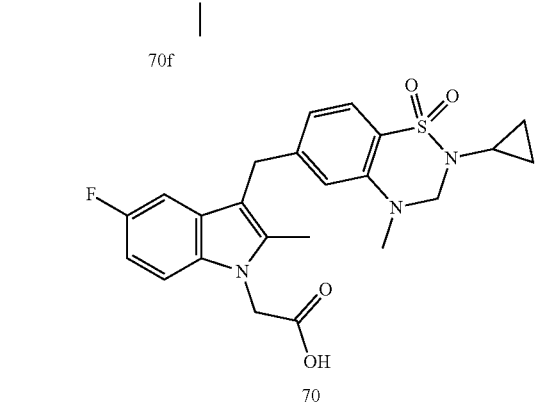

Step I

Cyclopropylamine (2.55 g, 44.70 mmol) was added to a solution of Compound 66c (2.50 g, 8.94 mmol) in acetonitrile (50 mL). The resulting reaction mixture was stirred for 2 hr at 25° C. After completion of the reaction, the reaction mixture was diluted with water (100 mL), evaporated to remove most of acetonitrile, and extracted with ethyl acetate (50 mL×3). The organic phases were combined, washed with saturated brine (250 mL×2), dried over anhydrous sodium sulfate, filtered, and concentrated to give Compound 70a (2.40 g). $^1$H NMR (400 MHz, CDCl$_3$) δ 8.46 (d, J=1.6 Hz, 1H), 8.40-8.35 (m, 1H), 8.31-8.27 (m, 1H), 5.60 (s, 1H), 4.01 (s, 3H), 2.43-2.32 (m, 1H), 0.77-0.68 (m, 4H).

Step II

Compound 70b (1.80 g) was synthesized from Compound 70a according to the method in Example 66. $^1$H NMR (400 MHz, DMSO-d$_6$) δ 8.02 (brs, 1H), 7.63 (d, J=8.4 Hz, 1H), 7.47 (d, J=1.6 Hz, 1H), 7.15 (m, 1H), 6.15 (s, 2H), 3.84 (s, 3H), 2.08 (m, 1H), 0.48-0.41 (m, 2H), 0.40-0.33 (m, 2H). MS-ESI calculated value [M+H]+ 271, measured value 271.

Step III

A solution of Compound 70b (1.80 g, 6.66 mmol) in formic acid (50 mL) was heated to 100° C., and stirred for 12 hr. After completion of the reaction, the reaction mixture was concentrated to dryness, and the residue was separated and purified by silica gel column chromatography (petroleum ether/ethyl acetate=100-0%), to give Compound 70c (1.25 g). $^1$H NMR (400 MHz, DMSO-d$_6$) δ 9.55 (brs, 1H), 8.88 (s, 1H), 8.49 (s, 1H), 8.40 (br s, 1H), 7.99 (d, J=8.4 Hz, 1H), 7.87 (m, 1H), 3.90 (s, 3H), 2.22-2.12 (m, 1H), 0.53-0.46 (m, 2H), 0.39-0.32 (m, 2H). MS-ESI calculated value [M+H]+ 299, measured value 299.

Step IV

A solution of sodium hydroxide (1.07 g, 26.82 mmol) in water (10 mL) was added to a solution of Compound 70c (1.00 g, 3.35 mmol) in methanol (50 mL). The resulting reaction mixture was stirred for 16 hr at 80° C. After completion of the reaction, the reaction mixture was diluted with water (30 mL), evaporated to remove most of methanol, adjusted with diluted hydrochloric acid to pH 5, and extracted with ethyl acetate (100 mL×2). The organic phases were combined, dried over anhydrous sodium sulfate, filtered, and concentrated, to give Compound 70d (850 mg). MS-ESI calculated value [M+H]$^+$ 257, measured value 257.

Step V

A solution of Compound 70d (850 mg, 3.32 mmol) in triethyl orthoformate (40 mL) was heated to 140° C., and stirred for 8 hr. After completion of the reaction, the reaction mixture was concentrated to dryness, and the residue was dissolved in ethyl acetate (100 mL). The resulting mixture was washed with a saturated solution of sodium bicarbonate (100 mL×11). The organic phase was dried over anhydrous sodium sulfate, filtered, and concentrated, to give Compound 70e (950 mg). $^1$H NMR (400 MHz, CDCl$_3$) δ 8.20 (d, J=1.2 Hz, 1H), 8.10 (m, 1H), 7.99 (d, J=8.4 Hz, 1H), 7.67 (s, 1H), 4.42 (m, 2H), 3.20 (m, 1H), 1.42 (m, 3H), 1.20-1.14 (m, 4H). MS-ESI calculated value [M+H]$^+$ 295, measured value 295.

Step VI

Compound 70f (85 mg) was synthesized from Compound 70e via four steps according to the method in Example 68. $^1$H NMR (400 MHz, CDCl$_3$) δ 10 (s, 1H), 7.92 (d, J=8.0 Hz, 1H), 7.33 (m, 1H), 7.24 (s, 1H), 4.91 (s, 2H), 3.14 (s, 3H), 2.30 (m, 1H), 0.91 (m, 2H), 0.79 (m, 2H).

Step VII

Compound 70 (42 mg) was synthesized from Compound 70f and Compound 6a according to the method in Example 1. $^1$H NMR (400 MHz, DMSO-d$_6$) δ 7.42 (d, J=8.0 Hz, 1H), 7.25 (m, 1H), 7.20-7.08 (m, 1H), 6.80 (m, 2H), 6.65 (d, J=8.0 Hz, 1H), 4.79 (s, 2H), 4.65 (brs, 2H), 3.99 (s, 2H), 2.97 (s, 3H), 2.31 (brs, 3H), 2.19-2.10 (m, 1H), 0.76-0.61 (m, 4H). MS-ESI calculated value [M+H]$^+$ 458, measured value 458.

Example 71

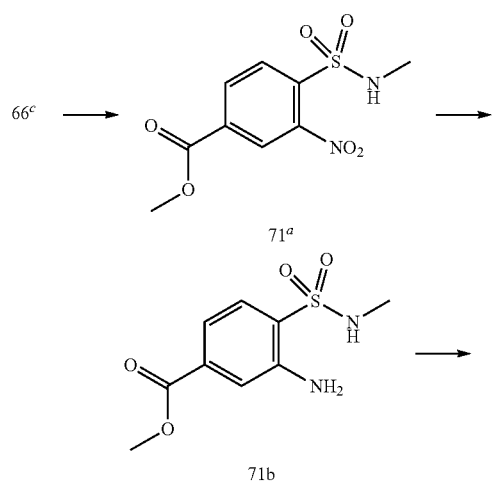

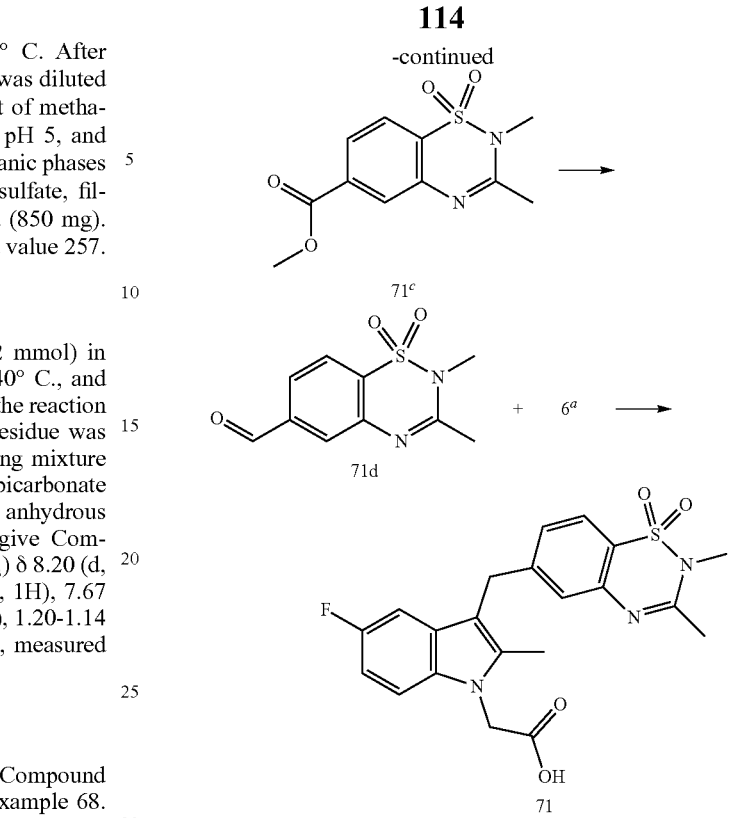

Step I

A solution of methylamine in ethanol (9.26 g, 89.40 mmol, purity: 30%) was added to a solution of Compound 66c (5 g, 17.88 mmol) in acetonitrile (50 mL). The resulting reaction mixture was stirred for 1 hr at 25° C. After completion of the reaction, the reaction mixture was diluted with water (100 mL), evaporated to remove most of acetonitrile, and extracted with ethyl acetate (100 mL×2). The organic phases were combined, washed with saturated brine (100 mL×2), dried over anhydrous sodium sulfate, filtered, concentrated, and separated and purified by flash silica gel column chromatography (petroleum ether/ethyl acetate 100-0%), to give Compound 71a (2.30 g). $^1$H NMR (400 MHz, CDCl$_3$) δ 8.47 (d, =−1.6 Hz, 1H), 8.37 (m, 1H), 8.21 (d, =−8.0 Hz, 1H), 5.28-5.26 (m, 1H), 4.01 (s, 3H), 2.82-2.81 (m, 3H).

Step II

Compound 71b (2.00 g) was synthesized from Compound 71a according to the method in Example 66. MS-ESI calculated value [M+H]$^+$ 245, measured value 245.

Step III

A solution of Compound 71b (1.95 g, 7.98 mmol) in triethyl orthoacetate (50 mL) was heated to 130° C., and stirred for 16 hr. After completion of the reaction, the reaction mixture was concentrated to dryness, and the residue was separated and purified by silica gel column chromatography (petroleum ether/ethyl acetate=100-0%), to give Compound 71c (1.50 g). $^1$H NMR (400 MHz, DMSO-d$_6$) δ 8.08-8.04 (m, 1H), 8.02-7.98 (m, 1H), 7.94 (d, J=−1.2

Hz, 1H), 3.91 (s, 3H), 3.47 (s, 3H), 2.51 (s, 3H). MS-ESI calculated value [M+H]⁺ 269, measured value 269.

Step IV

Compound 71d (300 mg) was synthesized from Compound 71c according to the method in Example 66. ¹H NMR (400 MHz, CDCl₃) δ 10.10 (s, 1H), 8.12-7.83 (m, 3H), 3.51 (s, 3H), 2.52 (s, 3H). MS-ESI calculated value [M+H]⁺ 239, measured value 239.

Step VI

Compound 71 (198 mg) was synthesized from Compound 71e and Compound 6a according to the method in Example 1. ¹H NMR (400 MHz, DMSO-d₆) δ 9.24 (s, 1H), 8.09 (brs, 1H), 7.68-7.59 (m, 2H), 7.35 (m, 1H), 7.18-7.08 (m, 2H), 6.91-6.81 (m, 1H), 4.96 (s, 2H), 4.05 (s, 2H), 2.39-2.37 (m, 3H), 2.33 (s, 3H), 2.09 (s, 3H). MS-ESI calculated value [M+MeCN]⁺430, measured value 430.

Example 72

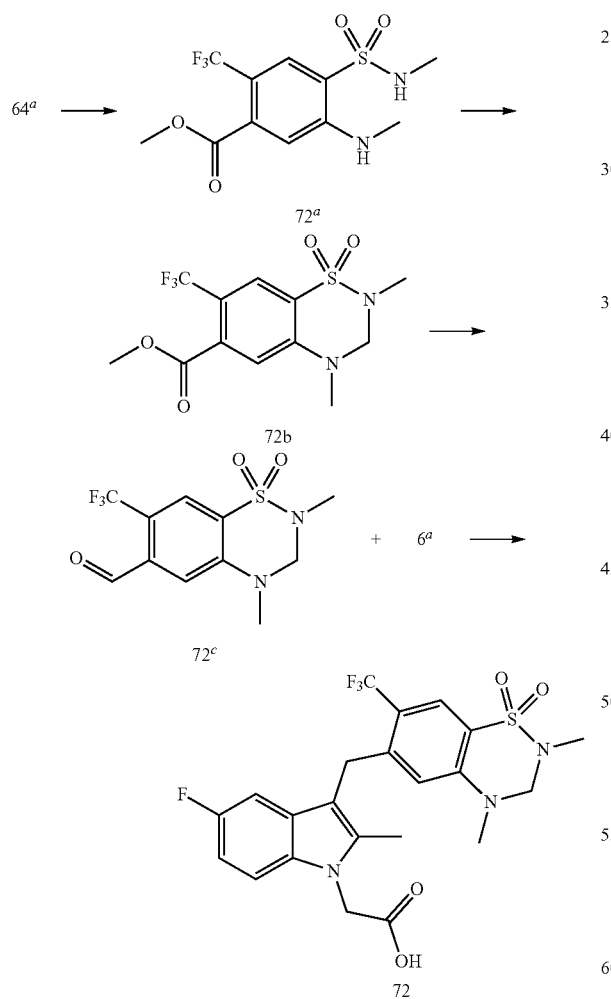

Step I

Compound 64a (2.00 g, 5.32 mmol) was dissolved in methanol (40 mL), and methylamine (ethanol solution, 10.01 g, 106.34 mmol, 30%) was added. The reaction mixture was stirred for 13 hr at 65° C. The reaction mixture was cooled to room temperature, and water (30 mL) was added to quench the reaction. The resulting mixture was extracted with dichloromethane (120 mL×2). The organic phases were combined, washed with saturated brine (100 mL), dried over anhydrous sodium sulfate, filtered, and concentrated under reduced pressure. The residue was separated and purified by silica gel column chromatography (petroleum ether/ethyl acetate=100-0%), to give Compound 72a (950 mg). ¹H NMR (400 MHz, CDCl₃) δ 8.05 (s, 1H), 7.04 (s, 1H), 6.41 (brs, 1H), 4.58 (brs, 1H), 3.96 (s, 3H), 2.97 (d, J=5.2 Hz, 3H), 2.63 (d, J=5.6 Hz, 3H).

Step II

Compound 72a (950 mg, 2.91 mmol) was dissolved in ethanol (15 mL) and 1,2-dichloroethane (8 mL), and polyformaldehyde (600 mg, 2.91 mmol) and concentrated sulfuric acid (0.2 mL) were added. The resulting reaction mixture was stirred for 3 hr at 80° C. The reaction mixture was cooled to room temperature, and a saturated aqueous solution of sodium bicarbonate (20 mL) was added to quench the reaction. The resulting mixture was extracted with dichloromethane (30 mL×2). The organic phases were combined, washed with saturated brine (50 mL), dried over anhydrous sodium sulfate, filtered, and concentrated under reduced pressure. The residue was separated and purified by silica gel column chromatography (petroleum ether/ethyl acetate=100-0%), to give Compound 72b (820 mg). ¹H NMR (400 MHz, CDCl₃) δ 8.05 (s, 1H), 7.06 (s, 1H), 4.93 (s, 2H), 3.96 (s, 3H), 3.12 (s, 3H), 2.82 (s, 3H).

Step III

Compound 72c (350 mg) was synthesized from Compound 72b through a two-step reaction according to the method in Example 43. ¹H NMR (400 MHz, CDCl₃) δ 10.35 (s, 1H), 8.10 (s, 1H), 7.43 (s, 1H), 4.95 (s, 2H), 3.17 (s, 3H), 2.83 (s, 3H).

Step IV

Compound 72 (58 mg) was synthesized from Compound 72c and Compound 6a according to the method in Example 1. ¹H NMR (400 MHz, CD₃OD) δ 7.86 (s, 1H), 7.32-7.28 (m, 1H), 6.91-6.86 (m, 2H), 6.43 (s, 1H), 5.04 (s, 2H), 4.84 (s, 2H), 4.22 (s, 2H), 2.69-2.67 (m, 6H), 2.33 (s, 3H). MS-ESI calculated value [M+H]⁺ 500, measured value 500.

Example 73

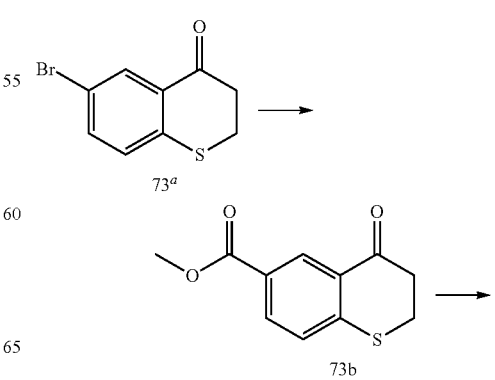

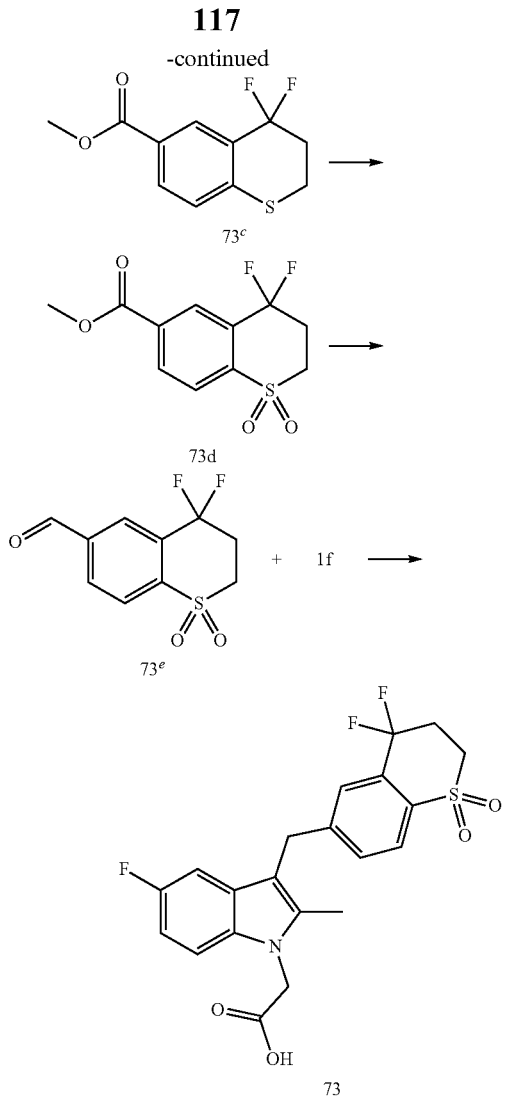

73c

73d

73e

73

Step I

Compound 73b (7.80 g) was synthesized from Compound 73a according to the synthesis method of Compound 46c in Example 46. $^1$H NMR (400 MHz, CDCl$_3$) δ 8.75 (s, 1H), 8.03-8.00 (dd, J=6.0 Hz, J=8.0 Hz, 1H), 7.37-7.35 (d, J=8.0 Hz, 1H), 3.93 (s, 3H), 3.32-3.28 (m, 2H), 3.04-3.00 (m, 2H).

Step II

Compound 73b (7.00 g, 31.49 mmol) was slowly added in batch to a solution of bis(2-methoxyethyl)amino in sulfur trifluoride (35 mL). The resulting reaction mixture was stirred for 4 hr at 90° C. After completion of the reaction, the reaction mixture was cooled to room temperature, and diluted with dichloromethane (40 mL). The resulting reaction mixture was slowly added to a saturated aqueous solution of sodium bicarbonate (100 mL) at 0° C. to quench the reaction. The resulting mixture was extracted with dichloromethane (50 mL×2). The organic phases were combined, washed with saturated brine (100 mL×1), dried over anhydrous sodium sulfate, filtered, and concentrated under reduced pressure. The residue was separated and purified by silica gel column chromatography (petroleum ether/ethyl acetate=100-0%), to give Compound 73c (5.80 g). $^1$H NMR (400 MHz, CDCl$_3$) δ 8.38 (s, 1H), 7.94-7.91 (m, 1H), 7.25-7.23 (m, 1H), 3.93 (s, 3H), 3.22-3.19 (m, 2H), 2.65-2.54 (m, 2H).

Step III

Compound 73c (5.56 g, 22.93 mmol) was dissolved in dichloromethane (60 mL), and m-chloroperoxybenzoic acid (9.31 g, 45.85 mmol, 85%) was added at 0° C. The resulting reaction mixture was stirred for 3 hr at 25° C. After completion of the reaction, the reaction mixture was filtered. A saturated solution of sodium thiosulfate (20 mL) was added to the filtrate to quench the reaction. The organic phase was washed with a saturated aqueous solution of sodium bicarbonate (50 mL), dried over anhydrous sodium sulfate, filtered, and concentrated under reduced pressure. The residue was separated and purified by silica gel column chromatography (petroleum ether/ethyl acetate=100-0%), to give Compound 73d (4.40 g). $^1$H NMR (400 MHz, CDCl$_3$) δ 8.47 (s, 1H), 8.36-8.34 (m, 1H), 8.05-8.03 (m, 1H), 4.00 (s, 3H), 3.65-3.62 (m, 2H), 3.12-3.06 (m, 2H).

Step IV

Compound 73e (3.70 g) was synthesized from Compound 73d according to the synthesis method of Compound 43f in Example 43. $^1$H NMR (400 MHz, CDCl$_3$) δ 10.14 (s, 1H), 8.31 (s, 1H), 8.23-8.21 (m, 1H), 8.15-8.13 (m, 1H), 3.68-3.64 (m, 2H), 3.12-3.06 (m, 2H).

Step V

Compound 73 (2.75 g) was synthesized from Compound 73d and Compound 1f through a three-step reaction according to the method in Example 1. $^1$H NMR (400 MHz, DMSO-d$_6$) δ 13.02 (s, 1H), 7.84-7.82 (m, 1H), 7.71-7.70 (m, 1H), 7.64-7.61 (m, 1H), 7.38-7.37 (m, 1H), 7.22-7.19 (m, 1H), 6.90-6.86 (m, 1H), 4.98 (s, 2H), 4.20 (s, 2H), 3.81-3.78 (m, 2H), 3.02-2.94 (m, 2H), 2.32 (s, 3H). MS-ESI calculated value [M+H]$^+$ 438, measured value 438.

Example 74

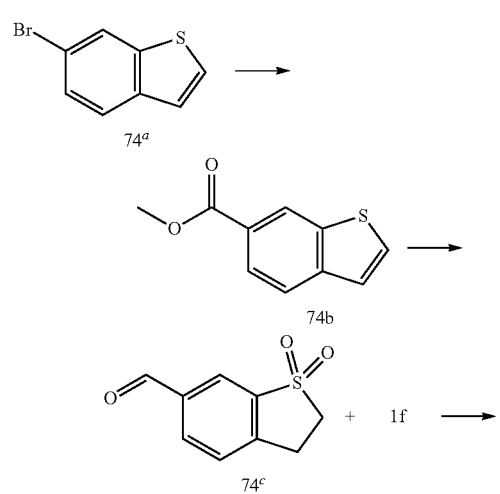

74a

74b

74c

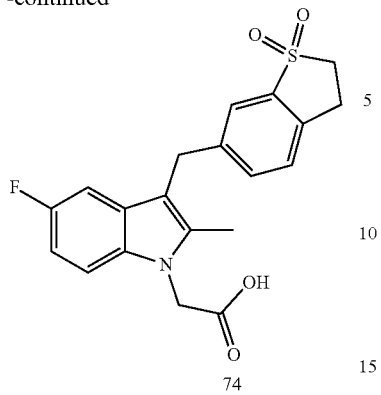

74

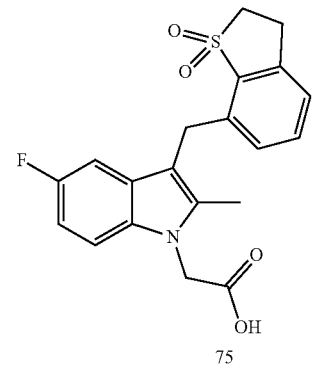

75

Step I

Compound 74b (2.60 g) was synthesized from Compound 74a according to the synthesis method of Compound 46c in Example 46. $^1$H NMR (400 MHz, CDCl$_3$) δ 8.62 (s, 1H), 8.05-8.02 (m, 1H), 7.88-7.85 (m, 1H), 7.66-7.64 (m, 1H), 7.41-7.39 (m, 1H), 3.97 (s, 3H).

Step II

Compound 74c (180 mg) was synthesized from Compound 74b according to the synthesis method in Example 43. $^1$H NMR (400 MHz, CDCl$_3$) δ 10.06 (s, 1H), 8.13-8.10 (m, 1H), 7.58-7.56 (m, 1H), 3.60-3.56 (m, 2H), 3.51-3.48 (m, 2H).

Step III

Compound 74 (41 mg) was synthesized from Compound 74c and Compound 1f according to the method in Example 12. $^1$H NMR (400 MHz, DMSO-d$_6$) δ 7.54-7.45 (m, 2H), 7.41-7.39 (m, 1H), 7.38-7.34 (m, 1H), 7.20-7.16 (m, 1H), 6.90-6.84 (m, 1H), 4.97 (s, 2H), 4.11 (s, 2H), 3.57-3.50 (m, 2H), 3.26 (s, 2H), 2.33 (s, 3H). MS-ESI calculated value [M+H]$^+$ 388, measured value 388.

Example 75

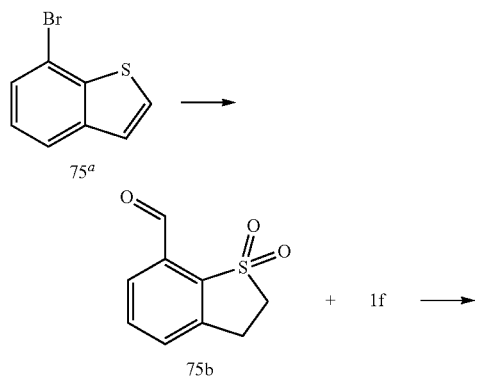

Step I

Compound 75b (80 mg) was synthesized from Compound 75a according to the synthesis method in Example 74. $^1$H NMR (400 MHz, CDCl$_3$) δ 10.59 (s, 1H), 8.03 (d, =−7.6 Hz, 1H), 7.74 (t, J=7.6 Hz, 1H), 7.64-7.62 (m, 1H), 3.64-3.61 (m, 2H), 3.52-3.48 (m, 2H).

Step II

Compound 75 (44 mg) was synthesized from Compound 75b and Compound 1f according to the method in Example 1. $^1$H NMR (400 MHz, CD$_3$OD) δ 7.37-7.35 (m, 1H), 7.25-7.21 (m, 2H), 6.99-6.91 (m, 2H), 6.83 (m, 1H), 4.94 (s, 2H), 4.38 (s, 2H), 3.63-3.59 (m, 2H), 3.42-3.39 (m, 2H), 2.34 (s, 3H). MS-ESI calculated value [M+H]$^+$ 388, measured value 388.

Example 76

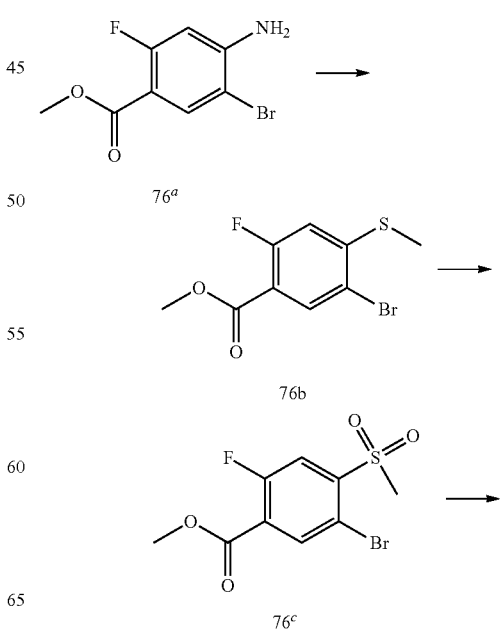

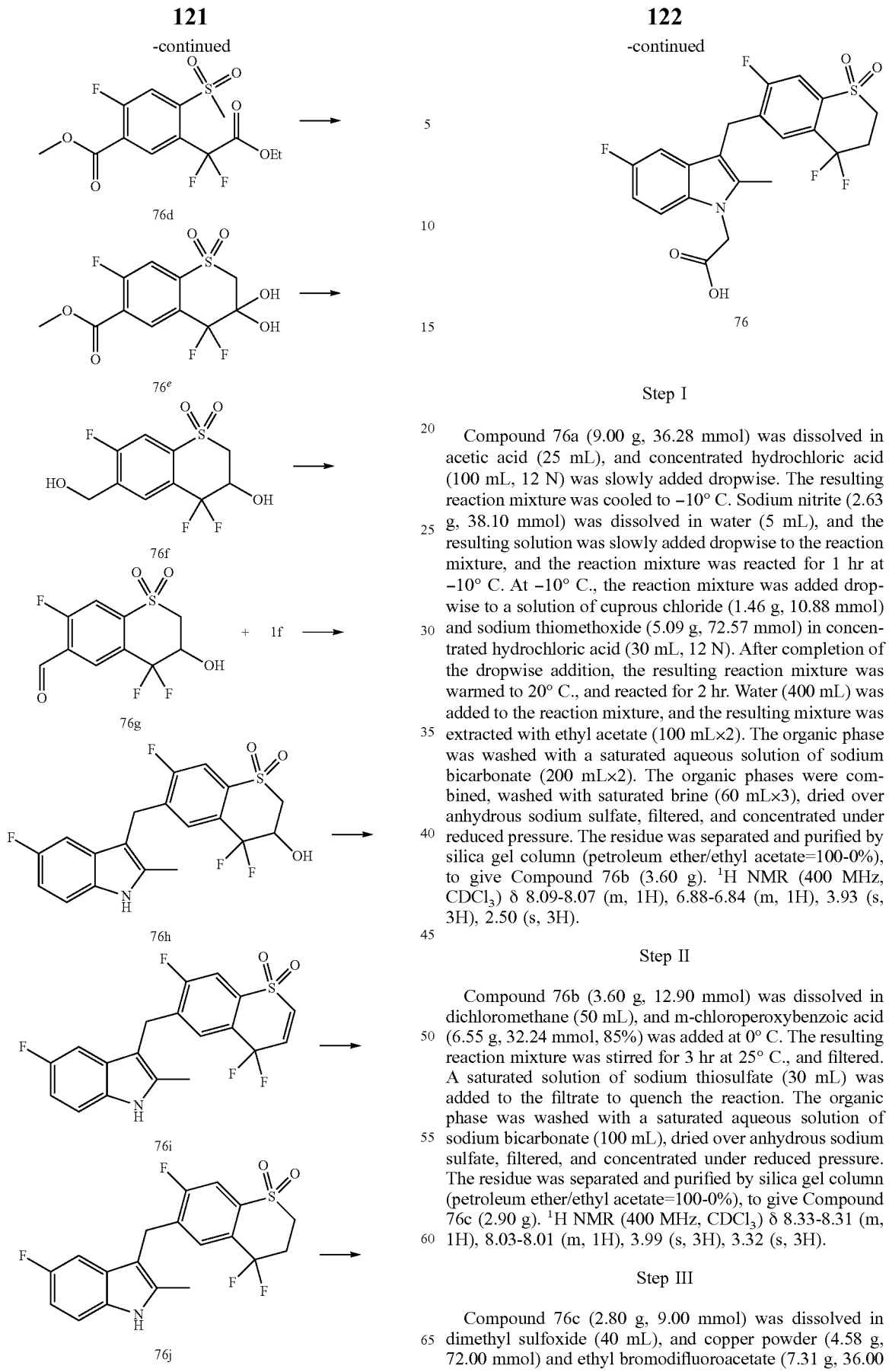

Step I

Compound 76a (9.00 g, 36.28 mmol) was dissolved in acetic acid (25 mL), and concentrated hydrochloric acid (100 mL, 12 N) was slowly added dropwise. The resulting reaction mixture was cooled to −10° C. Sodium nitrite (2.63 g, 38.10 mmol) was dissolved in water (5 mL), and the resulting solution was slowly added dropwise to the reaction mixture, and the reaction mixture was reacted for 1 hr at −10° C. At −10° C., the reaction mixture was added dropwise to a solution of cuprous chloride (1.46 g, 10.88 mmol) and sodium thiomethoxide (5.09 g, 72.57 mmol) in concentrated hydrochloric acid (30 mL, 12 N). After completion of the dropwise addition, the resulting reaction mixture was warmed to 20° C., and reacted for 2 hr. Water (400 mL) was added to the reaction mixture, and the resulting mixture was extracted with ethyl acetate (100 mL×2). The organic phase was washed with a saturated aqueous solution of sodium bicarbonate (200 mL×2). The organic phases were combined, washed with saturated brine (60 mL×3), dried over anhydrous sodium sulfate, filtered, and concentrated under reduced pressure. The residue was separated and purified by silica gel column (petroleum ether/ethyl acetate=100-0%), to give Compound 76b (3.60 g). $^1$H NMR (400 MHz, CDCl$_3$) δ 8.09-8.07 (m, 1H), 6.88-6.84 (m, 1H), 3.93 (s, 3H), 2.50 (s, 3H).

Step II

Compound 76b (3.60 g, 12.90 mmol) was dissolved in dichloromethane (50 mL), and m-chloroperoxybenzoic acid (6.55 g, 32.24 mmol, 85%) was added at 0° C. The resulting reaction mixture was stirred for 3 hr at 25° C., and filtered. A saturated solution of sodium thiosulfate (30 mL) was added to the filtrate to quench the reaction. The organic phase was washed with a saturated aqueous solution of sodium bicarbonate (100 mL), dried over anhydrous sodium sulfate, filtered, and concentrated under reduced pressure. The residue was separated and purified by silica gel column (petroleum ether/ethyl acetate=100-0%), to give Compound 76c (2.90 g). $^1$H NMR (400 MHz, CDCl$_3$) δ 8.33-8.31 (m, 1H), 8.03-8.01 (m, 1H), 3.99 (s, 3H), 3.32 (s, 3H).

Step III

Compound 76c (2.80 g, 9.00 mmol) was dissolved in dimethyl sulfoxide (40 mL), and copper powder (4.58 g, 72.00 mmol) and ethyl bromodifluoroacetate (7.31 g, 36.00 mmol) were added under a N$_2$ atmosphere. The resulting reaction mixture was stirred for 6 hr at 70° C. The reaction mixture was cooled to room temperature, and water (50 mL) and ethyl acetate (40 mL) were added. The resulting mixture was filtered, the filtrate was stratified, and the aqueous phase was extracted with ethyl acetate (40 mL×2). The organic phases were combined, washed with saturated brine (40 mL), dried over anhydrous sodium sulfate, filtered, and concentrated under reduced pressure. The residue was separated and purified by silica gel column (petroleum ether/ethyl acetate=100-0%), to give Compound 76d (2.40 g). $^1$H NMR (400 MHz, CDCl$_3$) δ 8.50-8.47 (m, 1H), 7.99-7.96 (m, 1H), 4.34 (q, J=7.2 Hz, 2H), 4.02 (s, 3H), 3.20 (s, 3H), 1.31 (t, J=7.2 Hz, 3H).

Step IV

Compound 76d (2.20 g, 6.21 mmol) was dissolved in anhydrous tetrahydrofuran (30 mL), and a solution of lithium bis(trimethylsilyl)amide in tetrahydrofuran (1M, 8.69 mmol, 8.69 mL) was slowly added dropwise at −78° C. The resulting reaction mixture was further stirred for 0.5 hr at −78° C. Diluted hydrochloric acid (4 N, 20 mL) was added to the reaction mixture, and the resulting reaction mixture was warmed to room temperature, and further stirred for 0.5 hr. Ethyl acetate (30 mL) was added to the reaction mixture, and stratified. The aqueous phase was extracted with ethyl acetate (30 mL). The organic phases were combined, washed with saturated brine (40 mL), dried over anhydrous sodium sulfate, filtered, and concentrated under reduced pressure, to give Compound 76e (1.90 g). $^1$H NMR (400 MHz, CDCl$_3$) δ 8.48-8.43 (m, 1H), 7.74-7.70 (m, 1H), 4.05-3.91 (m, 5H), 3.53 (s, 2H).

Step V

Compound 76e (1.90 g, 5.82 mmol) was dissolved in tetrahydrofuran (20 mL) and methanol (20 mL), and sodium borohydride (440 mg, 11.65 mmol) was added at 0° C. The resulting reaction mixture was stirred for 4 hr at 25° C., and an aqueous solution of hydrochloric acid (1 M, 30 mL) was added to quench the reaction. The organic solvent was removed under reduced pressure, and the remaining aqueous phase was extracted with ethyl acetate (20 mL×3). The organic phase was dried over anhydrous sodium sulfate, filtered, and concentrated under reduced pressure. The residue was separated and purified by silica gel column (petroleum ether/ethyl acetate=100-0%), to give Compound 76f (900 mg). $^1$H NMR (400 MHz, CD$_3$OD) δ 8.09-8.07 (m, 1H), 7.64-7.62 (m, 1H), 4.77 (s, 2H), 4.74-4.68 (m, 1H), 3.90-3.77 (m, 2H).

Step VI

Compound 76f (800 mg, 2.83 mmol) was dissolved in tetrahydrofuran (10 mL), and activated manganese dioxide (1.72 g, 19.84 mmol) was added. The resulting reaction mixture was stirred for 2 hr at 40° C., and then filtered. The filtrate was directly concentrated, to give Compound 76g (560 mg). $^1$H NMR (400 MHz, CDCl$_3$) δ 10.42 (s, 1H), 8.44-8.42 (m, 1H), 7.82-7.79 (m, 1H), 4.88-4.79 (m, 1H), 3.93-3.83 (m, 2H), 3.28 (brs, 1H).

Step VII

Compound 76h (640 mg) was synthesized from Compound 76g and Compound 1f according to the method in Example 1. $^1$H NMR (400 MHz, CDCl$_3$) δ 7.94 (br s, 1H), 7.65-7.54 (m, 2H), 7.24-7.20 (m, 1H), 7.01-6.98 (m, 1H), 6.91-6.86 (m, 1H), 4.74 (br s, 1H), 4.11 (s, 2H), 3.83-3.67 (m, 2H), 3.19-3.17 (m, 1H), 2.42 (s, 3H). MS-ESI calculated value [M+H]$^+$ 414, measured value 414.

Step VIII

Compound 76h (640 mg, 1.55 mmol) was dissolved in dichloromethane (15 mL), and triethylamine (626 mg, 6.19 mmol) and methanesulfonyl chloride (230 mg, 2.01 mmol) were added at 0° C. The resulting reaction mixture was stirred for 0.5 hr at 0° C., and water (20 mL) was added to quench the reaction. The resulting mixture was extracted with dichloromethane (20 mL×2). The organic phase was dried over anhydrous sodium sulfate, filtered, and concentrated under reduced pressure, to give Compound 76i (560 mg). $^1$H NMR (400 MHz, CDCl$_3$) δ 7.95 (br s, 1H), 7.68-7.65 (m, 1H), 7.57-7.55 (m, 1H), 7.24-7.20 (m, 1H), 7.03-6.85 (m, 3H), 6.67-6.59 (m, 1H), 4.12 (s, 2H), 2.42 (s, 3H). MS-ESI calculated value [M+H]$^+$ 396, measured value 396.

Step IX

Compound 76i (560 mg, 1.42 mmol) was dissolved in tetrahydrofuran (15 mL) and methanol (5 mL), and sodium borohydride (80 mg, 2.12 mmol) was added at 0° C. The resulting reaction mixture was stirred for 1 hr at 0° C., and water (10 mL) was added to quench the reaction. The resulting mixture was extracted with ethyl acetate (30 mL×2). The organic phase was dried over anhydrous sodium sulfate, filtered, and concentrated under reduced pressure. The residue was separated and purified by silica gel column chromatography (petroleum ether/ethyl acetate=100-0%), to give Compound 76j (410 mg). $^1$H NMR (400 MHz, CDCl$_3$) δ 7.91 (brs, 1H), 7.61-7.58 (m, 1H), 7.50-7.48 (m, 1H), 7.23-7.19 (m, 1H), 7.01-6.98 (m, 1H), 6.90-6.85 (m, 1H), 4.10 (s, 2H), 3.58-3.52 (m, 2H), 3.02-2.91 (m, 2H), 2.41 (s, 3H). MS-ESI calculated value [M+H]$^+$ 398, measured value 398.

Step X

Compound 76 (63 mg) was synthesized from Compound 76j according to the method in Example 1. $^1$H NMR (400 MHz, DMSO-d$_6$) δ 7.79-7.76 (m, 1H), 7.72-7.69 (m, 1H), 7.40-7.36 (m, 1H), 7.22-7.19 (m, 1H), 6.91-6.86 (m, 1H), 4.98 (s, 2H), 4.18 (s, 2H), 3.85-3.82 (m, 2H), 3.01-2.91 (m, 2H), 2.31 (s, 3H). MS-ESI calculated value [M+H]$^+$ 456, measured value 456.

Example 77

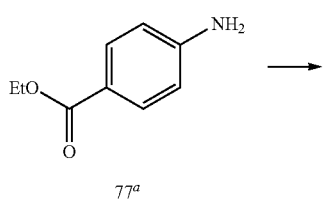

77$^a$

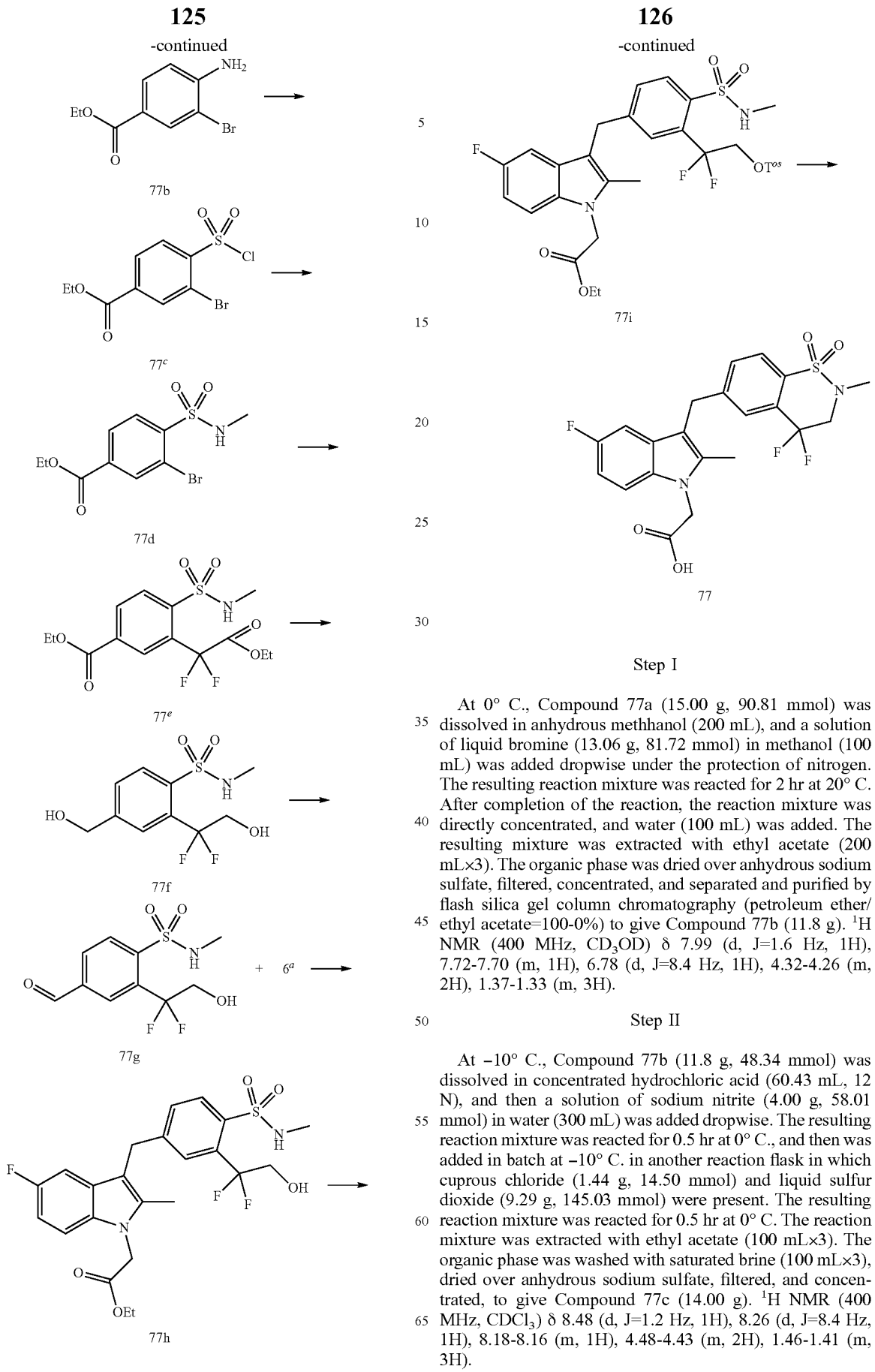

Step I

At 0° C., Compound 77a (15.00 g, 90.81 mmol) was dissolved in anhydrous methhanol (200 mL), and a solution of liquid bromine (13.06 g, 81.72 mmol) in methanol (100 mL) was added dropwise under the protection of nitrogen. The resulting reaction mixture was reacted for 2 hr at 20° C. After completion of the reaction, the reaction mixture was directly concentrated, and water (100 mL) was added. The resulting mixture was extracted with ethyl acetate (200 mL×3). The organic phase was dried over anhydrous sodium sulfate, filtered, concentrated, and separated and purified by flash silica gel column chromatography (petroleum ether/ethyl acetate=100-0%) to give Compound 77b (11.8 g). $^1$H NMR (400 MHz, CD$_3$OD) δ 7.99 (d, J=1.6 Hz, 1H), 7.72-7.70 (m, 1H), 6.78 (d, J=8.4 Hz, 1H), 4.32-4.26 (m, 2H), 1.37-1.33 (m, 3H).

Step II

At −10° C., Compound 77b (11.8 g, 48.34 mmol) was dissolved in concentrated hydrochloric acid (60.43 mL, 12 N), and then a solution of sodium nitrite (4.00 g, 58.01 mmol) in water (300 mL) was added dropwise. The resulting reaction mixture was reacted for 0.5 hr at 0° C., and then was added in batch at −10° C. in another reaction flask in which cuprous chloride (1.44 g, 14.50 mmol) and liquid sulfur dioxide (9.29 g, 145.03 mmol) were present. The resulting reaction mixture was reacted for 0.5 hr at 0° C. The reaction mixture was extracted with ethyl acetate (100 mL×3). The organic phase was washed with saturated brine (100 mL×3), dried over anhydrous sodium sulfate, filtered, and concentrated, to give Compound 77c (14.00 g). $^1$H NMR (400 MHz, CDCl$_3$) δ 8.48 (d, J=1.2 Hz, 1H), 8.26 (d, J=8.4 Hz, 1H), 8.18-8.16 (m, 1H), 4.48-4.43 (m, 2H), 1.46-1.41 (m, 3H).

Step III

At 20° C., Compound 77c (14.00 g, 42.74 mmol) was dissolved in acetonitrile (200 mL), and a solution of methylamine (427 mmol, 213.69 mL) was added dropwise under the protection of nitrogen. The resulting reaction mixture was reacted for 12 hr at 20° C.

Water (100 mL) was added to quench the reaction. The resulting mixture was extracted with ethyl acetate (100 mL×3). The organic phase was dried over anhydrous sodium sulfate, filtered, concentrated, and separated and purified by flash silica gel column chromatography (petroleum ether/ethyl acetate=100-0%), to give Compound 77d (10.8 g). $^1$H NMR (400 MHz, CDCl$_3$) δ 8.39 (d, J=1.6 Hz, 1H), 8.22 (d, J=8.4 Hz, 1H), 8.13-8.11 (m, 1H), 5.13-5.09 (m, 1H), 4.44 (q, J=7.2 Hz, 2H), 2.65-2.64 (m, 3H), 1.43 (t, J=7.2 Hz, 3H).

Step IV

Compound 77e (11.10 g) was synthesized according to the synthesis method of Compound 76d in Example 76. $^1$H NMR (400 MHz, CDCl$_3$) δ 8.55 (d, J=1.6 Hz, 1H), 8.32 (dd, J=1.6, 8.4 Hz, 1H), 8.15 (d, J=8.4 Hz, 1H), 4.71-4.70 (m, 1H), 4.46 (q, J=7.2 Hz, 2H), 4.34 (q, J=7.2 Hz, 2H), 2.75-2.69 (m, 3H), 1.44 (t, J=7.2 Hz, 3H).

Step V

At 0° C., Compound 77e (11.00 g, 30.11 mmol) was dissolved in tetrahydrofuran (200 mL), and lithium aluminum hydride (5.71 g, 150.54 mmol) was added. The resulting reaction mixture was reacted for 2 hr at 20° C. under the protection of nitrogen. Water (150 mL) was slowly added at 0° C. to quench the reaction. The resulting mixture was extracted with ethyl acetate (50 mL×3). The organic phase was dried over anhydrous sodium sulfate, filtered, concentrated, and separated and purified by flash silica gel column chromatography (petroleum ether/ethyl acetate=100-0%), to give Compound 77f (3.90 g). $^1$H NMR (400 MHz, CD$_3$OD) δ 8.06 (d, J=8.0 Hz, 1H), 7.75 (s, 1H), 7.64 (d, J=8.0 Hz, 1H), 4.73 (s, 2H), 4.18 (t, J=14.4 Hz, 2H), 2.59 (s, 3H).

Step VI

Compound 77g (1.15 g) was synthesized from Compound 77f according to the synthesis method of Compound 43f in Example 43. $^1$H NMR (400 MHz, CDCl$_3$) δ 10.15 (s, 1H), 8.37 (d, J=8.0 Hz, 1H), 8.23 (d, F=1.6 Hz, 1H), 8.12 (dd, F=1.6, 8.0 Hz, 1H), 4.72 (brs, 1H), 4.35-4.26 (m, 2H), 2.72 (d, J=5.2 Hz, 3H), 2.51 (t, J=7.2 Hz, 1H).

Step VII

Compound 77h (535 mg) was synthesized from Compound 6a and Compound 77g according to the method in Example 1. MS-ESI calculated value [M+H]$^+$ 499, measured value 499.

Step VIII

At 25° C., Compound 77h (535 mg, 1.07 mmol) was dissolved in dichloromethane (10 mL), and p-toluenesulfonyl chloride (225 mg, 1.18 mmol) and triethylamine (326 mg, 3.22 mmol) were added. The resulting reaction mixture was reacted for 16 hr at 25° C. under the protection of nitrogen. After completion of the reaction, the reaction mixture was concentrated directly. The crude product was separated and purified by flash silica gel column chromatography (petroleum ether/ethyl acetate=100-0%), to give Compound 77i (440 mg). MS-ESI calculated value [M+H]$^+$ 654, measured value 654.

Step IX

At 0° C., Compound 77i (440 mg, 0.67 mmol) was dissolved in tetrahydrofuran (10 mL), and sodium hydride (54 mg, 1.35 mmol, 60%) was added. The resulting reaction mixture was reacted for 2 hr at 20° C. under the protection of nitrogen, and then water (5 mL) was added. After completion of the reaction, the reaction mixture was directly concentrated, and the crude product was separated by high performance liquid chromatography column to give Compound 77 (48 mg). $^1$H NMR (400 MHz, CDCl$_3$) δ 7.71 (d, J=7.6 Hz, 1H), 7.60 (s, 1H), 7.41 (d, J=8.4 Hz, 1H), 7.13 (dd, J=4.0, J=8.8 Hz, 1H), 7.01-6.98 (m, 1H), 6.94-6.93 (m, 1H), 4.88 (s, 2H), 4.20-4.17 (m, 2H), 4.16-4.14 (m, 2H), 3.03 (s, 3H), 2.34 (s, 3H). MS-ESI calculated value [M+H]$^+$ 453, measured value 453.

Example 78

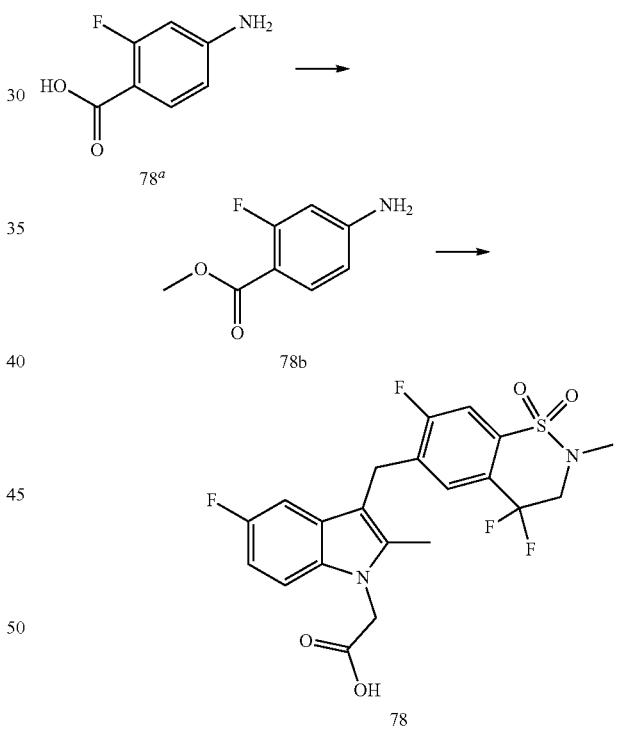

Step I

Compound 78a (24 g, 154.71 mmol) was dissolved in methanol (300 mL) at 25° C., and then sulfoxide chloride (27.61 g, 232.07 mmol) was added at 0° C. The resulting reaction mixture was reacted for 16 hr at 50° C. under the protection of nitrogen. After completion of the reaction, the reaction mixture was directly concentrated, diluted with water (300 mL), and extracted with ethyl acetate (100 mL×3). The organic phase was dried over anhydrous sodium sulfate, filtered, and concentrated, to give Compound 78b (23.8 g). ¹H NMR (400 MHz, CDCl₃) δ 7.77 (t, J=8.4 Hz, 1H), 6.42 (dd, J=2.0, 8.8 Hz, 1H), 6.34 (dd, j=2.4, 12.8 Hz, 1H), 4.81 (s, 2H), 3.87 (s, 3H).

Step II

Compound 78 (2 mg) was synthesized from Compound 78b according to the method in Example 77. ¹H NMR (400 MHz, CD₃OD) δ 7.58 (d, J=8.8 Hz, 1H), 7.53 (d, J=6.8 Hz, 1H), 7.25 (dd, J=4.4, 8.8 Hz, 1H), 7.02-7.01 (m, 1H), 6.90-6.83 (m, 1H), 4.95 (s, 2H), 4.24-4.18 (m, 4H), 2.96 (s, 3H), 2.37 (s, 3H). MS-ESI calculated value [M+H]⁺ 471, measured value 471.

Example 79

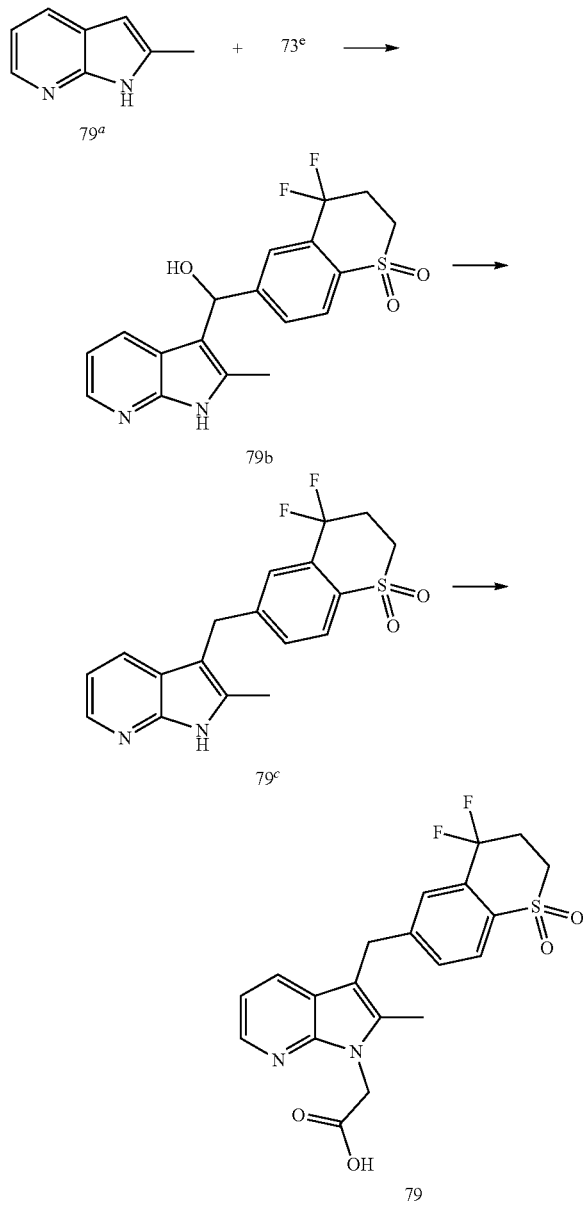

Step I

Compound 79a (200 mg, 1.51 mmol) was dissolved in methanol (5 mL), and Compound 73e (372 mg, 1.51 mmol) and potassium hydroxide (254 mg, 4.54 mmol) were added. The resulting reaction mixture was stirred for 12 hr at 25° C. The reaction mixture was concentrated under reduced pressure, and methanol (5 mL) was added to the residue. The resulting mixture was filtered, to give Compound 79b (320 mg). ¹H NMR (400 MHz, CDCl₃) δ 10.30 (brs, 1H), 8.22-8.20 (m, 1H), 7.98 (s, 1H), 7.90-7.88 (m, 1H), 7.76-7.74 (m, 1H), 7.56-7.54 (m, 1H), 7.00-6.96 (m, 1H), 6.21 (s, 1H), 3.64-3.54 (m, 2H), 3.11-2.98 (m, 2H), 2.55 (s, 3H).

Step II

Compound 79b (320 mg, 0.845 mmol) was dissolved in 1,2-dichloromethane (5 mL), and trifluoroacetic acid (578 mg, 5.07 mmol) and triethylsilane (196 mg, 1.69 mmol) were added. The resulting reaction mixture was stirred for 2 hr at 60° C. Water (10 mL) was added to the reaction mixture to quench the reaction. The resulting mixture was adjusted with a saturated solution of sodium bicarbonate to pH 7, and extracted with dichloromethane (10 mL×3). The organic phases were combined, washed with saturated brine (20 mL), dried over anhydrous sodium sulfate, filtered, and concentrated under reduced pressure. The residue was separated and purified by thin-layer chromatoplates (dichloromethane/methanol=10/1), to give Compound 79c (220 mg). ¹H NMR (400 MHz, CDCl₃) δ 9.52 (brs, 1H), 8.23-8.21 (m, 1H), 7.84-7.81 (m, 1H), 7.65-7.54 (m, 2H), 7.50-7.47 (m, 1H), 7.04-7.00 (m, 1H), 4.17 (s, 2H), 3.63-3.53 (m, 2H), 3.09-2.93 (m, 2H), 2.47 (s, 3H). MS-ESI calculated value [M+H]⁺ 363, measured value 363.

Step III

Compound 79 (120 mg) was synthesized from Compound 79c through a multi-step reaction according to the method in Example 1. ¹H NMR (400 MHz, DMSO-d₆) δ 8.06-8.04 (m, 1H), 7.82-7.79 (m, 1H), 7.74-7.68 (m, 2H), 7.62-7.61 (m, 1H), 6.94-6.90 (m, 1H), 4.50 (s, 2H), 4.22 (s, 2H), 3.83-3.75 (m, 2H), 3.05-2.92 (m, 2H), 2.34 (s, 3H). MS-ESI calculated value [M+H]⁺ 421, measured value 421.

Example 80

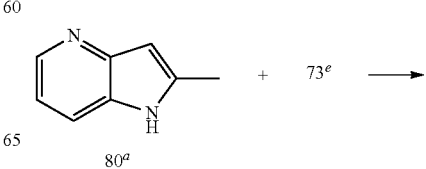

131
-continued

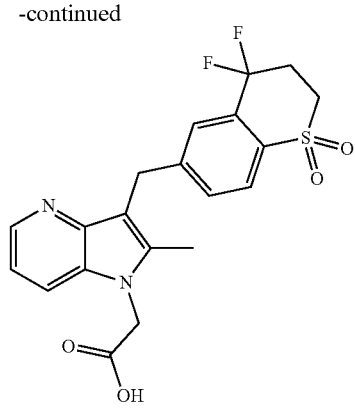

80

Step I

Compound 80 (25 mg) was synthesized from Compound 80a and Compound 73e through a multi-step reaction according to the method in Example 79. $^1$H NMR (400 MHz, DMSO-d$_6$) δ 8.65-8.62 (m, 1H), 8.58-8.56 (m, 1H), 7.85-7.82 (m, 1H), 7.77 (s, 1H), 7.65-7.58 (m, 2H), 5.30 (s, 2H), 4.50 (s, 2H), 3.82-3.79 (m, 2H), 3.04-2.94 (m, 2H), 2.45 (s, 3H). MS-ESI calculated value [M+H]$^+$ 421, measured value 421.

Example 81

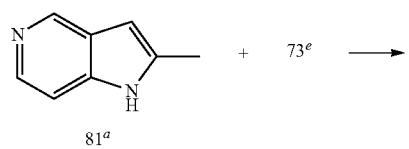 + 73$^e$ →

81

Step I

Compound 81 was synthesized from Compound 81a and Compound 73e through a multi-step reaction according to the method in Example 79. $^1$H NMR (400 MHz, DMSO-d$_6$) δ 9.23 (s, 1H), 8.47-8.44 (m, 1H), 8.15-8.13 (m, 1H), 7.86-7.84 (m, 1H), 7.79-7.77 (m, 1H), 7.66-7.64 (m, 1H), 5.31 (s, 2H), 4.43 (s, 2H), 3.82-3.79 (m, 2H), 3.04-2.94 (m, 2H), 2.45 (s, 3H). MS-ESI calculated value [M+H]$^+$ 421, measured value 421.

132

Example 82

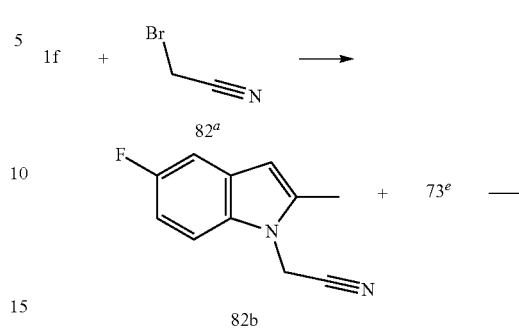

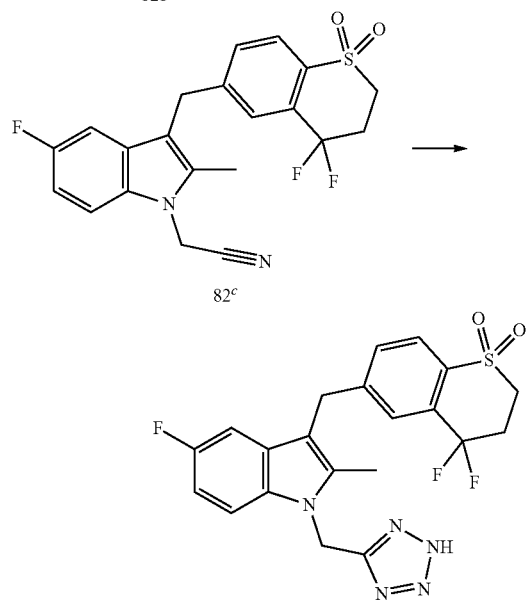

Step I

Cesium carbonate (3.28 g, 10.06 mmol) and Compound 82a (804 mg, 6.70 mmol) were added to a solution of Compound 1f (500 mg, 3.35 mmol) in dimethylformamide (50 mL). The resulting reaction mixture was stirred for 16 hr at 100° C. After completion of the reaction, the reaction mixture was poured into water (500 mL), and extracted with ethyl acetate (100 mL×2). The organic phases were combined, washed with saturated brine (500 mL×2), dried over anhydrous sodium sulfate, filtered, concentrated, and separated and purified by flash silica gel column chromatography (petroleum ether/ethyl acetate 100-0%), to give Compound 82b (125 mg). MS-ESI calculated value [M+H]$^+$ 189, measured value 189.

Step II

Compound 82c (220 mg) was synthesized from Compound 82b and Compound 73e according to the method in Example 1. MS-ESI calculated value [M+H]$^+$ 419, measured value 419.

Step III

Triethylamine hydrochloride (49 mg, 0.36 mmol) and sodium azide (12 mg, 0.18 mmol) were added to a solution of Compound 82c (50 mg, 0.12 mmol) in dimethylformamide (5 mL). The resulting reaction mixture was stirred for 6 hr at 120° C. After completion of the reaction, the reaction mixture was poured into water (100 mL), and extracted with ethyl acetate (200 mL×2). The organic phases were combined, washed with saturated brine (50 mL×1), dried over anhydrous sodium sulfate, filtered, concentrated, and purified by high performance liquid chromatography, to give Compound 82 (8 mg). $^1$H NMR (400 MHz, DMSO-$d_6$) δ 7.80 (d, J=8.4 Hz, 1H), 7.71 (s, 1H), 7.61-7.59 (m, J=8.4 Hz, 1H), 7.50 (brs, 1H), 7.15 (m, 1H), 7.10 (br s, 1H), 6.87 (br s, 1H), 5.48 (br s, 1H), 4.17 (s, 2H), 3.78 (m, 2H), 3.05-2.90 (m, 2H), 2.52-2.51 (m, 3H), 2.07 (s, 1H). MS-ESI calculated value [M+H]$^+$ 462, measured value 462.

Biological Activity Assay

Experimental Method:

PathHunter® CHO-K1 CRTH2 β-arrestin cells (DiscoverX, catalogue number 93-0291C2) grew under standard conditions, and were inoculated into a white-wall 384-well microplate at a density of 5,000 cells/well. 20 μL of Cell Plating Reagent 1 was used in each well. Before the test, the cells were incubated overnight at 37° C./5% CO$_2$. A test compound was serially diluted in DMSO with a dilution factor of 3-fold to give 8 concentrations of the test compound. Shortly before the test, the serially diluted test compound was further diluted with the test buffer to 5 times of the test concentration. 5 μL of the further diluted test compound was added to the cells, and the cells were incubated for 30 min at 37° C. The concentration of the solvent was 1%. 5 μL of 6×EC$_{80}$ agonist (PGD2) buffer was added to the cells, and the cells were incubated for 90 min at 37° C. Measured signals were generated by one-time addition of 15 μL (50% v/v) of PathHunter detection mixture reagent and subsequent one-hour incubation. The microplate was read through the chemiluminescent signals of PerkinElmer Envision™ reader. Biological activity of the test compound was analyzed by CBIS data analysis suite (ChemInnovation, CA), and was denoted as IC$_{50}$ value. The experimental results were shown in Table 1.

TABLE 1

| Compound | IC$_{50}$ |
|---|---|
| Example 1 | +++ |
| Example 2 | ++ |
| Example 3 | ++ |
| Example 4 | +++ |
| Example 5 | ++ |
| Example 6 | +++ |
| Example 9 | ++ |
| Example 10 | ++ |
| Example 11 | ++ |
| Example 12 | ++ |
| Example 13 | +++ |
| Example 15 | ++ |
| Example 16 | ++ |
| Example 17 | ++ |
| Example 18 | ++ |
| Example 19 | ++ |
| Example 20 | ++ |
| Example 21 | ++ |
| Example 22 | +++ |
| Example 26 | + |
| Example 31 | +++ |
| Example 33 | ++ |
| Example 34 | ++ |
| Example 38 | ++ |
| Example 39 | +++ |

TABLE 1-continued

| Compound | IC$_{50}$ |
|---|---|
| Example 43 | +++ |
| Example 44 | ++ |
| Example 45 | ++ |
| Example 46 | ++ |
| Example 47 | +++ |
| Example 48 | ++ |
| Example 49 | ++ |
| Example 50 | ++ |
| Example 51 | ++ |
| Example 52 | ++ |
| Example 53 | + |
| Example 54 | + |
| Example 55 | ++ |
| Example 56 | + |
| Example 57 | ++ |
| Example 58 | + |
| Example 59 | + |
| Example 60 | ++ |
| Example 61 | ++ |
| Example 62 | +++ |
| Example 63 | ++ |
| Example 64 | ++ |
| Example 65 | +++ |
| Example 66 | +++ |
| Example 67 | +++ |
| Example 68 | +++ |
| Example 69 | +++ |
| Example 70 | +++ |
| Example 72 | +++ |
| Example 73 | +++ |
| Example 74 | ++ |
| Example 75 | ++ |
| Example 77 | +++ |
| Example 78 | ++ |
| Example 79 | + |
| Example 80 | ++ |
| Example 81 | + |
| Example 82 | + |

Note:
+ >1.0 μM; ++ 0.1-1.0 μM; +++ <0.1 μM;

Conclusion: The compounds of the present application have strong antagonistic effects on a CRTH2 receptor.

What is claimed is:

1. A compound represented by formula (II), or a pharmaceutically acceptable salt, tautomer, or solvate thereof,

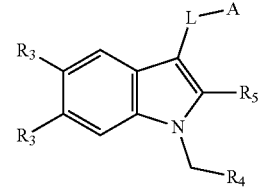

wherein
A is selected from the group consisting of

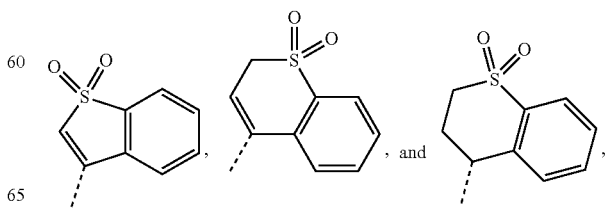

which are substituted with F or Cl, and which are optionally substituted with one or more R₁; and L is a single bond; or A is selected from the group consisting of

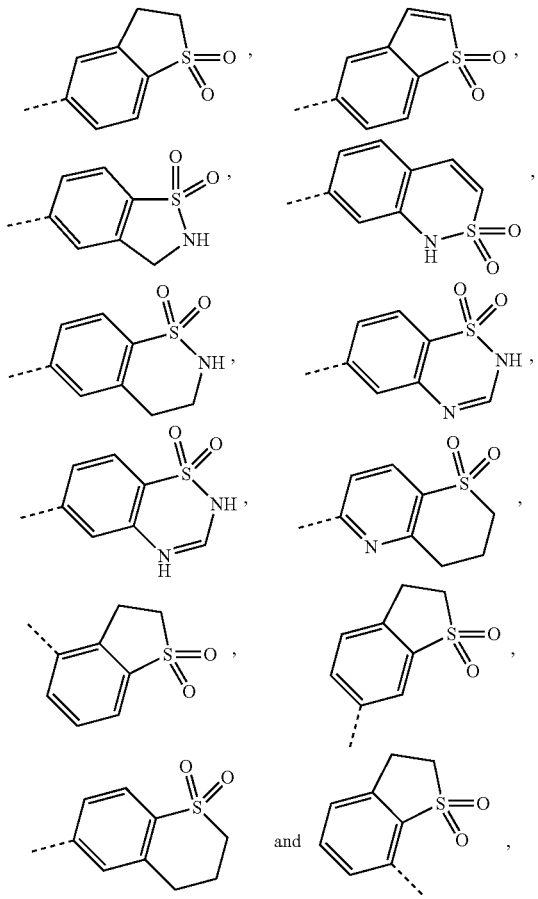

which are substituted with F or Cl, and which are optionally substituted with one or more R₁; and L is methylene optionally substituted with R;

each R₁ is independently selected from the group consisting of F, Cl, Br, I, and —OH; or is independently selected from the following groups: $C_{1-3}$ alkyl, $C_{1-3}$ alkyl-S(=O)₂—, $C_{3-6}$ cycloalkyl, and phenyl, which are optionally substituted with 1, 2, or 3 R;

each R₃ is independently selected from the group consisting of H, F, Cl, Br, I, —OH, and —NO₂; or is independently $C_{1-3}$ alkyl, which is optionally substituted with 1, 2, or 3 R;

R₄ is —COOH;

R₅ is selected from the group consisting of H and $C_{1-3}$ alkyl;

each R is independently selected from the group consisting of F, Cl, Br, I, —CN, —OH, —NH₂, Me, Et, —CF₃, —CHF₂, —CH₂F, —NHCH₃, —N(CH₂)₂,

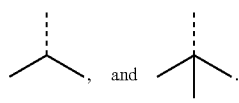

2. The compound according to claim 1, wherein each R is independently selected from the group consisting of F and Cl.

3. The compound according to claim 1, wherein A is selected from the group consisting of

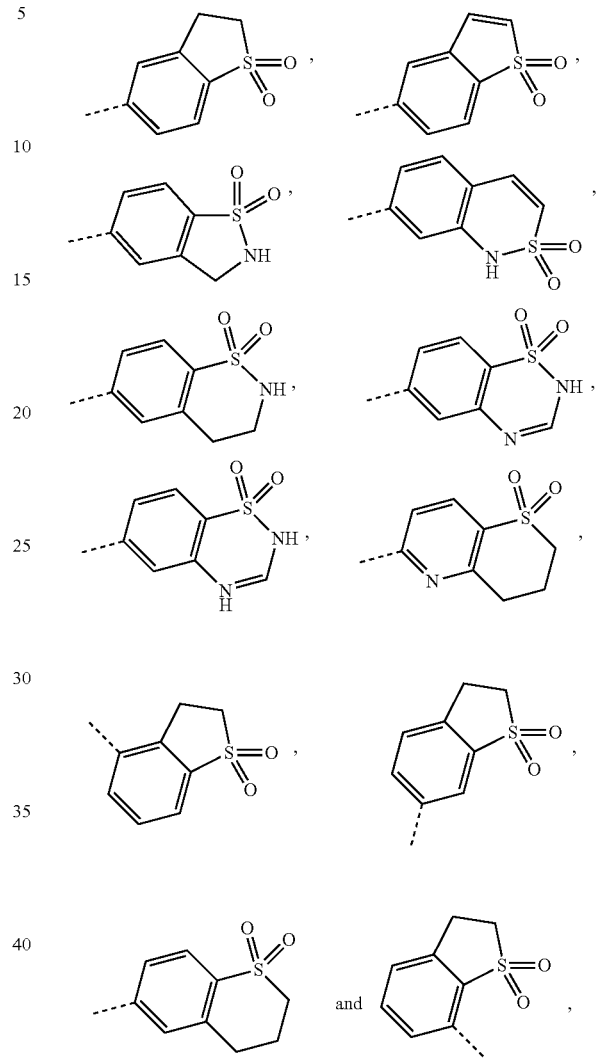

which are substituted with F or Cl, and which are optionally substituted with one or more R₁; and L is selected from the group consisting of CH₂ and —CH(CH₃)—.

4. A compound selected from the group consisting of:

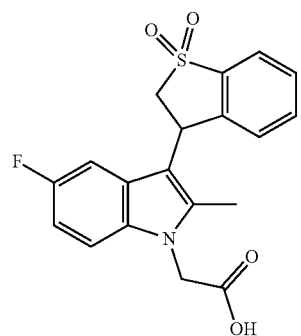

137
-continued
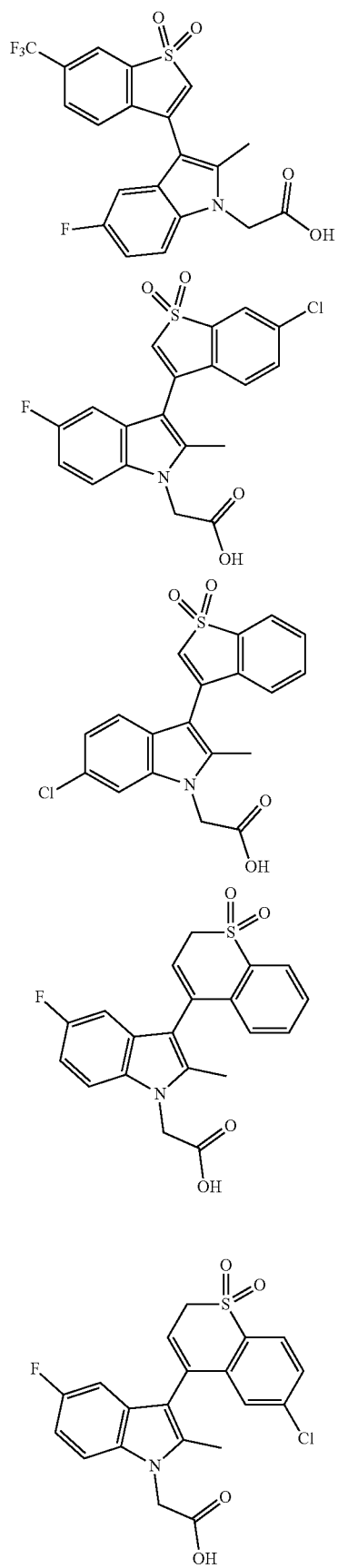
138
-continued
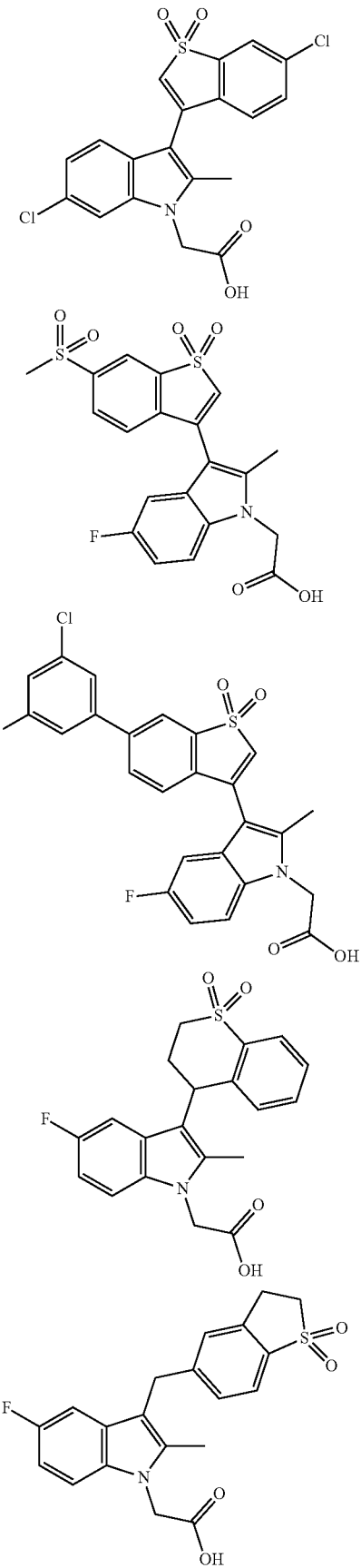

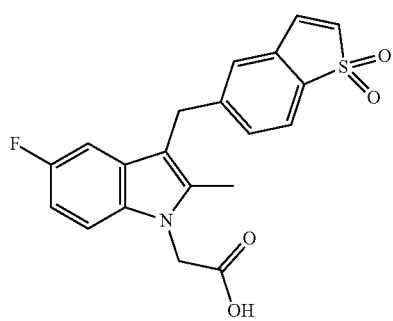
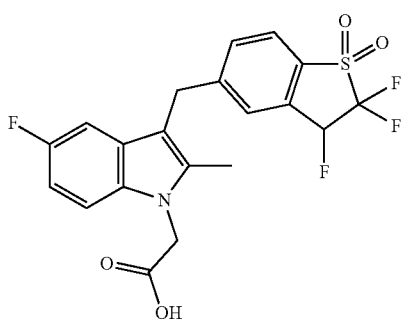
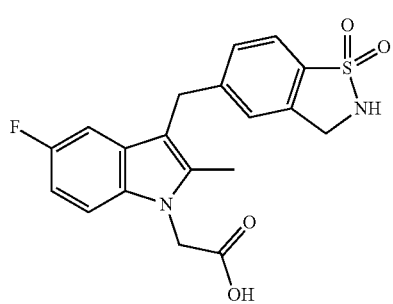
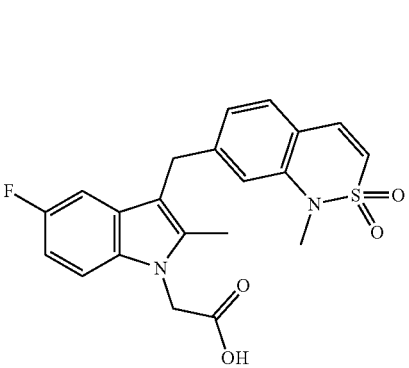
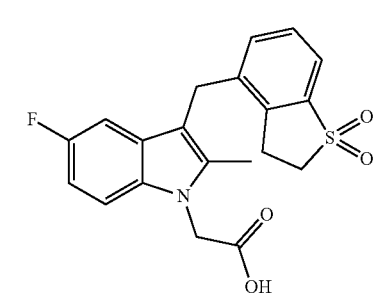
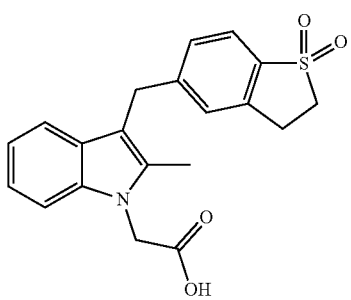
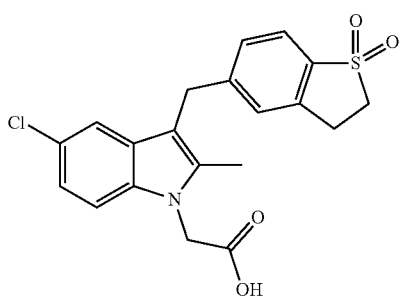
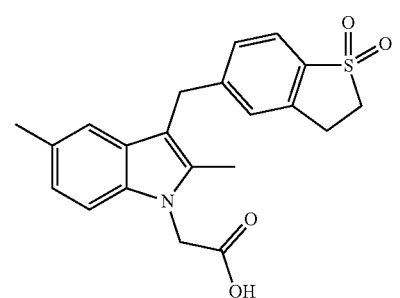
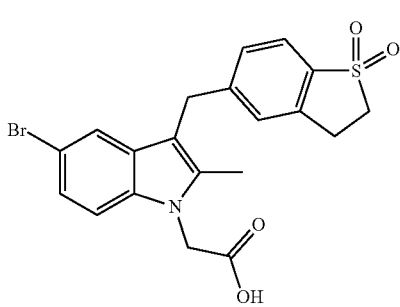
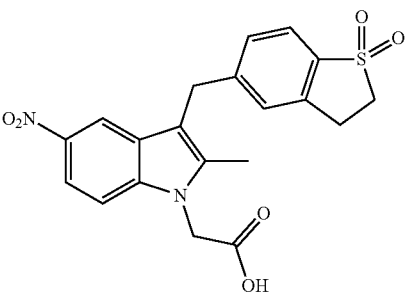

141
-continued
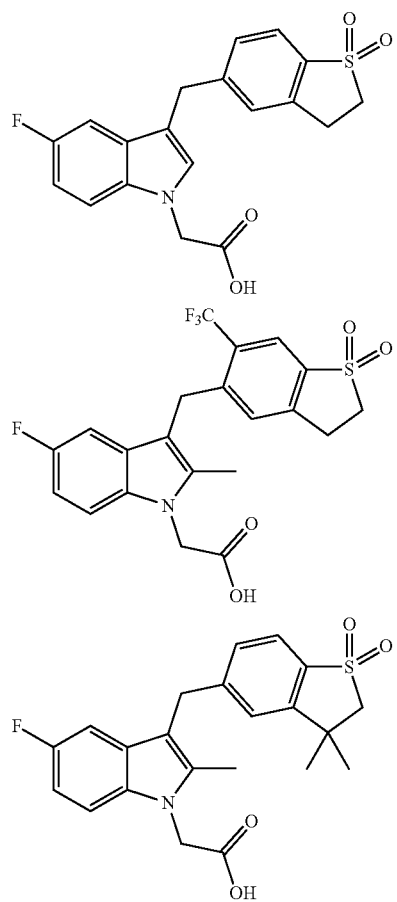
142
-continued
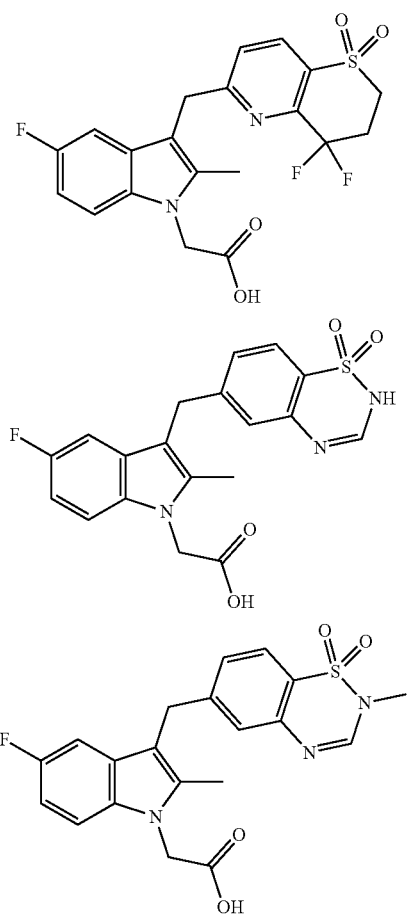
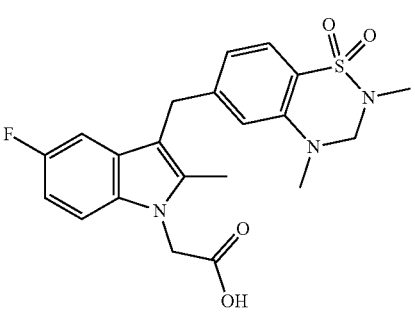
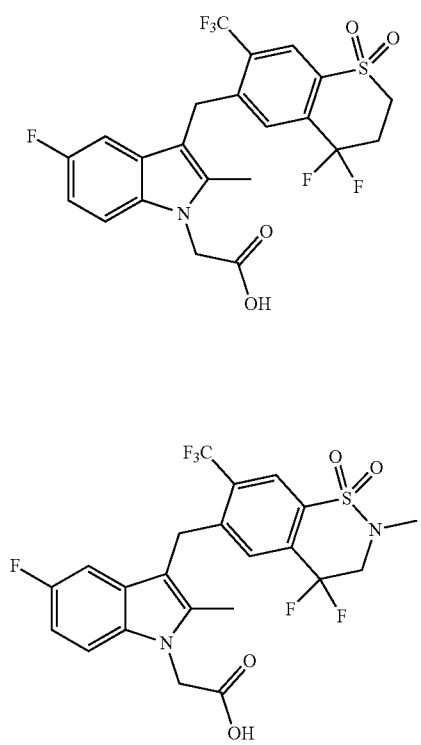

143
-continued

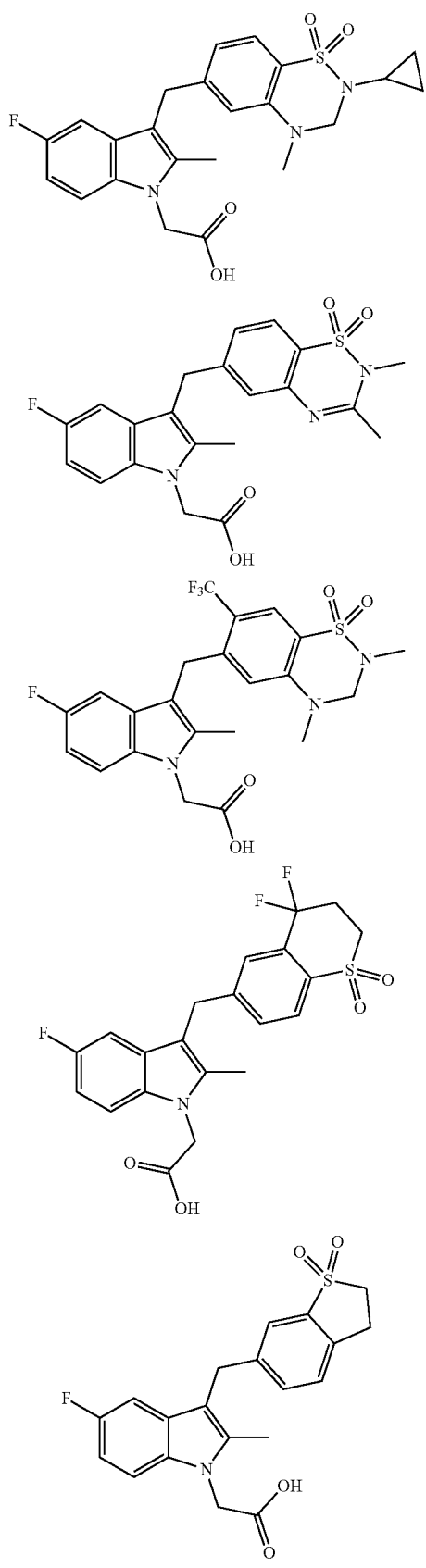

144
-continued

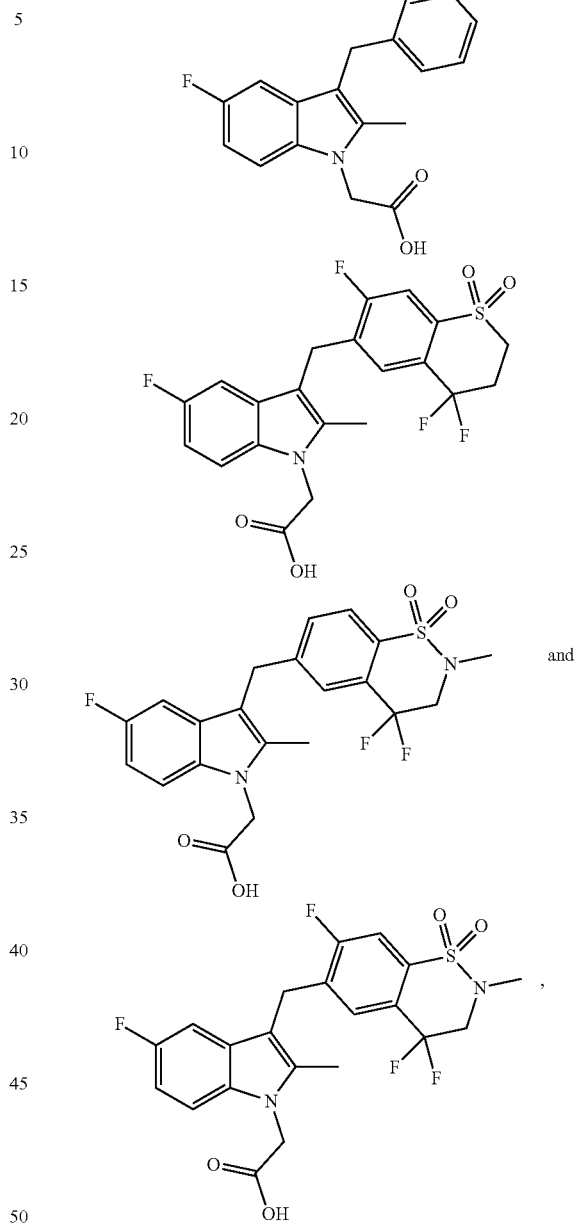

or a pharmaceutically acceptable salt, tautomer, or solvate thereof.

5. A pharmaceutical composition, comprising the compound according to claim 1, or a pharmaceutically acceptable salt thereof, or a tautomer thereof, or a solvate thereof, and a pharmaceutically acceptable adjuvant.

6. A method for treating a disease mediated by a CRTH2 receptor in a mammal, comprising administering to a mammal in need thereof a therapeutically effective amount of the compound according to claim 1, or a pharmaceutically acceptable salt thereof, or a tautomer thereof, or a solvate thereof, wherein a disease mediated by a CRTH2 receptor is asthma or allergic rhinitis.

7. A method for treating a disease mediated by a CRTH2 receptor in a mammal, comprising administering to a mammal in need thereof a therapeutically effective amount of the pharmaceutical composition according to claim 5, wherein a disease mediated by a CRTH2 receptor is asthma or allergic rhinitis.

8. The compound according to claim 1, wherein A is selected from the group consisting of

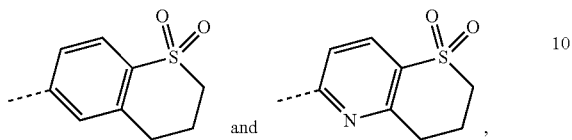

and which are substituted with F or Cl, and which are optionally substituted with one or more $R_1$; and L is methylene.

9. The compound according to claim 1, wherein each $R_1$ is independently selected from the group consisting of F, Cl, Br, I, and —OH; or is independently selected from the following groups: Me,

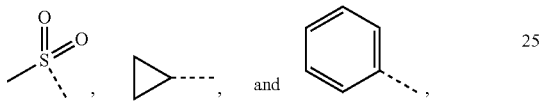

and which are optionally substituted with 1, 2, or 3 R.

10. The compound according to claim 1, wherein each $R_1$ is independently selected from the group consisting of F, Cl, Me, —$CF_3$,

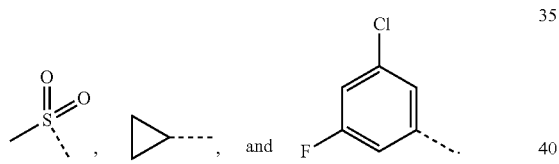

and

11. The compound according to claim 1, wherein each $R_1$ is independently selected from the group consisting of F, Cl, and —$CF_3$.

12. The compound according to claim 1, wherein $R_5$ is —$CH_3$.

13. The compound according to claim 1, wherein each $R_3$ is independently selected from the group consisting of H, F, Cl, Br, I, —OH, —$NO_2$, Me, and —$CF_3$.

14. The compound according to claim 4, selected from the group consisting of:

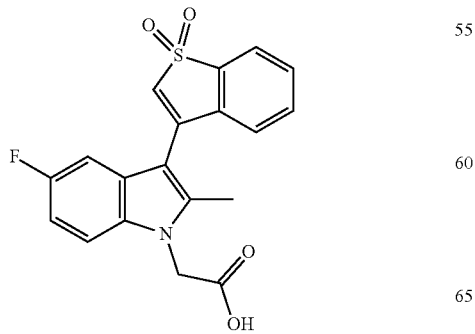

-continued

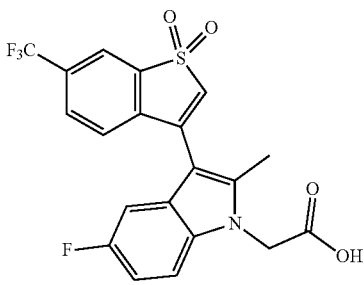

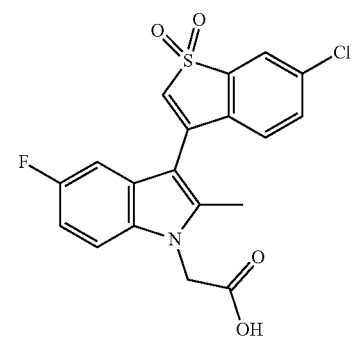

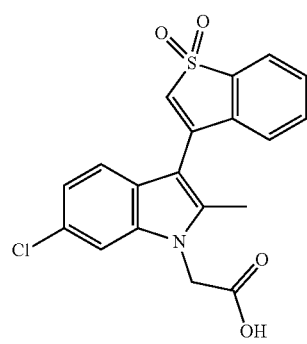

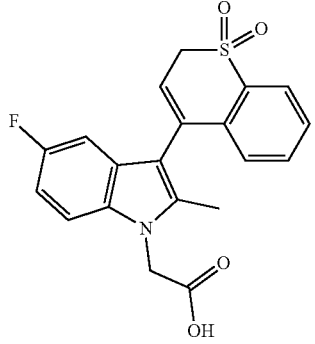

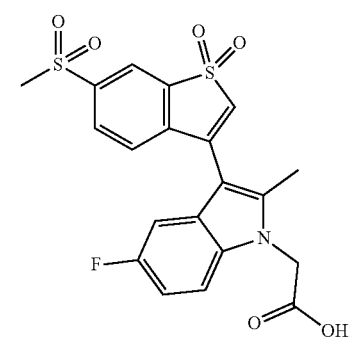

147
-continued
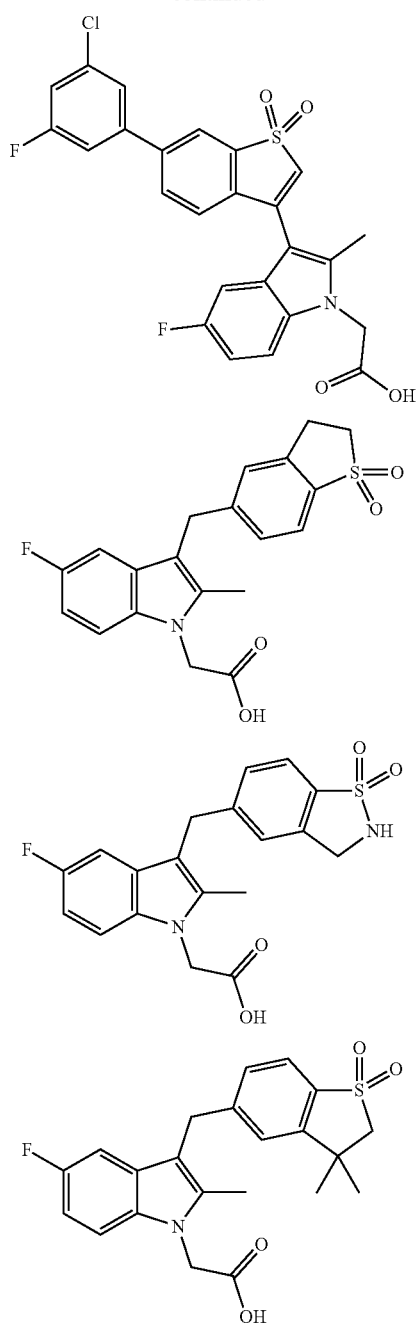
148
-continued
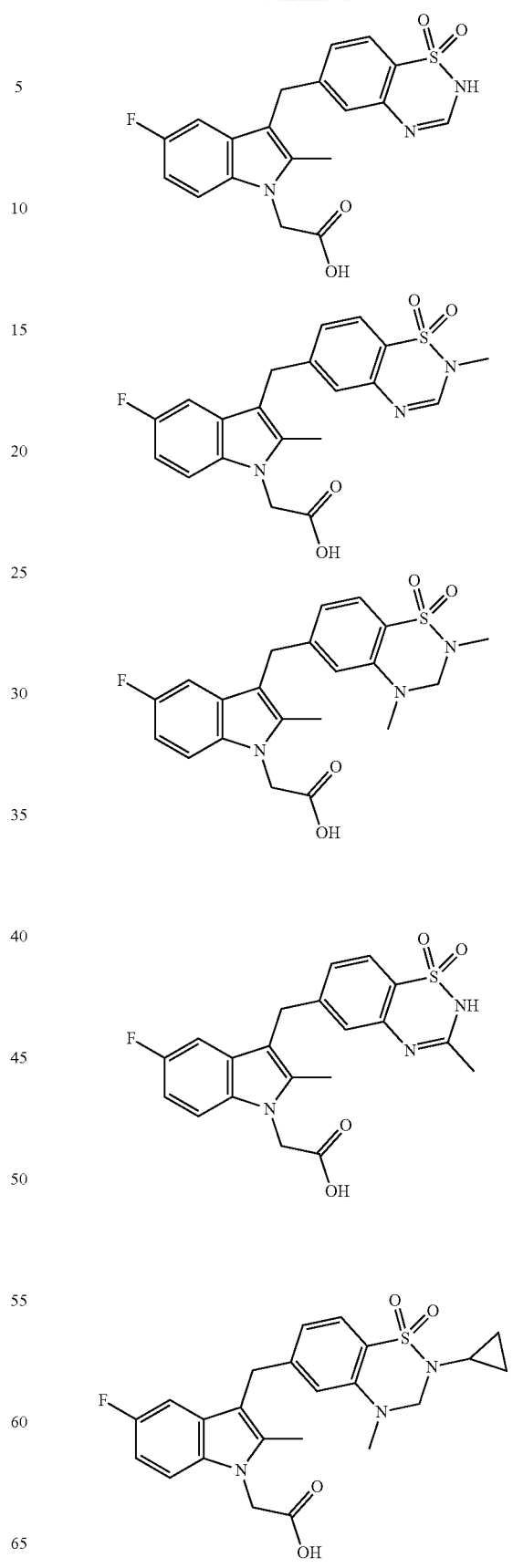

149
-continued
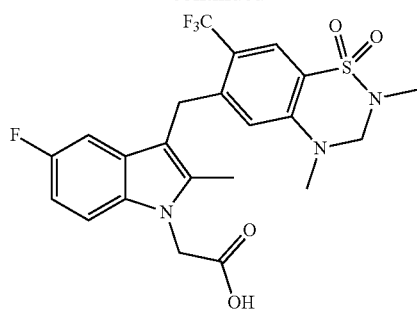
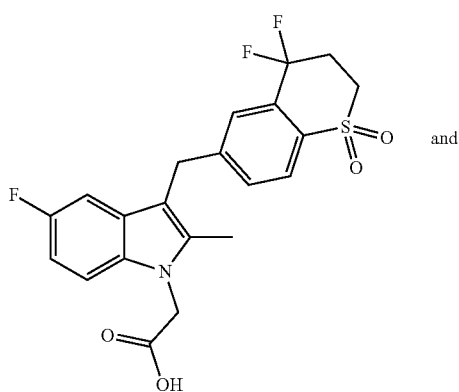
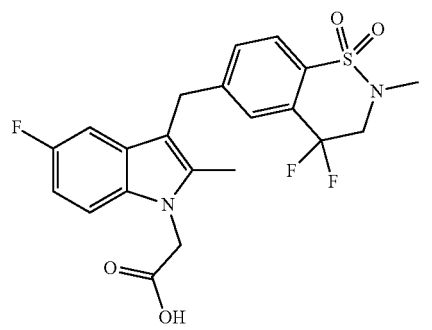
150
-continued
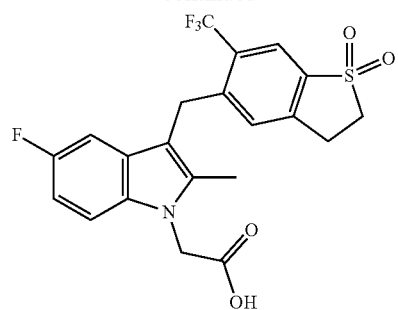
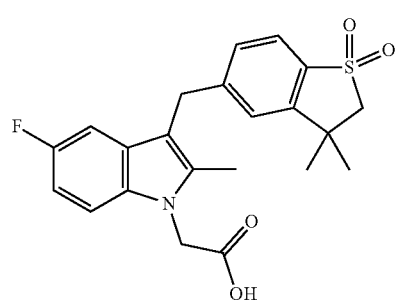
and
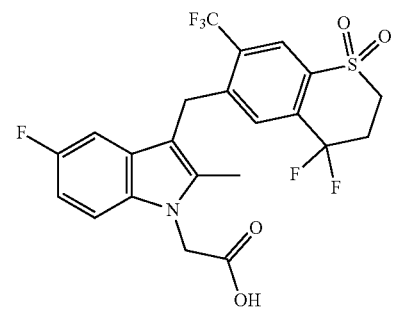
15. The compound according to claim 4, selected from the group consisting of:
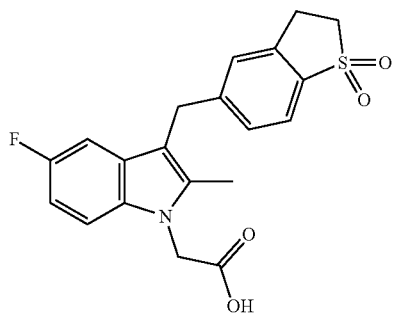
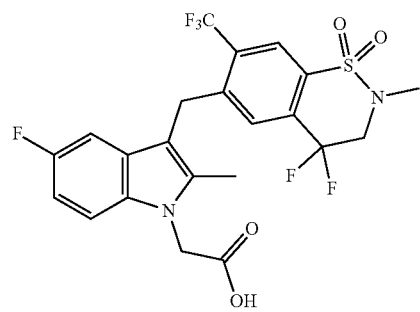

151
-continued
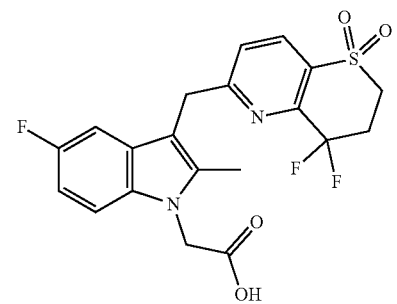
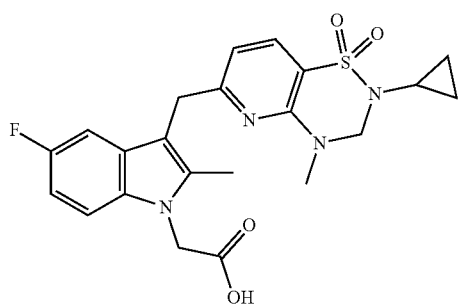
152
-continued
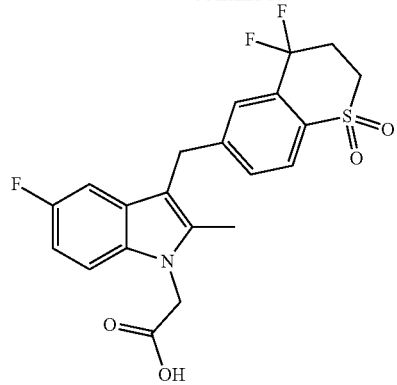
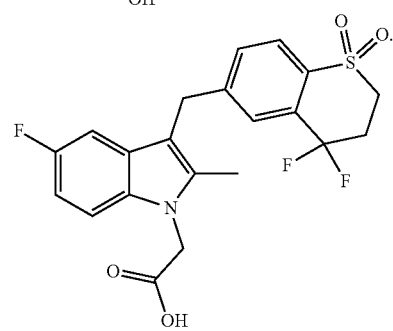
and
* * * * *